(12) United States Patent
Bodepudi et al.

(10) Patent No.: US 7,928,207 B2
(45) Date of Patent: *Apr. 19, 2011

(54) SYNTHESIS AND COMPOSITIONS OF NUCLEIC ACIDS COMPRISING 2'-TERMINATOR NUCLEOTIDES

(75) Inventors: Veeraiah Bodepudi, San Ramon, CA (US); Amar P. Gupta, Danville, CA (US); Stephen G. Will, Oakland, CA (US)

(73) Assignee: Roche Molecular Systems, Inc, Pleasanton, CA (US)

( * ) Notice: Subject to any disclaimer, the term of this patent is extended or adjusted under 35 U.S.C. 154(b) by 386 days.

This patent is subject to a terminal disclaimer.

(21) Appl. No.: 11/583,605

(22) Filed: Oct. 18, 2006

(65) Prior Publication Data

US 2007/0219361 A1 Sep. 20, 2007

Related U.S. Application Data

(63) Continuation-in-part of application No. 10/879,493, filed on Jun. 28, 2004, and a continuation-in-part of application No. 10/879,494, filed on Jun. 28, 2004.

(51) Int. Cl.
*C07H 21/02* (2006.01)
*C12Q 1/68* (2006.01)
(52) U.S. Cl. .................. 536/23.1; 435/6; 435/975
(58) Field of Classification Search .................. None
See application file for complete search history.

(56) References Cited

U.S. PATENT DOCUMENTS

| 5,532,130 | A | | 7/1996 | Alul |
| 5,547,835 | A | * | 8/1996 | Koster ........................ 435/6 |
| 5,859,221 | A | * | 1/1999 | Cook et al. .................. 536/23.1 |
| 6,635,452 | B1 | * | 10/2003 | Monforte et al. .................. 506/9 |
| 2007/0154914 | A1 | | 7/2007 | Gelfand et al. |

FOREIGN PATENT DOCUMENTS

| EP | 2007008997 | 10/2007 |
| WO | 2005005667 A2 | 1/2005 |
| WO | 2005005667 A3 | 1/2005 |
| WO | 2005118608 A2 | 12/2005 |
| WO | 2005118608 A3 | 12/2005 |
| WO | 2004/021075 | 7/2007 |
| WO | 2007075967 A2 | 7/2007 |
| WO | 2007075967 A3 | 7/2007 |

OTHER PUBLICATIONS

Carroll et al. ("Inhibition of hepatitis C virus RNA replication by 2'-modified nucleoside analogs" J Biol Chem. Apr. 4, 2003;278(14):11979-84. Epub Jan. 27, 2003).*
Stratagene ("Gene Characterization Kits" 1988).*
Hamel ("Derivatives of guanosine triphosphate with ribose 2'-hydroxyl substituents. Interactions with the protein synthetic enzymes of *Escherichia coli*" Eur J Biochem. Nov. 15, 1976;70(2):339-47.*
Messens, E., et al. (1968) "The Synthesis of Nucleoside 2' (3')-Phosphate 5'-Triphosphates," FEBS Letters, vol. 1, No. 5: 326-328.
Zhang, Jia, et al., 2005 "Proofreading genotyping assays mediated by high fidelity exo + DNA polymerases", Trends in Biotechnology, 23(2):92-96.

* cited by examiner

*Primary Examiner* — Christopher M. Babic
(74) *Attorney, Agent, or Firm* — Rhea C. Nersesian; Olga Kay

(57) ABSTRACT

The invention provides methods of producing blocked oligonucleotides that include 2'-terminator nucleotides. These blocked oligonucleotides are used primers and probes in a variety of nucleic acid technologies. Related kits are also provided.

8 Claims, 36 Drawing Sheets

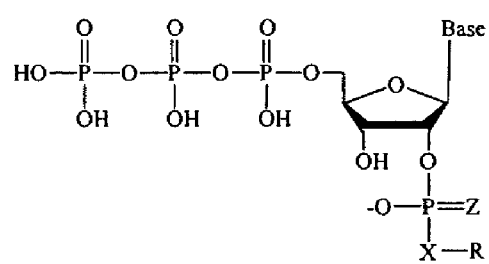 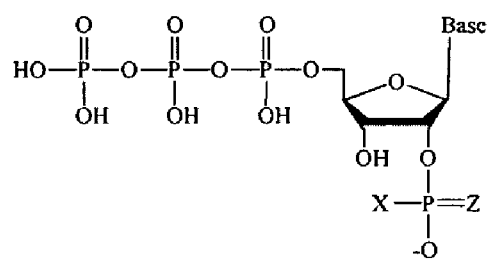
Fig. 2A                    Fig. 2B

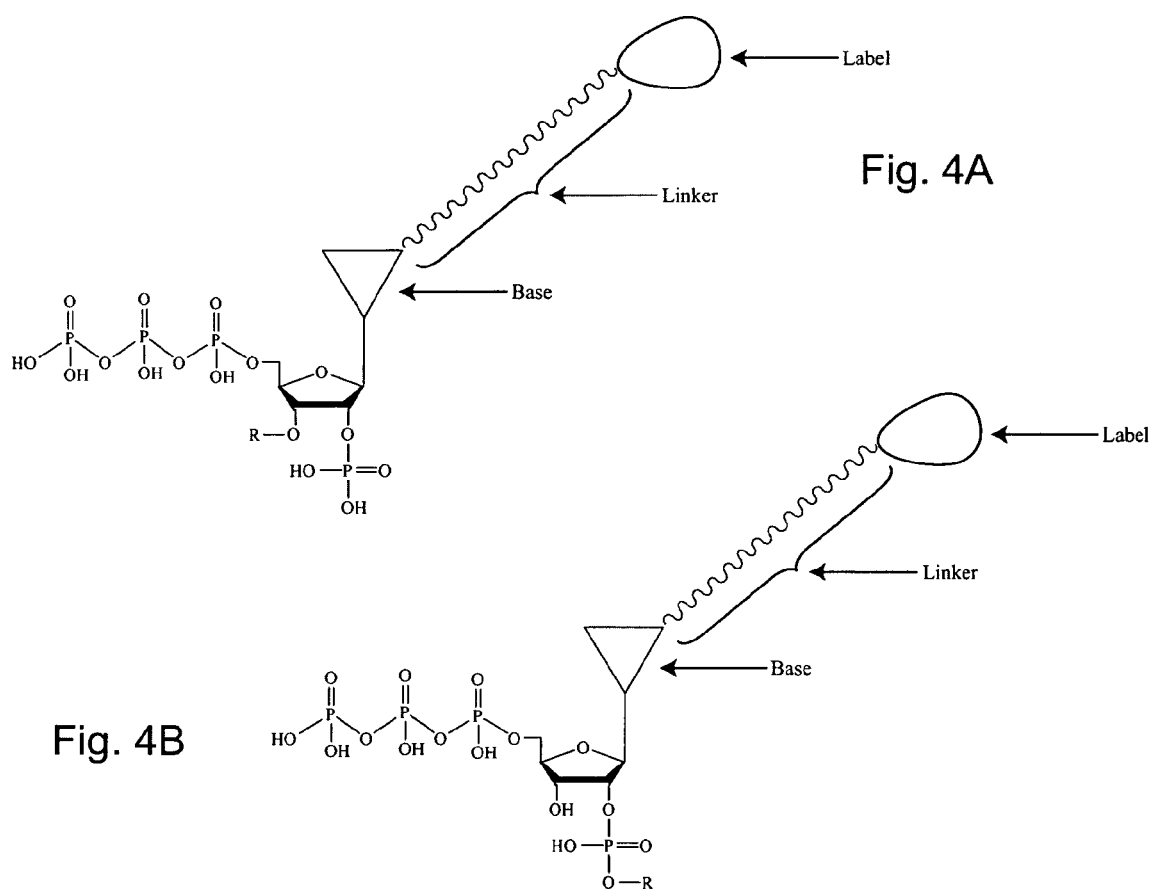

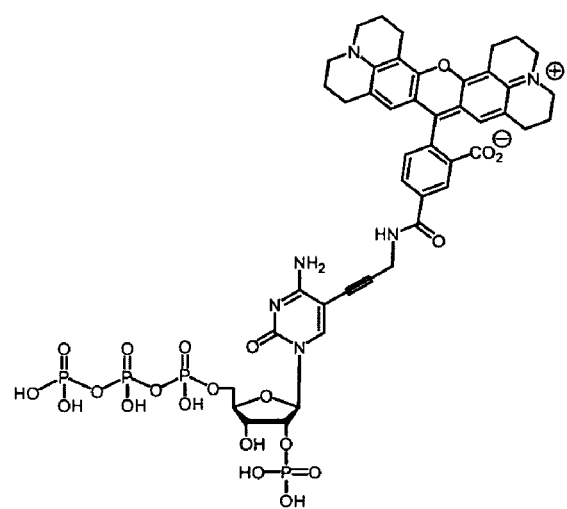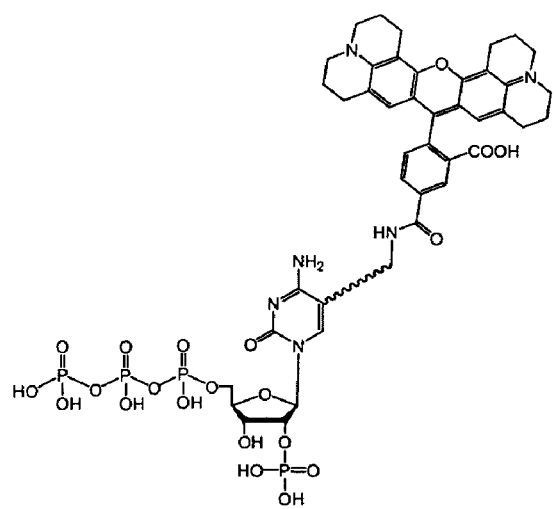
Fig. 6K  Fig. 6L
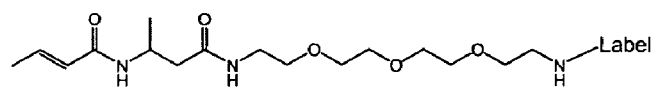
Fig. 7

2400 | receive an order from a customer for one or more blocked oligonucleotides and/or instructions for producing blocked oligonucleotides 2402 | supply the blocked oligonucleotides and/or instructions in response to the order

SEQUENCE LISTING

```
<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)
<223> OTHER INFORMATION: 2'-amino(ribo)C

<400> SEQUENCE: 1
cgccagggtt ttcccagtna                                             20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)
<223> OTHER INFORMATION: 2'-amino(ribo)C

<400> SEQUENCE: 2
cgccagggtt ttcccagtna                                             20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
```

```
<221> NAME/KEY: modified_base
<222> LOCATION: (19)
<223> OTHER INFORMATION: 2'-amino(ribo)C

<400> SEQUENCE: 3
cgccagggtt ttcccagtna                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)
<223> OTHER INFORMATION: 2'-amino(ribo)C

<400> SEQUENCE: 4
cgccagggtt ttcccagtna                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)
<223> OTHER INFORMATION: 2'-amino(ribo)C

<400> SEQUENCE: 5
cgccagggtt ttcccagtna                                              20

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgagacacca ggaattagat atcagtacaa tgt                               33

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctaaatcaga tcctacatat aagtcatcca tgt                               33

<210> SEQ ID NO 8
<211> LENGTH: 33
<212> TYPE: DNA
<213> ORGANISM: Artificial Sequence
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer
<220> FEATURE:
```

```
<221> NAME/KEY: modified_base
<222> LOCATION: (33)
<223> OTHER INFORMATION: 2'-phosphate-u

<400> SEQUENCE: 8
tgagacacca ggaattagat atcagtacaa tgu                              33

<210> SEQ ID NO 9
<211> LENGTH: 33
<212> TYPE: DNA
<213> ORGANISM: Artificial Sequence
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer
<220> FEATURE:
<221> NAME/KEY: modified_base
<222> LOCATION: (33)
<223> OTHER INFORMATION: 2'-phosphate-u

<400> SEQUENCE: 9
ctaaatcaga tcctacatat aagtcatcca tgu                              33

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaacttgtgg tagttggagc tc                                          22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gttggatcat attcgtccac aa                                          22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)
<223> OTHER INFORMATION: 2'-phosphate-c

<400> SEQUENCE: 12
aaacttgtgg tagttggagc tc                                          22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
```

```
<221> NAME/KEY: modified_base
<222> LOCATION: (22)
<223> OTHER INFORMATION: 2'-phosphate-a

<400> SEQUENCE: 13
gttggatcat attcgtccac aa                                              22

<210> SEQ ID NO 14
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer
<220> FEATURE:
<221> NAME/KEY: modified_base
<222> LOCATION: (23)
<223> OTHER INFORMATION: 2'-phosphate-u

<400> SEQUENCE: 14
aaacttgtgg tagttggagc tgu                                             23

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)
<223> OTHER INFORMATION: 2'-phosphate-a

<400> SEQUENCE: 15
gttggatcat attcgtccac aa                                              22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)
<223> OTHER INFORMATION: 2'-amino-c

<400> SEQUENCE: 16
cgcctggtct gtacaccgtt na                                              22

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)
<223> OTHER INFORMATION: 2'-phosphate-a

<400> SEQUENCE: 17
ggaacgaggg tagcaacggc tacn                                            24
```

-continued

```
<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcaagcaccc tatcaggcag taccacaa                                        28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (28)
<223> OTHER INFORMATION: 2'-phosphate-a or 2'-monophosphate-3'-
      hydroxyl-a

<400> SEQUENCE: 19
gcaagcaccc tatcaggcag taccacaa                                        28

<210> SEQ ID NO 20
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer
<220> FEATURE:
<221> NAME/KEY: modified_base
<222> LOCATION: (27)
<223> OTHER INFORMATION: 2'-phosphate-u or 2'-monophosphate-3'-
      hydroxyl-u

<400> SEQUENCE: 20
aataggtgat tttggtctag ctacagu                                         27

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)
<223> OTHER INFORMATION: 2'-phosphate-a or 2'-monophosphate-3'-
      hydroxyl-a

<400> SEQUENCE: 21
ggacccactc catcgagatt tca                                             23

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (27)
```

```
<223> OTHER INFORMATION: 2'-phosphate-a or 2'-monophosphate-3'-
      hydroxyl-a

<400> SEQUENCE: 22
aataggtgat tttggtctag ctacaga                                           27

<210> SEQ ID NO 23
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer
<220> FEATURE:
<221> NAME/KEY: modified_base
<222> LOCATION: (23)
<223> OTHER INFORMATION: 2'-phosphate-u or 2'-monophosphate-3'-
      hydroxyl-u

<400> SEQUENCE: 23
ggacccactc catcgagatt tcu                                               23

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcaagcaccc tatcaggcag taccaca                                           27

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttgtggtact gcctgatagg gtgcttgc                                          28

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcaagcaccc tatcaggcag taccaca                                           27

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcagaaagcg tctagccatg gctta                                             25
```

```
<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccctcgcagc cgtccaacca actca                                              25

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gggagcgtcg gcaggttggt tgagttccac aaccac                                  36

<210> SEQ ID NO 30
<211> LENGTH: 120
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: modified_base
<222> LOCATION: (3)
<223> OTHER INFORMATION: a, c, g, t, unknown, or other
<220> FEATURE:
<221> NAME/KEY: modified_base
<222> LOCATION: (5)
<223> OTHER INFORMATION: a, c, g, t, unknown, or other

<400> SEQUENCE: 30
aangnaggcc agtgccaagc ttgcatgcct gcaggtcgac tctagaggat ccccgggtac        60
cgagctcgaa ttcgtaatca tggtcatagc tgtttcctgt gtgaaattgt tatccgctca       120

<210> SEQ ID NO 31
<211> LENGTH: 120
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 31
caattccaca caacatacga gccggaagca taaagtgtaa agcctggggt gcctaatgag        60
tgagctaact cacattaatt gcgttgcgct cactgcccgc tttccagtcg ggaaacctgt       120

<210> SEQ ID NO 32
<211> LENGTH: 121
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 32
tcgtgccagc tgcattaatg aatcggccaa cgcgcgggga gaggcggttt gcgtattggg        60
cgccagggtg ttttttcttt tcaccagtga cgggcaac agctgattgc ccttcaccgc        120
c                                                                      121
```

```
<210> SEQ ID NO 33
<211> LENGTH: 119
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 33
tggccctgag agagttgcag caagcggtcc acgctggttt gccccagcag gcgaaaatcc      60
tgtttgatgg tggttccgaa atcggcaaaa tcccttataa atcaaaagaa tagcccgag      119

<210> SEQ ID NO 34
<211> LENGTH: 121
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 34
gatagggttg agtgttgttc cagtttggaa caagagtcca ctattaaaga acgtggactc      60
caacgtcaaa gggcgaaaaa ccgtctatca gggcgatggc ccactacgtg aaccatcacc      120
c                                                                     121
```

SYNTHESIS AND COMPOSITIONS OF NUCLEIC ACIDS COMPRISING 2'-TERMINATOR NUCLEOTIDES

CROSS-REFERENCES TO RELATED APPLICATIONS

This application is a continuation-in-part of U.S. patent application Ser. No. 10/879,494, entitled "SYNTHESIS AND COMPOSITIONS OF 2'-TERMINATOR NUCLEOTIDES", filed Jun. 28, 2004 and also a continuation-in-part of U.S. patent application Ser. No. 10/879,493, entitled "2'-TERMINATOR NUCLEOTIDE-RELATED METHODS AND SYSTEMS," filed Jun. 28, 2004, the disclosures of which are incorporated by reference.

FIELD OF THE INVENTION

The invention relates generally to nucleic acids comprising 2'-terminator nucleotides and to methods of their production.

BACKGROUND OF THE INVENTION

Blocked or non-extendible oligonucleotides and polynucleotides include moieties, such as terminator nucleotides, which prevent additional nucleotides from being added to the oligonucleotides and polynucleotides under a given set of reaction conditions. These molecules are commonly used in various nucleic acid technologies. To illustrate, blocked oligonucleotides are used as probes in some applications, such as a real-time polymerase chain reaction (PCR) to prevent probes from being extended during the extension steps of the reaction. To further illustrate, blocked oligonucleotides are also used as primers in certain applications. For example, pyrophosphorolysis activated polymerization (PAP) is a PCR method that involves primers having 3' terminal terminator nucleotides, which are removed by pyrophosphorolysis before the primers can be extended. Pre-existing PAP methods typically use dideoxy-terminated primers and dideoxy-incorporating polymerases. The polymerases used in these pre-existing approaches often have limited abilities to extend primer nucleic acids and accordingly, produce inefficient amplification reactions.

Additional oligonucleotides and polynucleotides that include terminator nucleotides of use in real-time PCR, PAP, and other nucleic acid technologies are desirable. The present invention provides oligonucleotides and polynucleotides comprising 2'-terminator nucleotides that are useful in these applications. These and a variety of other features of the invention will be apparent upon a complete review of the following disclosure.

SUMMARY OF THE INVENTION

The invention relates to oligonucleotides and polynucleotides including 2'-terminator nucleotides that are economical alternatives to pre-existing blocked oligonucleotides and polynucleotides. For example, the blocked oligonucleotides described herein are readily substituted in various PCR-related protocols without sacrificing ease of use. The 2'-terminator nucleotides of the oligonucleotides and polynucleotides described herein typically have intact sugar rings or sugar analog rings (e.g., carbocyclic rings, etc.), and include blocking groups (e.g., negatively charged blocking groups, bulky blocking groups, and/or the like) at 2'-positions of these sugar moieties. In addition to methods of producing these oligonucleotides and polynucleotides, the invention also provides related business methods and kits.

In one aspect, the invention provides an oligonucleotide or polynucleotide that comprises the formula:

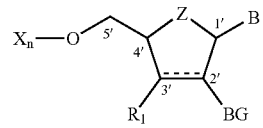

where Z is O or $CH_2$; B is at least one homocyclic ring, at least one heterocyclic ring, at least one aryl group, or combinations thereof; BG is a blocking group; $R_1$ is H, OH, a hydrophilic group, or a hydrophobic group; X is a nucleotide or a nucleotide analog; n is an integer greater than 0; and, ===== represents a single or double bond. In certain embodiments, at least one label (e.g., a donor moiety, a quencher moiety, an acceptor moiety, reporter moiety, etc.) is attached to the oligonucleotide or polynucleotide. In some of these embodiments, the label is attached to the oligonucleotide or polynucleotide via at least one linker moiety.

In one aspect, the invention provides a method of producing an oligonucleotide or polynucleotide. The method includes (a) providing a nucleic acid synthesis reagent comprising the formula:

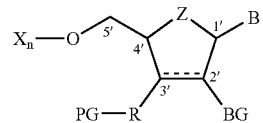

where Z is O or $CH_2$; B is at least one homocyclic ring, at least one heterocyclic ring, at least one aryl group, or combinations thereof; BG is a blocking group; R is O, NH, or S; PG is a protecting group; X is a nucleotide or a nucleotide analog; n is an integer greater than 0; and ===== represents a single or double bond. In addition, the method also includes (b) removing PG from the nucleic acid synthesis reagent to produce an oligonucleotide comprising the formula:

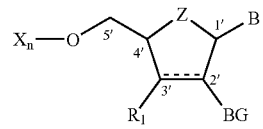

where $R_1$ is H, OH, a hydrophilic group, or a hydrophobic group, thereby producing the oligonucleotide or polynucleotide. In some embodiments, the method includes attaching the nucleic acid synthesis reagent, or a component thereof (e.g., a precursor reagent, such as a phosphoramidite), to a solid support prior to (b). In certain embodiments, the method includes attaching at least one label (e.g., a donor moiety, a quencher moiety, an acceptor moiety, etc.) to the nucleic acid synthesis reagent, a component thereof, and/or the oligonucleotide or polynucleotide. In some of these embodiments, the label is attached to the nucleic acid synthesis reagent, the component thereof, and/or the oligonucleotide or polynucleotide via at least one linker moiety.

Various protecting groups are optionally utilized in the method of producing the oligonucleotide or polynucleotide.

In some embodiments, for example, the protecting group is selected from, e.g., a trityl group, a monomethoxytrityl group, a dimethoxytrityl group, a levulinyl group, a fluorenylmethoxycarbonyl group, a benzhydryloxycarbonyl group, and the like. To further illustrate, in certain embodiments, the protecting group comprises the formula:

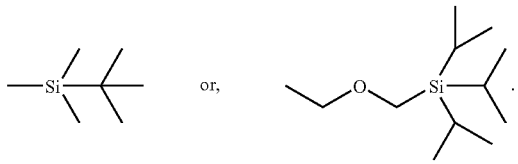

In certain embodiments, the 2'-terminator nucleotide comprises the formula:

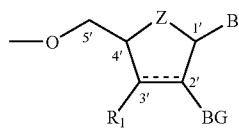

in which $R_1$ is H, OH, a hydrophilic group, or a hydrophobic group; B is at least one homocyclic ring, at least one heterocyclic ring, at least one aryl group, or combinations thereof; BG is a blocking group; Z is O or $CH_2$; and ≡≡≡ represents a single or double bond. In some embodiments, for example, the 2'-terminator nucleotide comprises a 2'-monophosphate-3'-hydroxyl nucleotide. Further, the 2'-terminator nucleotide is generally non-extendible by one or more nucleotide incorporating biocatalysts selected from, e.g., a G46E E678G CS5 DNA polymerase, a G46E L329A E678G CS5 DNA polymerase, a G46E L329A D640G S671F CS5 DNA polymerase, a G46E L329A D640G S671F E678G CS5 DNA polymerase, a G46E E678G CS6 DNA polymerase, a ΔZ05R polymerase, a E615G Taq DNA polymerase, a *Thermus flavus* polymerase, a TMA-25 polymerase, a E678G TMA-25 polymerase, a TMA-30 polymerase, a E678G TMA-30 polymerase, a Tth DNA polymerase, a *Thermus* specie SPS-17 polymerase, a E615G Taq polymerase, a *Thermus* Z05R polymerase, a T7 DNA polymerase, a Kornberg DNA polymerase I, a Klenow DNA polymerase, a Taq DNA polymerase, a Micrococcal DNA polymerase, an alpha DNA polymerase, a reverse transcriptase, an AMV reverse transcriptase, an M-MuLV reverse transcriptase, a DNA polymerase, an RNA polymerase, a *E. coli* RNA polymerase, an SP6 RNA polymerase, a T3 RNA polymerase, a T4 DNA polymerase, a T7 RNA polymerase, an RNA polymerase II, a terminal transferase, a polynucleotide phosphorylase, a ribonucleotide incorporating DNA polymerase, and the like.

In another aspect, the invention provides a business method that includes (a) receiving an order from a customer for one or more of: (i) instructions for producing an oligonucleotide or polynucleotide comprising a 2'-terminator nucleotide, or (ii) an oligonucleotide or polynucleotide comprising a 2'-terminator nucleotide. The method also includes (b) providing (i) and/or (ii) to the customer. In certain embodiments, the method includes receiving the order via an electronic medium (e.g., through the internet, etc.).

In another aspect, the invention provides a kit that includes one or more of: (a) instructions for producing an oligonucleotide or polynucleotide comprising a 2'-terminator nucleotide; or, (b) at least one oligonucleotide or polynucleotide comprising a 2'-terminator nucleotide.

BRIEF DESCRIPTION OF THE DRAWINGS

FIGS. 2A and B schematically show some embodiments of 2'-terminator nucleotides.

FIGS. 4A and B schematically show certain embodiments of labeled nucleotide tetraphosphates.

FIG. 6A-L schematically show various 2'-terminator nucleotides having attached fluorescent dyes.

FIG. 7 schematically depicts an exemplary linker.

DETAILED DESCRIPTION

I. Definitions

Figure 1A:
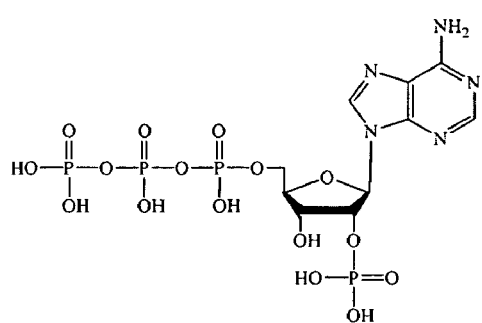
FIGS. 1A-D schematically illustrate exemplary 2'-terminator nucleotides.

Before describing the present invention in detail, it is to be understood that this invention is not limited to particular methods or kits, which can vary. As used in this specification and the appended claims, the singular forms "a," "an," and "the" also include plural referents unless the context clearly provides otherwise. Thus, for example, reference to "a 2'-monophosphate-3'-hydroxyl nucleoside" also includes a combination of two or more 2'-monophosphate-3'-hydroxyl nucleosides. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology, and grammatical variants thereof, will be used in accordance with the definitions set forth below.

A "2'-terminator nucleotide" refers to a nucleotide analog that comprises a blocking group (BG) at the 2'-position of the sugar moiety of the nucleotide. A "blocking group" refers to a chemical group or moiety that typically prevents the extension of a nucleic acid (i.e., a 2'-terminator nucleotide is typically non-extendible by one or more nucleotide incorporating biocatalysts). That is, once a 2'-terminator nucleotide is incorporated into a nucleic acid (e.g., at a 3'-terminal end of the nucleic acid), the blocking group prevents further extension of a nucleic acid by at least one nucleotide incorporating biocatalyst selected from, e.g., a G46E E678G CS5 DNA polymerase, a G46E L329A E678G CS5 DNA polymerase, a G46E L329A D640G S671F CS5 DNA polymerase, a G46E L329A D640G S671F E678G CS5 DNA polymerase, a G46E E678G CS6 DNA polymerase, a ΔZ05R polymerase, a E615G Taq DNA polymerase, a *Thermus flavus* polymerase, a TMA-25 polymerase, a E678G TMA-25 polymerase, a TMA-30 polymerase, a E678G TMA-30 polymerase, a Tth DNA polymerase, a *Thermus* specie SPS-17 polymerase, a E615G Taq polymerase, a *Thermus* Z05R polymerase, a T7 DNA polymerase, a Kornberg DNA polymerase I, a Klenow DNA polymerase, a Taq DNA polymerase, a Micrococcal DNA polymerase, an alpha DNA polymerase, a reverse transcriptase, an AMV reverse transcriptase, an M-MuLV reverse transcriptase, a DNA polymerase, an RNA polymerase, a *E. coli* RNA polymerase, an SP6 RNA polymerase, a T3 RNA polymerase, a T4 DNA polymerase, a T7 RNA polymerase, an RNA polymerase II, a terminal transferase, a polynucleotide phosphorylase, a ribonucleotide incorporating DNA polymerase, and the like. An exemplary blocking group is a phosphate group. Other representative blocking groups are also described herein. Exemplary 2'-terminator nucleotides include 2'-monophosphate-3'-hydroxyl-5'-triphosphate nucleosides and 2'-monophosphate-3'-hydroxyl-5'-diphosphate nucleosides. Other 2'-terminator nucleotides are also described further herein.

An "acceptor moiety" or "acceptor" refers to a moiety that is capable of accepting or absorbing energy transferred from an energy source. In some embodiments, acceptor moieties are also capable of emitting energy (e.g., light, heat, etc.) upon absorbing sufficient amounts of transferred energy. In these embodiments, acceptors are also known as "reporter moieties" or as "reporters". Exemplary acceptor moieties include, but are not limited to, various fluorophores, such as LightCycler®-Red 610 (LC-Red 610), LC-Red 640, LC-Red 670, LC-Red 705, JA-270, CY5, CY5.5, among many others.

An "alcohol group" refers to an organic group that includes at least one hydroxy group.

An "aldehyde group" refers to an organic group that includes the formula CHO.

An "alkenyl group" refers to a linear, branched, or cyclic unsaturated hydrocarbon moiety that comprises one or more carbon-carbon double bonds. Exemplary alkenyl groups include ethenyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-2-propenyl, and the like. An alkenyl group typically comprises about 1-20 carbon atoms and more typically comprises about 2-15 carbon atoms. Alkenyl groups can be substituted or unsubstituted.

An "alkenylamine group" refers to an amino group that comprises at least one alkenyl group.

An "alkoxy group" refers to an alkyl group that comprises an oxygen atom and includes, e.g., methoxy, ethoxy, propoxy, butoxy, pentoxy, heptyloxy, octyloxy, and the like.

An "alkyl group" refers to a linear, branched, or cyclic saturated hydrocarbon moiety and includes all positional isomers, such as methyl, ethyl, propyl, isopropyl, butyl, pentyl, hexyl, heptyl, octyl, nonyl, 1-methylethyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, n-hexyl, cyclohexyl, n-heptyl, n-octyl, 2-ethylhexyl, n-nonyl, n-decyl and the like. An alkyl group typically comprises about 1-20 carbon atoms and more typically comprises about 2-15 carbon atoms. Alkyl groups can be substituted or unsubstituted.

An "alkylamine group" refers to an amino group that comprises at least one alkyl group.

An "alkynyl group" refers to a linear, branched, or cyclic unsaturated hydrocarbon moiety that comprises one or more carbon-carbon triple bonds. Representative alkynyl groups include, e.g., 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl 1-ethyl-1-methyl-2-propynyl, and the like. An alkynyl group typically comprises about 1-20 carbon atoms and more typically comprises about 2-15 carbon atoms. Alkynyl groups can be substituted or unsubstituted.

An "alkynylamine group" refers to an amino group that comprises at least one alkynyl group.

An "aryl group" refers to a substituent group of atoms or moiety that is derived from an aromatic compound. Exemplary aryl groups include, e.g., phenyl groups, benzyl groups, tolyl groups, xylyl groups, or the like. Aryl groups optionally include multiple aromatic rings (e.g., diphenyl groups, etc.). In addition, an aryl group can be substituted or unsubstituted.

An "aryloxy group" refers an aryl group that comprises an oxygen atom and includes, e.g., phenoxy, chlorophenoxy, methylphenoxy, methoxyphenoxy, butylphenoxy, pentylphenoxy, benzyloxy, and the like.

The term "attaching" refers to a process in which two or more materials covalently and/or non-covalently associate with one another, even if only transiently. In certain embodiments, for example, nucleic acid synthesis reagents attached to one another as part of methods of producing oligonucleotides.

A "donor moiety" refers a moiety that is capable of transferring, emitting, or donating one or more forms of excitation energy to one or more acceptor moieties.

An "ester group" refers to a class of organic compounds that includes the general formula RCOOR', where R and R' are independently selected from an alkyl group, an alkenyl group, an alkynyl group, an aryl group, or combinations thereof.

An "ether group" refers to a linear, branched, or cyclic moiety that comprises two carbon atoms attached to a single oxygen atom. Exemplary ether groups include, e.g., methoxymethyl, methoxyethyl, methoxypropyl, ethoxyethyl, and the like.

A "halo group" refers to a group that comprises a halogen atom, such as F, Cl, Br, or I.

A "heterocyclic ring" refers to a monocyclic or bicyclic ring that is either saturated, unsaturated, or aromatic, and which comprises one or more heteroatoms independently selected from nitrogen, oxygen and sulfur. A heterocyclic ring may be attached to the sugar moiety, or analog thereof, of a nucleotide of the invention via any heteroatom or carbon atom. Exemplary heterocyclic rings include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, quinazolinyl, and the like.

A "homocyclic ring" refers to a saturated or unsaturated (but not aromatic) carbocyclic ring, such as cyclopropane, cyclobutane, cyclopentane, cyclohexane, cycloheptane, cyclohexene, and the like.

A "label" refers to a moiety attached (covalently or non-covalently), or capable of being attached, to a molecule, which moiety provides or is capable of providing information about the molecule (e.g., descriptive, identifying, etc. information about the molecule). Exemplary labels include fluorescent labels, non-fluorescent labels, colorimetric labels, chemiluminescent labels, bioluminescent labels, radioactive labels, mass-modifying groups, antibodies, antigens, biotin, haptens, and enzymes (including, e.g., peroxidase, phosphatase, etc.).

A "moiety" or "group" refers to one of the portions into which something, such as a molecule, is or can be divided (e.g., a functional group, substituent group, or the like). For example, an oligonucleotide of the invention includes at least one donor moiety and/or at least one acceptor moiety in certain embodiments.

A "non-extendible" nucleotide refers to a nucleotide, which upon incorporation into a nucleic acid prevents further extension of the nucleic acid, e.g., by at least one nucleotide incorporating biocatalyst.

The term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as modified forms thereof, peptide nucleic acids (PNAs), locked nucleic acids (LNA™s), and the like. In certain embodiments, a nucleic acid can be a polymer that includes multiple monomer types, e.g., both RNA and DNA subunits. A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, a primer, etc. A nucleic acid can be, e.g., single-stranded, double-stranded, triple-stranded, etc and is not limited to any particular length. Unless otherwise indicated, a particular nucleic acid sequence optionally comprises or encodes complementary sequences, in addition to any sequence explicitly indicated.

Nucleic acids are not limited to molecules having naturally occurring polynucleotide sequences or structures, naturally occurring backbones, and/or naturally occurring internucleotide linkages. For example, nucleic acids containing one or more carbocyclic sugars are also included within this definition (Jenkins et al. (1995) Chem. Soc. Rev. pp 169-176, which is incorporated by reference). To further illustrate, although a nucleic acid will generally contain phosphodiester bonds, in some cases nucleic acid analogs are included that have alternate backbones. These include, without limitation, phosphoramide (Beaucage et al. (1993) Tetrahedron 49(10):1925 and the references therein; Letsinger (1970) J. Org. Chem. 35:3800; Sprinzl et al. (1977) Eur. J. Biochem. 81:579; Letsinger et al. (1986) Nucl. Acids Res. 14: 3487; Sawai et al. (1984) Chem. Lett. 805; Letsinger et al. (1988) J. Am. Chem. Soc. 110:4470; and Pauwels et al. (1986) Chemica Scripta 26:1419), phosphorothioate (Mag et al. (1991) Nucleic Acids Res. 19:1437 and U.S. Pat. No. 5,644,048), phosphorodithioate (Briu et al. (1989) J. Am. Chem. Soc. 111:2321), O-methylphophoroamidite linkages (Eckstein, Oligonucleotides and Analogues: A Practical Approach, Oxford University Press (1992)), and peptide nucleic acid backbones and linkages (Egholm (1992) J. Am. Chem. Soc. 114:1895; Meier et al. (1992) Chem. Int. Ed. Engl. 31:1008; Nielsen (1993) Nature 365:566; and Carlsson et al. (1996) Nature 380:207), which references are each incorporated by reference. Other analog nucleic acids include those with positively charged backbones (Denpcy et al. (1995) Proc. Natl. Acad. Sci. USA 92:6097); non-ionic backbones (U.S. Pat. Nos. 5,386,023, 5,637,684, 5,602,240, 5,216,141 and 4,469,863; Angew (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghvi and P. Dan Cook; Mesmaeker et al. (1994) Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which are each incorporated by reference. Several nucleic acid analogs are also described in, e.g., Rawls, C & E News Jun. 2, 1997 page 35, which is incorporated by reference. Modifications of the ribose-phosphate backbone may be done to facilitate the addition of additional moieties, such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases. To illustrate, certain bases used in nucleotides that act as melting temperature ($T_m$) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like. Many non-naturally occurring bases are also described in, e.g., Seela et al. (1991) Helv. Chim. Acta 74:1790, Grein et al. (1994) Bioorg. Med. Chem. Lett. 4:971-976, and Seela et al. (1999) Helv. Chim. Acta 82:1640, which are each incorporated by reference.

Additional examples of modified bases and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

A "nucleic acid synthesis reagent" refers to a compound that can be used to synthesize an oligonucleotide or other nucleic acids.

A "nucleoside" refers to a nucleic acid component that comprises a base or basic group (e.g., comprising at least one homocyclic ring, at least one heterocyclic ring, at least one aryl group, and/or the like) covalently linked to a sugar moiety (e.g., a ribose sugar, etc.), a derivative of a sugar moiety, or a functional equivalent of a sugar moiety (e.g., an analog, such as carbocyclic ring). For example, when a nucleoside includes a sugar moiety, the base is typically linked to a 1'-position of that sugar moiety. As described above, a base can be naturally occurring (e.g., a purine base, such as adenine (A) or guanine (G), a pyrimidine base, such as thymine (T), cytosine (C), or uracil (U)), or non-naturally occurring (e.g., a 7-deazapurine base, a pyrazolo[3,4-d]pyrimidine base, a propynyl-dN base, etc.). Exemplary nucleosides include ribonucleosides, deoxyribonucleosides, dideoxyribonucleosides, carbocyclic nucleosides, etc.

A "nucleotide" refers to an ester of a nucleoside, e.g., a phosphate ester of a nucleoside. To illustrate, a nucleotide can include 1, 2, 3, or more phosphate groups covalently linked to a sugar moiety of the nucleoside (e.g., at a 5' position, 3' position, 2' position, etc.).

A "nucleotide incorporating biocatalyst" refers to a catalyst that catalyzes the incorporation of nucleotides into a nucleic acid. Nucleotide incorporating biocatalysts are typically enzymes. An "enzyme" is a protein- and/or nucleic acid-based catalyst that acts to reduce the activation energy of a chemical reaction involving other compounds or "substrates." A "nucleotide incorporating enzyme" refers to an enzyme that catalyzes the incorporation of nucleotides into a nucleic acid, e.g., during nucleic acid amplification or the like. Exemplary nucleotide incorporating enzymes include, e.g., polymerases, terminal transferases, reverse transcriptases, telomerases, polynucleotide phosphorylases, and the like. A "thermostable enzyme" refers to an enzyme that is stable to heat, is heat resistant, and retains sufficient catalytic activity when subjected to elevated temperatures for selected periods of time. For example, a thermostable polymerase retains sufficient activity to effect subsequent primer extension reactions when subjected to elevated temperatures for the time necessary to effect denaturation of double-stranded nucleic acids. Heating conditions necessary for nucleic acid denaturation are well known to persons skilled in the art and are exemplified in U.S. Pat. No. 4,683,202, entitled "PROCESS FOR AMPLIFYING NUCLEIC ACID SEQUENCES," issued Jul. 28, 1987 to Mullis and U.S. Pat. No. 4,683,195, entitled "PROCESS FOR AMPLIFYING, DETECTING, AND/OR-CLONING NUCLEIC ACID SEQUENCES," issued Jul. 28, 1987 to Mullis et al., which are both incorporated by reference. To further illustrate, a "thermostable polymerase" refers to an enzyme that is suitable for use in a temperature cycling reaction, such as a polymerase chain reaction ("PCR"). For a thermostable polymerase, enzymatic activity refers to the catalysis of the combination of the nucleotides in the proper manner to form primer extension products that are complementary to a template nucleic acid.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Typically, the nucleotide monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., H$^+$, NH$_4^+$, Na$^+$, and the like, if such counterions are present. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetrahedron Lett.* 22:1859-1862; the triester method of Matteucci et al. (1981) *J. Am. Chem. Soc.* 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "phosphoramidite" refers to a compound that includes a group comprising the formula:

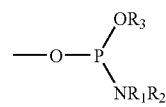

where R$_1$ and R$_2$ are alkyl groups independently selected from the group consisting of: methyl, ethyl, propyl, isopropyl, butyl, pentyl, hexyl, heptyl, octyl, nonyl, and heptyl; and R$_3$ is (CH$_2$)$_2$CN or CH$_3$. In certain embodiments, for example, a phosphoramidite is a nucleoside-3'-phosphoramidite monomer or a nucleoside-2'-phosphoramidite monomer, commonly used in oligonucleotide synthesis procedures. In some of these embodiments, these phosphoramidite monomers are protected at the 5' hydroxyl position with a protecting group. Different protecting groups are also typically attached to the exocyclic amines of the bases. In addition, the phosphorous atom of the monomer is optionally protected with beta-cyanoethyl (R$_3$) and diisopropylamine (NR$_1$R$_2$) groups or other groups that are consistent with the formula shown above. Phosphoramidites and oligonucleotide synthesis are also described in, e.g., Beaucage et al. (1992) "Advances in the synthesis of oligonucleotides by the phosphoramidite approach," *Tetrahedron* 48:2223-2311, which is incorporated by reference.

A "protecting group" refers to a chemical group that is covalently or non-covalently attached (e.g., removably attached) to a given compound and which prevents undesired chemical reactions from occurring at one or more sites in the compound. Exemplary protecting groups include trityl, monomethoxytrityl, dimethoxytrityl, levulinyl, fluorenylmethoxycarbonyl, benzhydryloxycarbonyl, and the like.

The term "pyrophosphorolysis" refers to the removal of one or more nucleotides from a nucleic acid in the presence of pyrophosphate (PP$_i$) to generate one or more nucleoside triphosphates.

A "quencher moiety" or "quencher" refers to a moiety that is capable of reducing the detectable emission of radiation, e.g., fluorescent or luminescent radiation, from a source that would otherwise have emitted this radiation. A quencher typically reduces the detectable radiation emitted by the source by at least 50%, typically by at least 80%, and more typically by at least 90%. Certain quenchers may re-emit the energy absorbed from, e.g., a fluorescent dye in a signal characteristic for that quencher and thus, a quencher can also be an acceptor moiety. This phenomenon is generally known as fluorescent resonance energy transfer or FRET. Alternatively, a quencher may dissipate the energy absorbed from a fluorescent dye in a form other than light, such as heat. Molecules commonly used in FRET applications include, for example, fluorescein, FAM, JOE, rhodamine, R6G, TAMRA, ROX, DABCYL, and EDANS. Whether a fluorescent dye is an acceptor or a quencher is defined by its excitation and emission spectra, and the fluorescent dye with which it is paired. For example, FAM is most efficiently excited by light with a wavelength of 488 nm, and emits light with a spectrum of 500 to 650 nm, and an emission maximum of 525 nm. FAM is a suitable donor moiety for use with, e.g., TAMRA as a quencher, which has at its excitation maximum 514 nm. Exemplary non-fluorescent or dark quenchers that dissipate energy absorbed from a fluorescent dye include the Black Hole Quenchers™ marketed by Biosearch Technologies, Inc. (Novato, Calif., USA). The Black Hole Quenchers™ are structures comprising at least three radicals selected from substituted or unsubstituted aryl or heteroaryl compounds, or combinations thereof, in which at least two of the residues are linked via an exocyclic diazo bond (see, e.g., International Publication No. WO 01/86001, entitled "DARK QUENCHERS FOR DONOR-ACCEPTOR ENERGY TRANSFER," published Nov. 15, 2001 by Cook et al., which is incorporated by reference). Exemplary quenchers are also provided in, e.g., U.S. Pat. No. 6,465,175, entitled "OLIGONUCLEOTIDE PROBES BEARING QUENCHABLE FLUORESCENT LABELS, AND METHODS OF USE THEREOF," which issued Oct. 15, 2002 to Horn et al., which is incorporated by reference.

A "silyl group" refers to a class of compounds that includes the general formula $SiRR_1R_2$, where R, $R_1$, and $R_2$ are independently an H, an alkyl group, an alkenyl group, an alkynyl group, an aryl group, or a combination of such groups.

A "solid support" refers to a solid material that can be derivatized with, or otherwise attached to, a chemical moiety, such as an probe or the like. Exemplary solid supports include plates, beads, microbeads, tubes, fibers, whiskers, combs, hybridization chips (including microarray substrates, such as those used in GeneChip® probe arrays (Affymetrix, Inc., Santa Clara, Calif., USA) and the like), membranes, single crystals, ceramic layers, self-assembling monolayers, and the like.

A "terminator nucleotide" refers to a nucleotide, which upon incorporation into a nucleic acid prevents further extension of the nucleic acid, e.g., by at least one nucleotide incorporating biocatalyst.

A "thioether group" refers to a linear, branched, or cyclic moiety that comprises two carbon atoms attached to a single sulfur atom and includes, e.g., methylthiomethyl, methylthioethyl, methylthiopropyl, and the like.

II. Overview

The invention relates to blocked oligonucleotides that are useful as probe and/or primer nucleic acids in various nucleic acid technologies. To illustrate, the blocked oligonucleotides described herein are readily substituted into many different PCR-related protocols without sacrificing ease of use and are economical alternatives to pre-existing blocked oligonucleotides. Some applications of these blocked oligonucleotides are further illustrated in the examples provided below and are also described in, e.g., entitled "2'-TERMINATOR RELATED PYROPHOSPHOROLYSIS ACTIVATED POLYMERIZATION", filed Oct. 18, 2006 by Gelfand et al. and entitled "MUTANT DNA POLYMERASES AND RELATED METHODS", filed Oct. 18, 2006 by Bauer et al., which are both incorporated by reference.

The blocked oligonucleotides and polynucleotides of the invention include 2'-terminator nucleotides, which render the oligonucleotides and polynucleotides non-extendible by various nucleotide incorporating biocatalysts. The 2'-terminator nucleotides of these oligonucleotides and polynucleotides typically have intact sugar rings or sugar analog rings (e.g., carbocyclic rings, etc.), and include blocking groups (e.g., negatively charged blocking groups, bulky blocking groups, and/or the like) at 2'-positions of these sugar moieties. In addition to methods of producing these oligonucleotides and polynucleotides, the invention also provides related business methods and kits. These and many other features of the present invention are described further below.

III. 2'-Terminator Nucleotides

The present invention relates to methods of producing oligonucleotides and polynucleotides that include 2'-terminator nucleotides. Oligonucletide synthesis and related nucleic acid synthesis reagents are described further below. The nucleotides and nucleosides utilized in the methods of the invention typically include a hydroxyl group at a 3'-position of an intact sugar ring and a blocking group (e.g., a negatively charged blocking group, a bulky blocking group, and/or the like) at a 2'-position of the sugar moiety. Certain nucleotide incorporating biocatalysts described herein comprise the ability to extend primer nucleic acids with these 2'-terminator nucleotides in a template directed manner. Upon incorporation of a 2'-terminator nucleotide at a 3'-terminal end of a primer nucleic acid, the nucleic acid is typically rendered non-extendible by the nucleotide incorporating biocatalyst. In addition, some nucleotide incorporating biocatalysts include the ability to remove 2'-terminator nucleotides from oligonucleotides and polynucleotides, e.g., via pyrophosphorolysis. Accordingly, the oligonucleotides of the invention are also optionally used as primer nucleic acids in various PAP applications. Certain applications of the blocked oligonucleotides of the invention as well as nucleotide incorporating biocatalysts useful in these applications also described in, e.g., entitled "2'-TERMINATOR RELATED PYROPHOSPHOROLYSIS ACTIVATED POLYMERIZATION", filed Oct. 18, 2006 by Gelfand et al. and entitled "MUTANT DNA POLYMERASES AND RELATED METHODS", filed Oct. 18, 2006 by Bauer et al., which are both incorporated by reference. Additional details relating to 2'-terminator nucleotides and nucleosides are provided in, e.g., U.S. patent application Ser. No. 10/879,493, entitled "2'-TERMINATOR NUCLEOTIDE-RELATED METHODS AND SYSTEMS," filed Jun. 28, 2004 by Gelfand et al., which is both incorporated by reference.

Nucleosides and nucleotides utilized in the methods and other aspects of the invention generally include the formula:

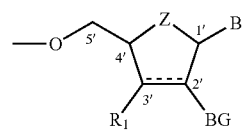

in which $R_1$ is H, OH, a hydrophilic group, or a hydrophobic group; B is at least one homocyclic ring, at least one heterocyclic ring (with or without exocyclic heteroatoms), at least one aryl group, or combinations thereof; BG is a blocking group; Z is O or $CH_2$; and ===== represents a single or double bond. In some embodiments, these nucleosides and nucleotides are labeled. Further, these 2'-terminator nucleotides generally comprise 1, 2, 3, or more phosphate groups attached at the 5' position. In one embodiment, for example, a 2'-terminator nucleotide comprises a 2'-monophosphate-3'-hydroxyl-5'-triphosphate nucleoside.

Figure 1B:
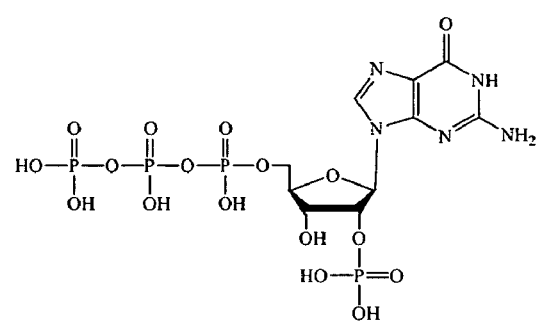
Figure 1C:
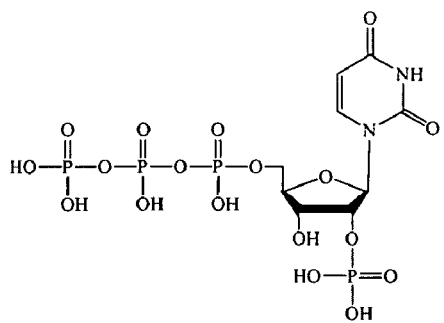
Figure 1D:
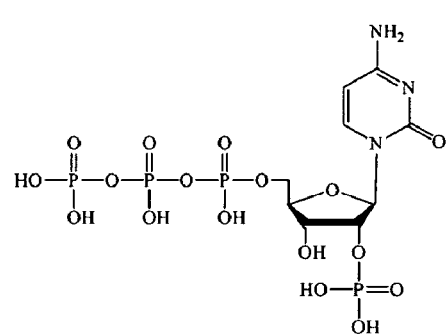

FIGS. 1A-D schematically illustrate certain embodiments of 2'-terminator nucleotides. In particular, FIG. 1A schematically shows an adenosine tetraphosphate terminator nucleotide, FIG. 1B schematically depicts a guanosine tetraphosphate terminator nucleotide, FIG. 1C schematically illustrates a uridine tetraphosphate terminator nucleotide, and FIG. 1D schematically shows a cytidine tetraphosphate terminator nucleotide.

A. Bases

Essentially any heterocyclic ring or aryl group (i.e., as the base or B group) that can base pair with another nucleic acid, e.g., via a hydrogen bond or through a base stacking mechanism is optionally included at the 1' position of the sugar moiety of a 2'-terminator nucleoside or nucleotide. Accordingly, no attempt is made herein to describe all of the possible groups that can be utilized. However, certain representative B groups are provided below for purposes of illustration. In some embodiments, for example, B comprises the formula:

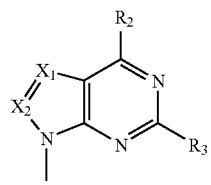

where $X_1$ and $X_2$ are independently selected from $CR_8$ and N; $R_2$ is H, OH, or $NR_4R_5$; $R_3$ is H, OH, or $NR_6R_7$; $R_4$, $R_5$, $R_6$, and $R_7$ are independently selected from H, an alkyl group, an alkenyl group, a benzyl group, an aryl group, an aryloxy group, and combinations thereof; and $R_8$ is H, a halo group, an alkyl group, an alkenyl group, an alkynyl group, an alkyl amine group, an alkenyl amine group, an alkynyl amine group, an alkyl alcohol group, an alkenyl alcohol group, an alkynyl alcohol group, unsubstituted polyethylene glycol, or substituted polyethylene glycol.

In other embodiments, B comprises the formula:

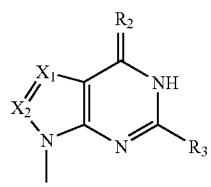

where $X_1$ and $X_2$ are independently selected from CH and N; $R_2$ is O or S; $R_3$ is H, OH, or $NR_4R_5$; and $R_4$ and $R_5$ are independently selected from H, an alkyl group, an alkenyl group, a benzyl group, an aryl group, and combinations thereof In some embodiments, B comprises the formula:

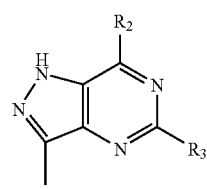

where $R_2$ is H, OH, or $NR_4R_5$; $R_3$ is H, OH, or $NR_6R_7$; and $R_4$, $R_5$, $R_6$, and $R_7$ are independently selected from H, an alkyl group, an alkenyl group, an alkynyl group, a benzyl group, an aryl group, and combinations thereof.

In some embodiments, B comprises the formula:

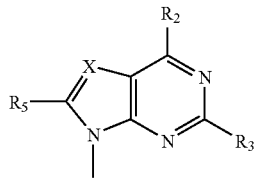

where X is CH or N; $R_2$ and $R_3$ are independently selected from H, OH, and $NHR_4$; $R_4$ is H, an alkyl group, an alkenyl group, a benzyl group, an aryl group, or combinations thereof; and, $R_5$ is OH, $NH_2$, SH, a halo group, an ether group, a thioether group, an alkyl group, an alkenyl group, an alkynyl group, an alkylamine group, an alkenylamine group, an alkynylamine group, or combinations thereof.

In other embodiments, B comprises the formula:

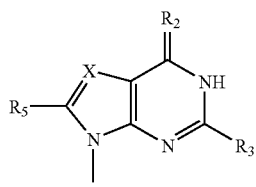

where X is CH or N; $R_2$ is O or S; $R_3$ is H, OH, or $NHR_4$; $R_4$ is H, an alkyl group, an alkenyl group, a benzyl group, an aryl group, or combinations thereof; and $R_5$ is OH, $NH_2$, SH, a halo group, an ether group, a thioether group, an alkyl group, an alkenyl group, an alkynyl group, an alkylamine group, an alkenylamine group, an alkynylamine group, or combinations thereof.

In certain embodiments, B comprises the formula:

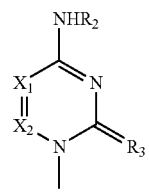

where $X_1$ and $X_2$ are independently selected from CH and N; $R_2$ is selected from H, an alkyl group, an alkenyl group, a benzyl group, an aryl group, an aryloxy group, or combinations thereof; and $R_3$ is O or S.

In other embodiments, B comprises the formula:

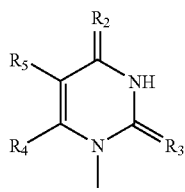

where $R_2$ and $R_3$ are independently selected from O and S; and $R_4$ and $R_5$ are independently selected from H, $NH_2$, SH, OH, an alkyl group, an alkenyl group, an alkynyl group, a benzyl group, an aryl group, an aryloxy group, an alkoxy group, a halo group, and combinations thereof.

In some embodiments, B comprises the formula:

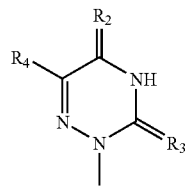

where $R_2$ and $R_3$ are independently selected from O and S; and $R_4$ is H, $NH_2$, SH, OH, an alkyl group, an alkenyl group, a benzyl group, an aryl group, an aryloxy group, an alkoxy group, a halo group, or combinations thereof.

In other embodiments, B comprises the formula:

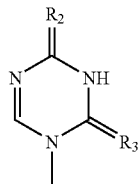

where $R_2$ and $R_3$ are independently selected from O and S.

In some embodiments, B comprises the formula:

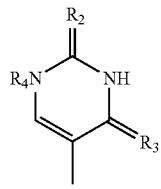

where $R_2$ and $R_3$ are independently selected from O and S, and $R_4$ is H, an alkyl group, an alkenyl group, or an alkynyl group.

In other embodiments, B comprises the formula:

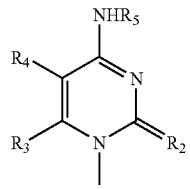

where $R_2$ is O or S; $R_3$ and $R_4$ are independently selected from H, $NH_2$, SH, OH, COOH, $COOCH_3$, $COOCH_2CH_3$, CHO, $NO_2$, CN, an alkyl group, an alkenyl group, an alkynyl group, a benzyl group, an aryl group, an aryloxy group, an alkoxy group, a halo group, and combinations thereof; and $R_5$ is an alkyl group, an alkenyl group, an aryl group, a benzyl group, or combinations thereof.

B. Blocking Groups

The blocking groups (BG) utilized at the 2' position of the sugar moiety also include various embodiments. In some embodiments, for example, BG is a negatively charged group and/or a bulky group. To further illustrate, BG is optionally selected from, e.g., CN, $NO_2$, $N_3$, a halo group, an ether group, an aldehyde group, a carboxylic acid group, an ester group, an amino group, $OCH_3$, $OCH_2COOH$, an O-silylether group, a keto group, an O-lactone group, an O-alkyl group, an O-cyclic alkyl group, an O-alkenyl group, an O-alkynl group, a carbamate group, an imide group, an amide group, and combinations thereof. More specifically, BG optionally comprises the formula:

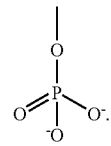

In other embodiments, BG comprises the formula:

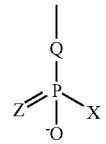

where Q is O, S, or NH; X is H, OH, $CH_3$, $BH_3$, F, or SeH; and Z is O, S, or Se. FIG. 2B schematically depicts one nucleotide comprising a blocking group having this formula. To further illustrate, BG optionally comprises the formula:

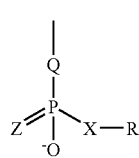

where Q is O, S, or NH; X is O, S, or NH; Z is O, S, or Se; and R is an alkyl group, an alkenyl group, or an alkynyl group. FIG. 2A schematically depicts one 2'-terminator nucleotide comprising a blocking group having this formula. In another exemplary embodiment, BG comprises the formula:

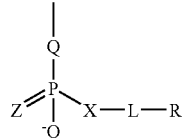

where Q is O, S, or NH; X is O, S, or NH; Z is O, S, or Se; L is —$CONH(CH_2)_nNH$—, —$CO(CH_2)_nNH$—, or —$CONH(CH_2CH_2O)_nCH_2CH_2NH$—; n is an integer greater than 0; and R is $NH_2$, SH, COOH, a quencher moiety, a reporter moiety, biotin, or a affinity moiety.

C. Labeling

The oligonucleotides and polynucleotides of the invention are optionally labeled following synthesis. In some embodiments, the nucleic acid synthesis reagents (e.g., phosphoramidite precursors of 2'-terminator nucleotides, phosphoramidite precursors of other nucleotides, oligonucleotides or polynucleotides comprising protecting groups, etc.) are labeled prior to synthesis of the oligonucleotides and polynucleotides. For example, a label is optionally attached, e.g., to a homocyclic ring, a heterocyclic ring, or an aryl group of a 2'-terminator nucleotide or other nucleotide (e.g., via $C^5$ of a pyrimidine, $N^4$ of cytidine, $C^7$ of a purine, $N^6$ of adenosine, $C^8$ of a purine, or another attachment site known in the art), e.g., through an amide, ester, thioester, ether, thioether, carbon-carbon, or other type of covalent bond. In addition, or alternatively, the label is attached to a sugar moiety (e.g., a ribose sugar, etc.), or an analog thereof (e.g., a carbocyclic ring, etc.), of a 2'-terminator nucleotide or other nucleotide (e.g., a dNTP or the like), and/or a phosphate group of a 2'-terminator nucleotide or other nucleotide, such as by a covalent bond that is an amide, ester, thioester, ether, thioether, carbon-carbon, or other bond. Covalent bonds are typically formed in reactions between electrophilic and nucleophilic groups of labels and nucleotides. In certain embodiments, labels and nucleotides are directly conjugated to one another (e.g., via single, double, triple or aromatic carbon-carbon bonds, or via carbon-nitrogen bonds, nitrogen-nitrogen bonds, carbon-oxygen bonds, carbon-sulfur bonds, phosphorous-oxygen bonds, phosphorous-nitrogen bonds, etc.). Optionally, a linker attaches the label to a 2'-terminator nucleotide or other nucleotide. A wide variety of linkers can be used or adapted for use in conjugating labels and nucleotides. Certain non-limiting illustrations of such linkers are referred to herein.

Figure 3A:
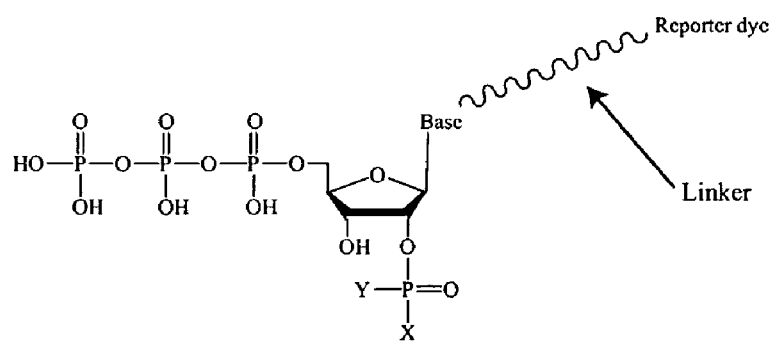
FIGS. 3A-C schematically illustrate dye labeled tetraphosphates according to various embodiments.
Figure 3B:
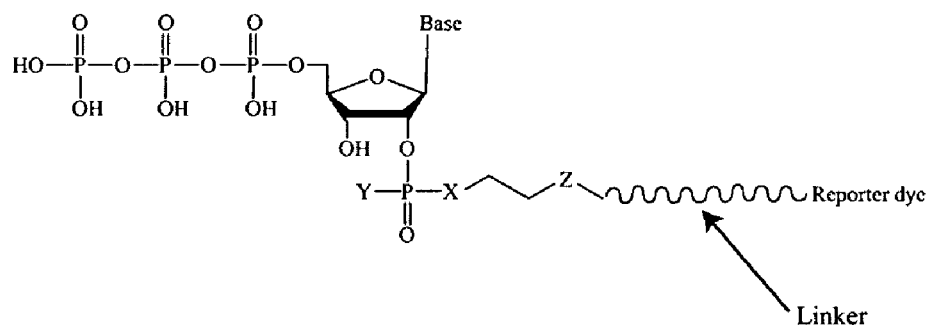
Figure 3C:
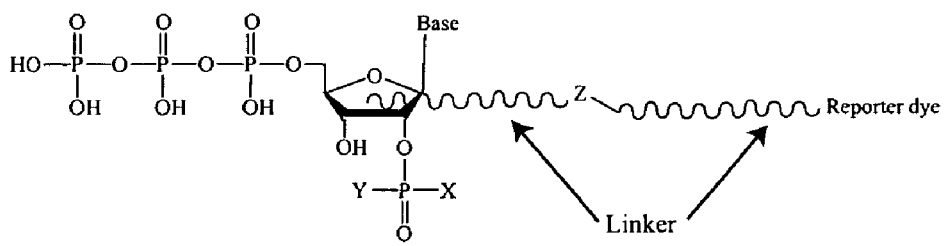
Figure 5:
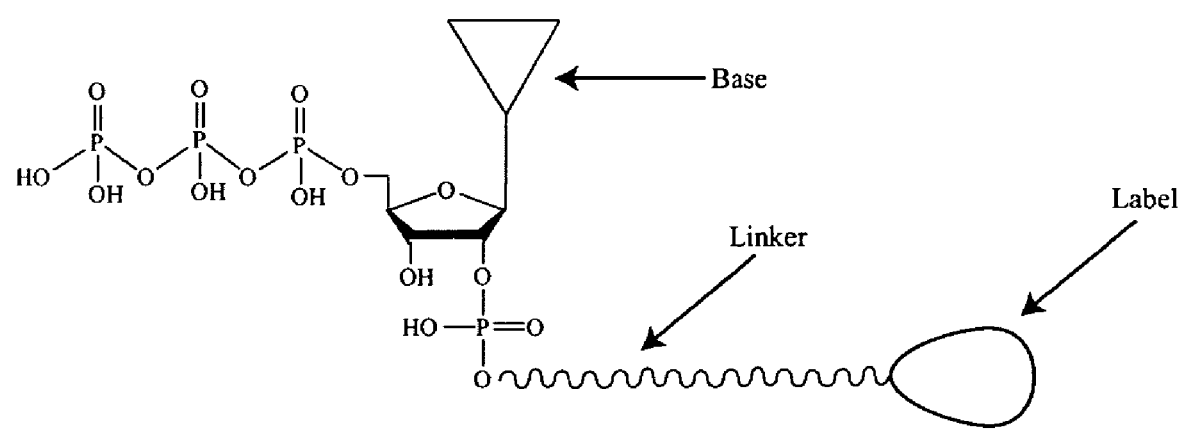
FIG. 5 schematically depicts a label attached to a nucleotide tetraphosphate via a linker.
Figure 6A:
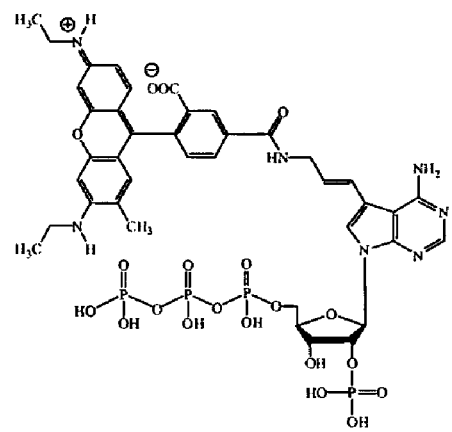
Figure 6B:
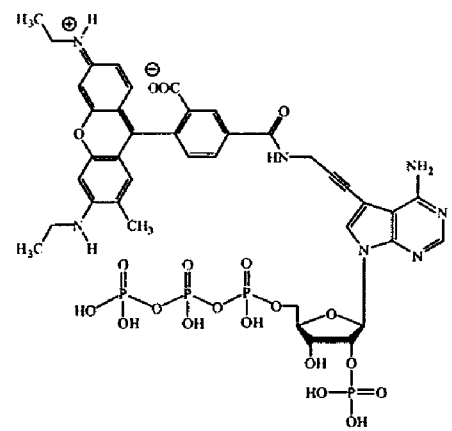
Figure 6C:
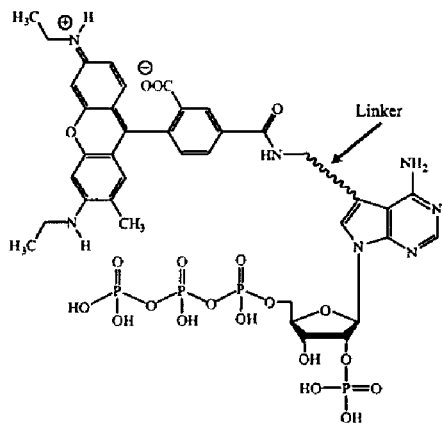
Figure 6D:
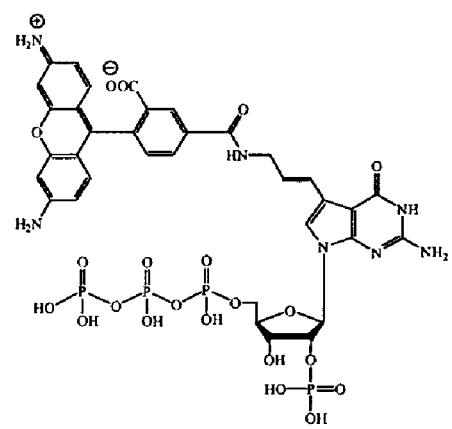
Figure 6E:
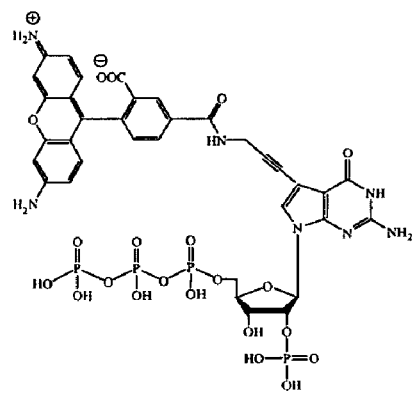
Figure 6F:
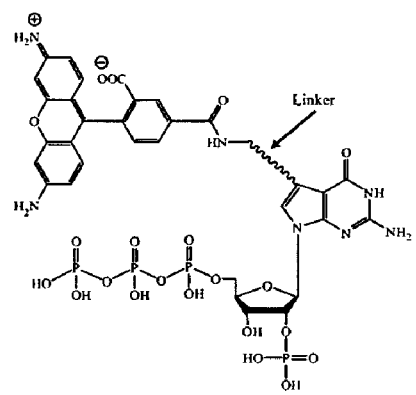
Figure 6G:
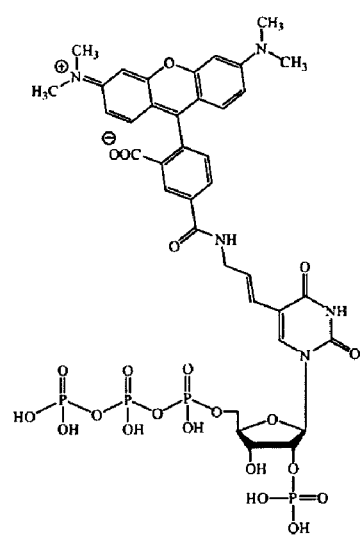
Figure 6H:
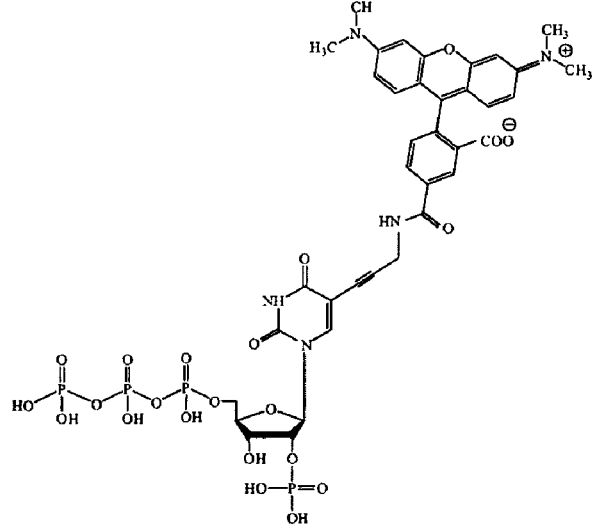
Figures 6I, 6J:
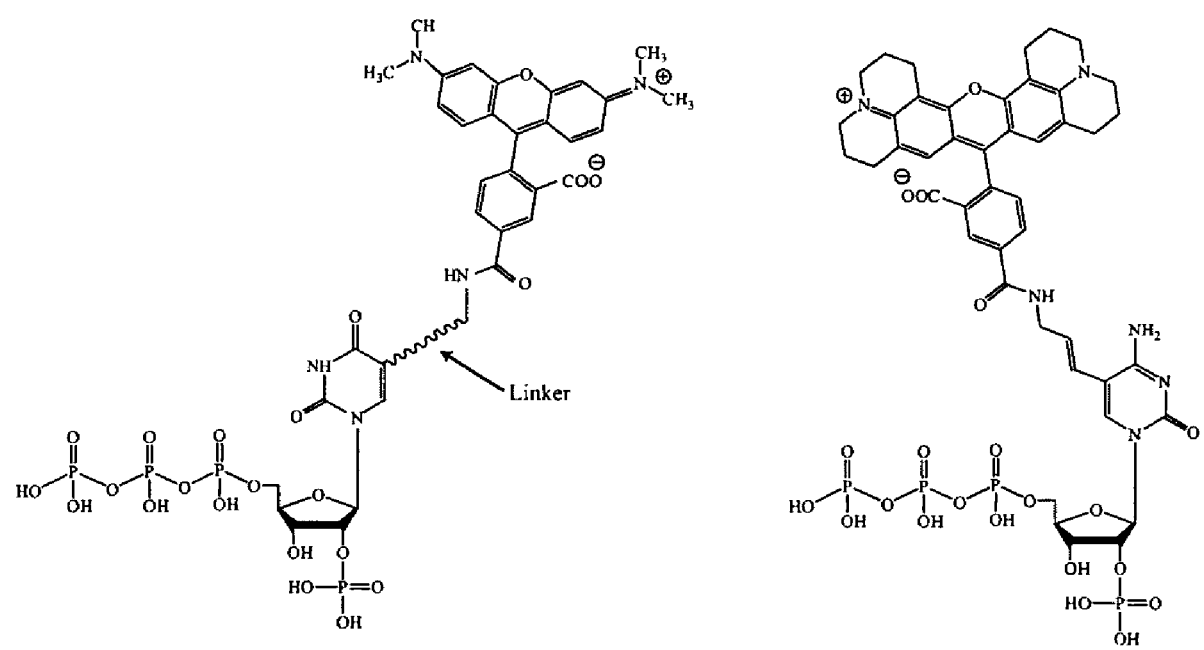

To further illustrate, FIGS. 3A-C schematically shows dye labeled tetraphosphates according to certain embodiments. In particular, FIG. 3A schematically shows a reporter dye attached to a base of a 2'-terminator nucleotide via a linker group, FIG. 3B schematically depicts a reporter dye attached to a blocking group of a 2'-terminator nucleotide via a linker group, and FIG. 3C schematically shows a reporter dye attached to a sugar moiety of a 2'-terminator nucleotide via a linker group, where X is H, OH, $NHR_1$, $SR_1$, an alkyl group, a benzyl group, an aryl group, an alkyl-aryl group, an alkenyl group, an alkynyl group, an alkoxy group, or the like (where $R_1$ is H, an alkyl group, a benzyl group, an aryl group, an alkyl-aryl group, an alkenyl group, an alkynyl group, or the like), or comprises O, S, N, C, or the like, Y is $OR_2$, $SR_2$, $NHR_2$, or the like (where $R_2$ is H, an alkyl group, an alkenyl group, an alkynyl group, an aryl group, an alkyl-aryl group, or the like), and Z comprises O, S, N, C, Si, or the like. FIGS. 4A and B also schematically show some embodiments of labeled nucleoside tetraphosphates. More specifically, FIGS. 4A and B schematically show labels attached via linkers to bases of the nucleoside tetraphosphates, where R is selected from, e.g., H, OH, an alkyl group, an aryl group, an alkyl-aryl group, an alkenyl group, an alkynyl group, and the like. In addition, FIG. 5 schematically depicts a label attached to a phosphate group of a nucleoside tetraphosphate via a linker. FIGS. 6A-L also schematically show various 2'-terminator nucleotides having fluorescent dyes attached to the bases of the nucleotides according to certain embodiments. In particular, FIGS. 6A-C schematically show R6G-labeled adenosine tetraphosphates, FIGS. 6D-F schematically depict R110-labeled guanosine tetraphosphates, FIG. 6G-I schematically illustrate TAMRA-labeled uridine tetraphosphates, and FIGS. 6J-L schematically show ROX-labeled cytidine tetraphosphates. Of course, labels may be attached to 2'-terminator nucleotides or other nucleotides at other locations, as described herein, including via linkers. To illustrate, FIG. 7 schematically depicts one embodiment of a linker. In some embodiments, for example, the 2'-terminator nucleotides of FIGS. 6C, 6F, 6I, and 6L include the linker of FIG. 7.

Essentially any label is optionally utilized to label the nucleotides and nucleosides utilized in the oligonucletides of the invention. In some embodiments, for example, the label comprises a fluorescent dye (e.g., a rhodamine dye (e.g., R6G, R110, TAMRA, ROX, etc.), a fluorescein dye (e.g., JOE, VIC, TET, HEX, FAM, etc.), a halofluorescein dye, a cyanine dye (e.g., CY3, CY3.5, CY5, CY5.5, etc.), a BODIPY® dye (e.g., FL, 530/550, TR, TMR, etc.), an ALEXA FLUOR® dye (e.g., 488, 532, 546, 568, 594, 555, 653, 647, 660, 680, etc.), a dichlororhodamine dye, an energy transfer dye (e.g., BIGDYE™ v 1 dyes, BIGDYE™ v 2 dyes, BIGDYE™ v 3 dyes, etc.), Lucifer dyes (e.g., Lucifer yellow, etc.), CASCADE BLUE®, Oregon Green, and the like. Additional details relating to fluorescent dyes are provided in, e.g., Haugland, *Molecular Probes Handbook of Fluorescent Probes and Research Products*, Ninth Ed. (2003) and the updates thereto, which are each incorporated by reference. Fluorescent dyes are generally readily available from various commercial suppliers including, e.g., Molecular Probes, Inc. (Eugene, Oreg.), Amersham Biosciences Corp. (Piscataway, N.J.), Applied Biosystems (Foster City, Calif.), etc. Other labels include, e.g., biotin, weakly fluorescent labels (Yin et al. (2003) *Appl Environ Microbiol.* 69(7):3938, Babendure et al. (2003) *Anal. Biochem.* 317(1):1, and Jankowiak et al. (2003) *Chem Res Toxicol.* 16(3):304), non-fluorescent labels, colorimetric labels, chemiluminescent labels (Wilson et al. (2003) *Analyst.* 128(5):480 and Roda et al. (2003) *Luminescence* 18(2):72), Raman labels, electrochemical labels, bioluminescent labels (Kitayama et al. (2003) *Photochem Photobiol.* 77(3):333, Arakawa et al. (2003) *Anal. Biochem.* 314(2): 206, and Maeda (2003) *J. Pharm. Biomed. Anal.* 30(6):1725), and an alpha-methyl-PEG labeling reagent as described in, e.g., U.S. Provisional Patent Application No. 60/428,484, filed on Nov. 22, 2002, which references are each incorporated by reference.

In certain embodiments, the label comprises a radioisotope, such as $^3H$, $^{14}C$, $^{22}Na$, $^{32}P$, $^{33}P$, $^{35}S$, $^{42}K$, $^{45}Ca$, $^{59}Fe$, $^{125}I$, $^{203}Hg$, or the like. To further exemplify, the label also optionally includes at least one mass-modifying group. For example, the mass-modifying group is optionally selected from, e.g., deuterium, F, Cl, Br, I, S, $N_3$, XY, $CH_3$, $SPO_4$, $BH_3$, $SiY_3$, $Si(CH_3)_3$, $Si(CH_3)_2(C_2H_5)$, $Si(CH_3)(C_2H_5)_2$, $Si(C_2H_5)_3$, $(CH_2)_nCH_3$, $(CH_2)_nNY_2$, $CH_2CONY_2$, $(CH_2)_nOH$, $CH_2F$, $CHF_2$, $CF_3$, and a phosphorothioate group, where X is O, NH, NY, S, NHC(S), $OCO(CH)_nCOO$, NHCO$(CH_2)_nCOO$, $OSO_2O$, $OCO(CH_2)_n$, NHC(S)NH, OCO$(CH_2)_nS$, $OCO(CH_2)S$, $NC_4O_2H_5S$, OPO(O-alkyl), or OP(O-alkyl); n is an integer from 1 to 20 inclusive; and, Y is H, deuterium, an alkyl group, an alkoxy group, an aryl group, a polyoxymethylene group, a monoalkylated polyoxymethylene group, a polyethylene imine group, a polyamide group, a polyester group, a alkylated silyl group, a heterooligo, a polyaminoacid, a heterooligo/polyaminoacid group, or a polyethylene glycol group. Additional details relating to nucleic acid labeling and sequence analysis are provided in, e.g., Sterky et al. (2000) "Sequence analysis of genes and genomes," *J. Biotech.* 76(2000): 1, Sensen (Ed.) *Biotechnology, Volume 5B, Genomics and Bioinformatics*, John Wiley & Sons, Inc. (2001), and Sensen (Ed.) *Essentials of Genomics and Bioinformatics*, John Wiley & Sons, Inc. (2002), which are each incorporated by reference.

A large variety of linkers are available for linking labels to nucleic acids and will be apparent to one of skill in the art. A linker is generally of a structure that is sterically and electronically suitable for incorporation into a nucleic acid. Linkers optionally include, e.g., ether, thioether, carboxamide, sulfonamide, urea, urethane, hydrazine, or other moieties. To further illustrate, linkers generally include between about one and about 25 nonhydrogen atoms selected from, e.g., C, N, O, P, Si, S, etc., and comprise essentially any combination of, e.g., ether, thioether, amine, ester, carboxamide, sulfonamide, hydrazide bonds and aromatic or heteroaromatic bonds. In some embodiments, for example, a linker comprises a combination of single carbon-carbon bonds and carboxamide or thioether bonds. Although longer linear segments of linkers are optionally utilized, the longest linear segment typically contains between about three to about 15 nonhydrogen atoms, including one or more heteroatoms.

Nonlimiting examples of linker moieties include substituted (e.g., functionalized) or unsubstituted groups, such as polyethylene glycol (PEG), polymethylene groups, arylene groups, alkylarylene groups, arylenealkyl groups, arylthio groups, amido alkyl groups, alkynyl alkyl groups, alkenyl alkyl groups, alkyl groups, alkoxyl groups, thio groups, amino alkyl groups, morpholine derivatized phosphates, peptide nucleic acids (e.g., N-(2-aminoethyl)glycine, etc.), and the like. Certain of these and other linkers are described further in, e.g., U.S. Pat. No. 6,339,392 to Haugland et al., U.S. Pat. No. 5,047,519 to Hobbs, Jr. et al., U.S. Pat. No. 4,711,958 to Iizuka et al., U.S. Pat. No. 5,175,269 to Stavrianopoulos, U.S. Pat. No. 4,711,955 to Ward et al., U.S. Pat. No. 5,241,060 to Engelhardt et al., U.S. Pat. No. 5,328,824 to Ward et al., and U.S. Pat. Publication No. 2002/0151711 by Khan et al., which are each incorporated by reference. Additional details relating to nucleic acid labeling and linkers are provided in, e.g., Hermanson, *Bioconjugate Techniques*, Elsevier Science (1996), which is incorporated by reference. In certain embodiments, suitable linkers comprise photocleavable moieties, such as 2-nitrobenzyl moieties, alpha-substituted 2-nitrobenzyl moieties (e.g., 1-(2-nitrophenyl) ethyl moieties), 3,5-dimethoxybenzyl moieties, thiohydroxamic acid, 7-nitroindoline moieties, 9-phenylxanthyl moieties, benzoin moieties, hydroxyphenacyl moieties, NHS-ASA moieties, and the like. Photocleavable linkers are described further in, e.g., U.S. Pat. Publication No. 2003/0099972 by Olejnik et al., which is incorporated by reference. In some embodiments, linkers include metals, such as platinum atoms. These are described further in, e.g., U.S. Pat. No. 5,714,327 to Houthoff et al., which is incorporated by reference. A number of linkers of varying lengths are commercially available from various suppliers including, e.g., Qiagen-Operon Technologies, Inc. (Alameda, Calif., USA), BD Biosciences Clontech (Palo Alto, Calif., USA), and Molecular BioSciences (Boulder, Colo., USA).

IV. Synthesis of 2'-Terminator Nucleosides or Nucleotides

The 2'-terminator nucleosides and nucleotides included in the oligonucleotides of the invention can be synthesized using various methods. For example, one method of producing a labeled, non-extendible nucleotide includes attaching at least one phosphate group to a 5'-position of a sugar moiety of a nucleoside (e.g., a ribonucleoside, a carbocyclic nucleoside, etc.), and attaching at least one blocking group to a 2'-position of the sugar moiety of the nucleoside. Exemplary blocking groups and bases that are optionally included in the nucleosides utilized in this method are described herein. The method also includes attaching at least one label to the sugar moiety, the blocking group, and/or a base of the nucleoside. Suitable labels are described further above and in certain examples provided below.

To further illustrate, one method of producing a 2'-monophosphate nucleoside that is optionally utilized includes reacting a nucleotide comprising the formula:

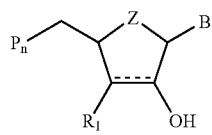

where P is at least one phosphate group; n is an integer greater than 0; $R_1$ is H, OH, a hydrophilic group, or a hydrophobic group; B is at least one homocyclic ring, at least one heterocyclic ring, at least one aryl group, or combinations thereof; Z is O or $CH_2$; and ==== represents a single or double bond; with trisodium trimetaphosphate $(NaPO_3)_3$ under conditions effective to produce the 2'-monophosphate nucleoside. In certain embodiments, for example, the nucleotide comprises two phosphate groups, whereas in others, the nucleotide comprises three phosphate or more groups. Effective conditions to produce the nucleotide generally include performing the reactions in solution at an alkaline pH. For example, the synthesis is typically performed at a pH greater than about 8.0, more typically at a pH greater than about 10.0, and still more typically at a pH greater than about 12.0 (e.g., at about 12.5, 13.0, 13.5, or 14.0). Various basic compounds can be used to adjust the pH of the reaction mixture including, e.g., KOH and NaOH among many others that are widely known in the art. The nucleotide is typically the limiting reagent. Although other temperature conditions are optionally utilized, these synthesis reactions are generally performed at or near room temperature (i.e., between about 20° C. and about 30° C., e.g., at about 23° C., 24° C., 25° C., 26° C., etc.). In addition, these reactions are generally allowed to proceed for at least about 4 hours, typically for at least about 6 hours, and even more typically for at least about 16 hours.

Figure 8:
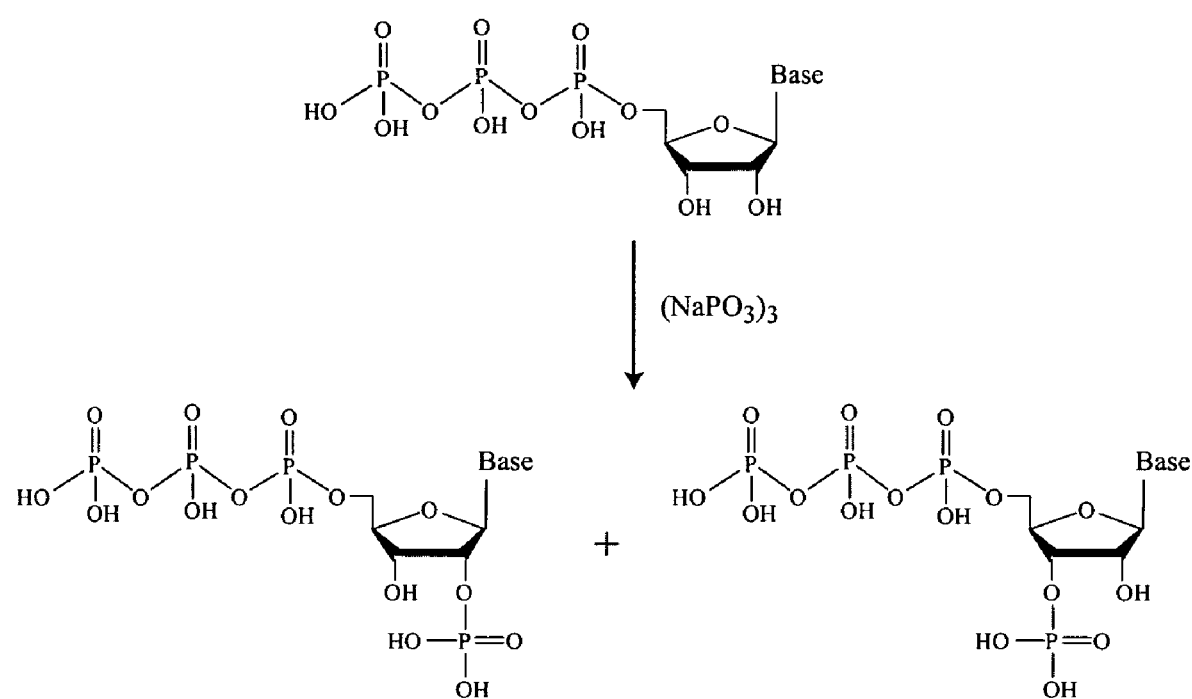
FIG. 8 schematically illustrates a synthetic reaction that produces a mixture of 5'-triphosphate-3'-monophosphate nucleotides and 5'-triphosphate-2'-monophosphate nucleotides.

In addition, FIG. 8 schematically illustrates a synthetic reaction that produces a mixture of 5'-triphosphate-3'-monophosphate nucleosides and 5'-triphosphate-2'-monophosphate nucleosides (e.g., in molar ratios of about 50:50). The synthesis of a mixture of purine nucleotides is provided below in an example. Specific or at least selective synthesis pathways are also described herein. In embodiments where a mixture of nucleotides is produced, the methods typically further include separating the 5'-triphosphate-2'-monophosphate nucleosides from the 5'-triphosphate-3'-monophosphate nucleosides. A variety of separation techniques can be utilized to separate 5'-triphosphate-2'-monophosphate nucleosides from other compounds or impurities including liquid chromatography. Various separation techniques that are useful in purifying nucleotide synthesis products are described further in, e.g., Skoog et al., *Principles of Instrumental Analysis*, 5$^{th}$ Ed., Harcourt Brace College Publishers (1998) and Currell, *Analytical Instrumentation: Performance Characteristics and Quality*, John Wiley & Sons, Inc. (2000), which are both incorporated by reference.

As mentioned above, various regiospecific or at least regioselective synthetic pathways can also be utilized such that product purification is generally minimized, if not entirely eliminated. These synthetic pathways, which typically include the use of various protecting groups (e.g., t-Butyldimethylsiloxy (TBDMS), $SiR_1R_2R_3$ (where $R_1$, $R_2$, and $R_3$ are independently selected from alkyl groups), triisopropylsilyloxymethyl (TOM), etc.) at the 3'-position of sugar moieties, are described further below.

Figure 9:
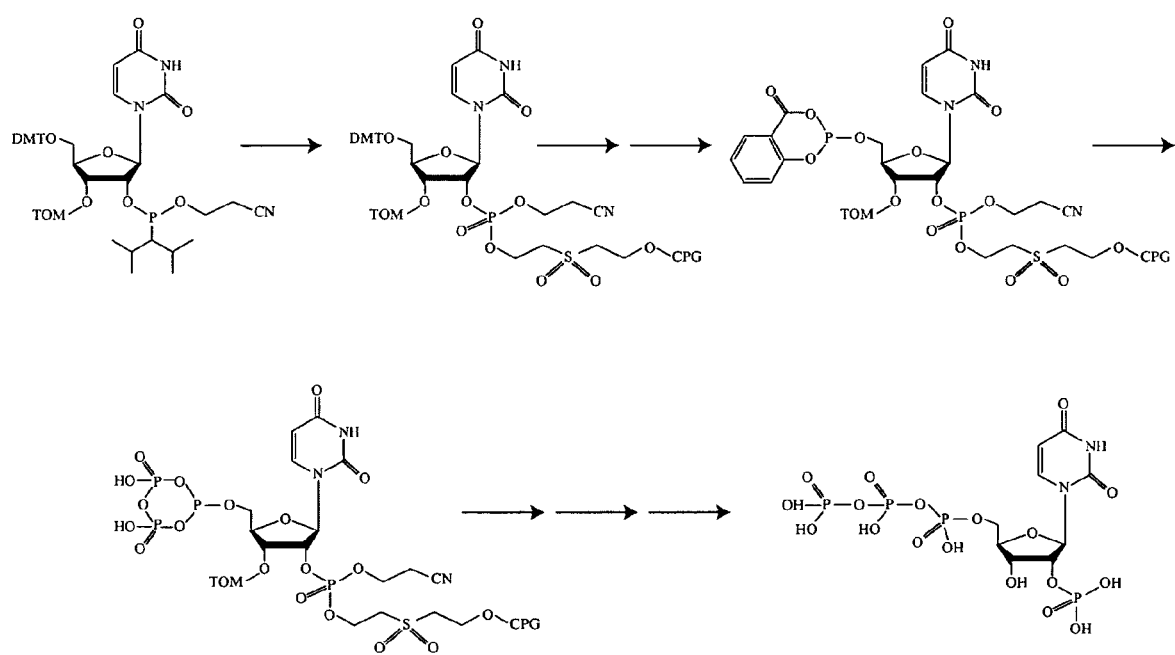
FIG. 9 schematically depicts certain steps in a solid phase synthesis pathway for a uridine tetraphosphate according to one embodiment.
Figure 10:
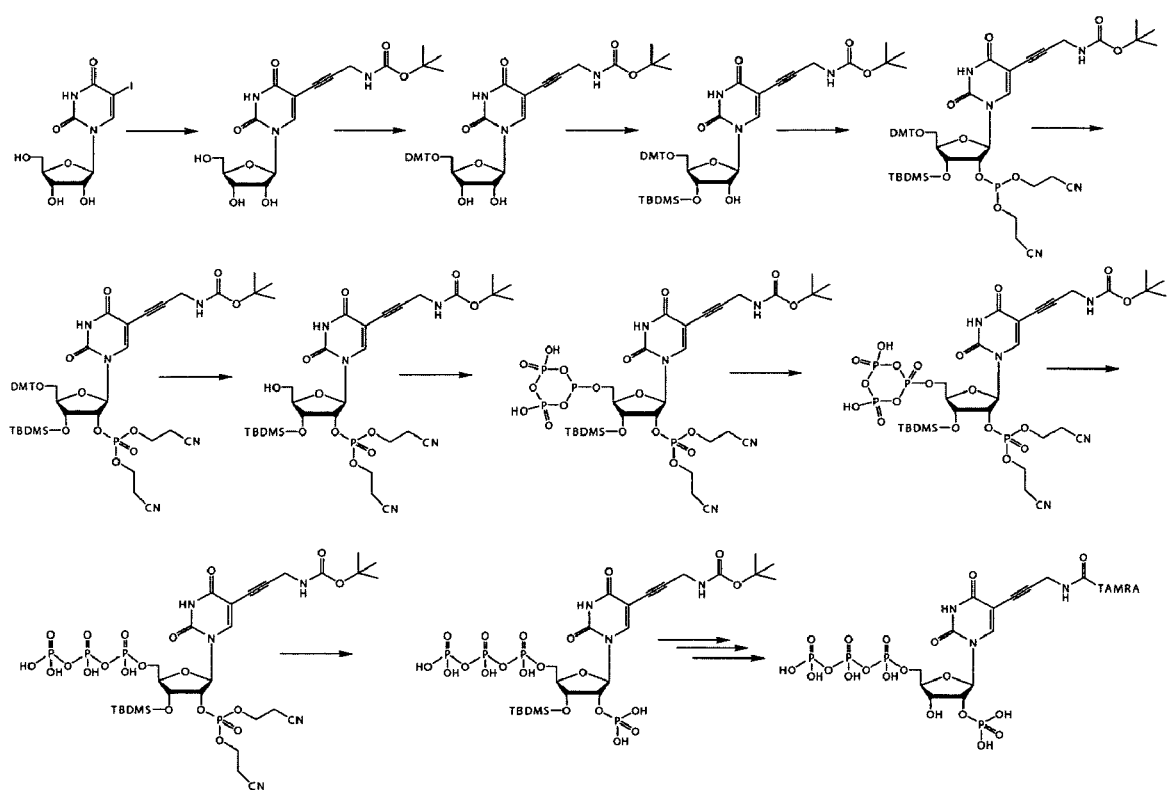
FIG. 10 schematically shows certain steps in an exemplary regiospecific synthesis pathway for TAMRA-uridine tetraphosphate.

The synthetic pathways of the invention are further illustrated in, e.g., FIG. 9, which schematically depicts certain steps in a solid phase synthesis pathway for a uridine tetraphosphate. In addition, FIG. 10 schematically shows certain steps in a regiospecific synthesis pathway for TAMRA-uridine tetraphosphate according to one embodiment. Additional synthetic pathways and other aspects related to the production of 2'-terminator nucleotides are provided in the examples below.

Various synthetic techniques that can be adapted for use in the synthesis protocols of the present invention are generally known and described in, e.g., March, *Advanced Organic Chemistry: Reactions, Mechanisms, and Structure*, 4$^{th}$ Ed., John Wiley & Sons, Inc. (1992), and Carey and Sundberg, *Advanced Organic Chemistry Part A: Structure and Mechanism*, 4th Ed., Plenum Press (2000), which are each incorporated by reference. Chemical starting materials and other reaction components useful in the synthesis of the nucleotides of the present invention are readily available from various commercial suppliers including, e.g., Sigma-Aldrich, Inc. (St Louis, Mo.).

V. Synthesis of Blocked Oligonucleotides and Polynucleotides Comprising 2'-Terminator Nucleotides The synthesis of blocked oligonucleotides and polynucleotides that include 2'-terminator nucleotides can be accomplished using various types of nucleic acid synthesis reagents. To illustrate, oligonucleotides may be synthesized enzymatically, e.g., using a nucleotide incorporating biocatalyst (e.g., a DNA polymerase, a ligase, etc.) or by chemical synthesis, e.g., using a phosphoramidite method or a phosphite-triester method (Herdewijn, *Oligonucleotide Synthesis: Methods and Applications*, Humana Press (2005), Gait (Ed.), *Oligonucleotide Synthesis*, Oxford University Press (1984), Vorbruggen et al., *Handbook of Nucleoside Synthesis* John Wiley & Sons, Inc. (2001), and Hermanson, *Bioconjugate Techniques*, Elsevier Science (1996), which are each incorporated by reference). Labels can be introduced during enzymatic synthesis utilizing, e.g., labeled nucleoside triphosphate monomers (e.g., labeled extendible nucleotides, labeled 2'-terminator nucleotides, etc.), or introduced during chemical synthesis using labeled non-nucleotide or nucleotide phosphoramidites, or may be introduced subsequent to synthesis.

An exemplary procedure for enzymatically synthesizing labeled oligonucleotides includes denaturing a template or target nucleic acid and annealing a pair of primers to the template. In some embodiments, a mixture of deoxynucleoside triphosphates (e.g., dGTP, dATP, dCTP, and dTTP) is added to the reaction mixture in which at least a fraction of one of the deoxynucleotides is labeled as described herein. Next, a nucleotide incorporating catalyst, such as a DNA polymerase enzyme is generally added to the reaction mixture under conditions in which the enzyme is active. A labeled oligonucleotide is formed by the incorporation of the labeled deoxynucleotides during polymerase strand synthesis. The DNA polymerase utilized in this method is generally thermostable, and the reaction temperature is typically cycled between denaturation and extension temperatures to effect the synthesis of labeled complementary strands of the target nucleic acid by PCR (Edwards et al. (Eds.), *Real-Time PCR: An Essential Guide*, Horizon Scientific Press (2004), Innis et al. (Eds.), *PCR Strategies*, Elsevier Science & Technology Books (1995), and Innis et al. (Eds.), *PCR Protocols*, Academic Press (1990), which are each incorporated by reference. Thereafter, the desired amplicon is separated from other components of the reaction mixture using various purification techniques known to persons of skill in the art. The amplicon can then be denatured and annealed to the template nucleic acid under conditions in which 2'-terminator nucleotides are incorporated at the 3' ends of the individual amplicon strands to produce the desired blocked oligonucleotides. Alternatively, oligonucleotides (synthesized enzymatically or chemically) comprising 2'-terminator nucleotides can be ligated to the amplicon strands to produce the desired blocked oligonucleotides. Other variations of these enzymatic approaches to blocked oligonucleotide synthesis will be apparent to persons of skill in the art.

Blocked oligonucleotides and polynucleotides made using chemical synthesis are generally produced using a phosphoramidite method, although other approaches are also optionally utilized. Phosphoramidite-based synthesis is commonly performed with growing oligonucleotide chains attached to solid supports, so that excess reagents, which are in the liquid phase, can be easily removed by filtration. This eliminates the need for other purification steps between cycles.

Figure 23:
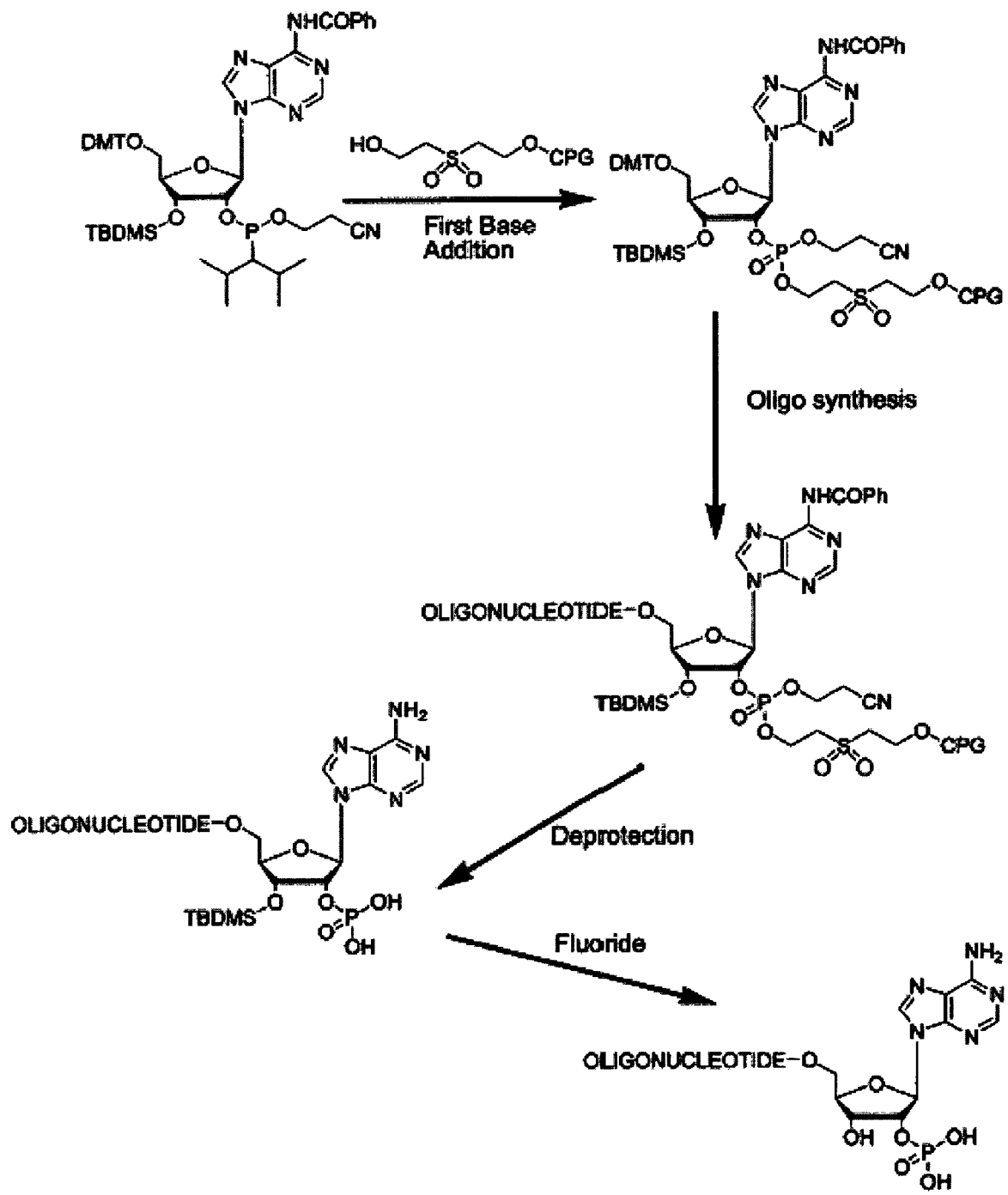
FIG. 23 schematically depicts an exemplary blocked oligonucleotide synthesis pathway.

To briefly describe an exemplary solid-phase oligonucleotide synthesis cycle that utilizes a phosphoramidite method, a solid support including a protected nucleotide monomer is typically initially treated with acid (e.g., trichloroacetic acid) to remove a 5'-hydroxyl protecting group, freeing the hydroxyl for a subsequent coupling reaction. An activated intermediate is then generally formed by simultaneously adding a protected nucleoside phosphoramidite monomer and a weak acid (e.g., tetrazole) to the reaction. The weak acid protonates the nitrogen of the phosphoramidite forming a reactive intermediate. Nucleotide addition to the growing nucleic acid chain is generally completed within 30 seconds. Thereafter, a capping step is typically performed to terminate any oligonucleotide chains that did not undergo nucleotide addition. Capping can be performed with, e.g., acetic anhydride, 1-methylimidazole, or the like. The internucleotide linkage is then converted from the phosphite to the more stable phosphotriester by oxidation using, e.g., iodine as an oxidizing agent and water as the oxygen donor. Following oxidation, the hydroxyl protecting group is typically removed with a protic acid (e.g., trichloroacetic acid or dichloroacetic acid) and the cycle is repeated until chain elongation is complete. After synthesis, the synthesized oligonucleotide is generally cleaved from the solid support using a base, such as ammonium hydroxide, or t-butyl amine. The cleavage reaction also removes any phosphate protecting groups (e.g., cyanoethyl). Finally, protecting groups on exocyclic amines of the bases and hydroxyl protecting groups on the labeling moiety or moieties are removed by treating the oligonucleotide solution under basic conditions at an elevated temperature (e.g., up to about 55° C.). An exemplary phosphoramidite-based synthesis pathway is also schematically illustrated in FIG. 23. The synthesis of blocked oligonucleotides is further illustrated in the examples provided below.

Descriptions of the chemistry used to form oligonucleotides by phosphoramidite methods are also provided in, e.g., U.S. Pat. No. 4,458,066, entitled "PROCESS FOR PREPARING POLYNUCLEOTIDES," issued Jul. 3, 1984 to Caruthers et al., and U.S. Pat. No. 4,415,732, entitled "PHOSPHORAMIDITE COMPOUNDS AND PROCESSES," issued Nov. 15, 1983 to Caruthers et al., which are both incorporated by reference.

Any of the nucleoside phosphoramidite monomers may be labeled as desired. In certain embodiments, if the 5'-terminus of the oligonucleotide is to be labeled, a labeled nucleoside or non-nucleotidic phosphoramidite may be used during the final condensation step. If an internal position of the oligonucleotide is to be labeled, a labeled nucleotidic phosphoramidite can be used during any of the condensation steps. In addition, following synthesis, oligonucleotides can also be labeled at essentially number of positions (Eckstein et al. (Eds.), *Oligonucleotides and Analogues: A Practical Approach*, Oxford University Press (1992), Chu et al. (1983)

"Derivatization of unprotected polynucleotides," *Nucleic Acids Res.* 11 (18): 6513-6529, and U.S. Pat. No. 5,118,800, entitled "Oligonucleotides possessing a primary amino group in the terminal nucleotide," issued Jun. 2, 1992 to Smith et al., which are each incorporated by reference). To further illustrate, oligonucleotides may also be labeled on their phosphodiester backbone (Eckstein et al. (1992), supra) or at the 3'-terminus (Nelson et al. (1992) "Oligonucleotide labeling methods. 3. Direct labeling of oligonucleotides employing a novel, non-nucleosidic, 2-aminobutyl-1,3-propanediol backbone," *Nucleic Acids Res.* 20(23):6253-6259, U.S. Pat. No. 5,401,837, entitled "Method for labeling the 3' terminus of a synthetic oligonucleotide using a unique multifunctional controlled pore glass (MF-CPG) reagent in solid phase oligonucleotide synthesis," issued Mar. 28, 1995 to Nelson, and U.S. Pat. No. 5,141,813, entitled "Multifunctional controlled pore glass reagent for solid phase oligonucleotide synthesis," issued Aug. 25, 1992 to Nelson, which are each incorporated by reference).

In certain embodiments, modified nucleotides are included in the blocked oligonucleotides described herein. To illustrate, the introduction of modified nucleotide substitutions into oligonucleotide sequences can, e.g., alter the melting temperature of the oligonucleotides as desired. In some embodiments, this can yield greater sensitivity relative to corresponding unmodified oligonucleotides even in the presence of one or more mismatches in sequence between the target nucleic acid and the particular oligonucleotide. Exemplary modified nucleotides that can be substituted or added in oligonucleotides include, e.g., C5-ethyl-dC, C5-methyl-dC, C5-ethyl-dU, 2,6-diaminopurines, C5-propynyl-dU, C5-propynyl-dC, C7-propynyl-dA, C7-propynyl-dG, C5-propargylamino-dC, C5-propargylamino-dU, C7-propargylamino-dA, C7-propargylamino-dG, 7-deaza-2-deoxyxanthosine, pyrazolopyrimidine analogs, pseudo-dU, nitro pyrrole, nitro indole, 2'-O-methyl Ribo-U, 2'-O-methyl Ribo-C, an 8-aza-dA, an 8-aza-dG, a 7-deaza-dA, a 7-deaza-dG, N4-ethyl-dC, and N6-methyl-dA. To further illustrate, other examples of modified oligonucleotides include those having one or more LNA™ monomers. Nucleotide analogs such as these are also described in, e.g., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference. Oligonucleotides comprising LNA™ monomers are commercially available through, e.g., Exiqon A/S (Vedbæk, DK). Additional oligonucleotide modifications are referred to herein, including in the definitions provided above.

VI. Nucleotide Incorporating Biocatalysts

Figure 11:
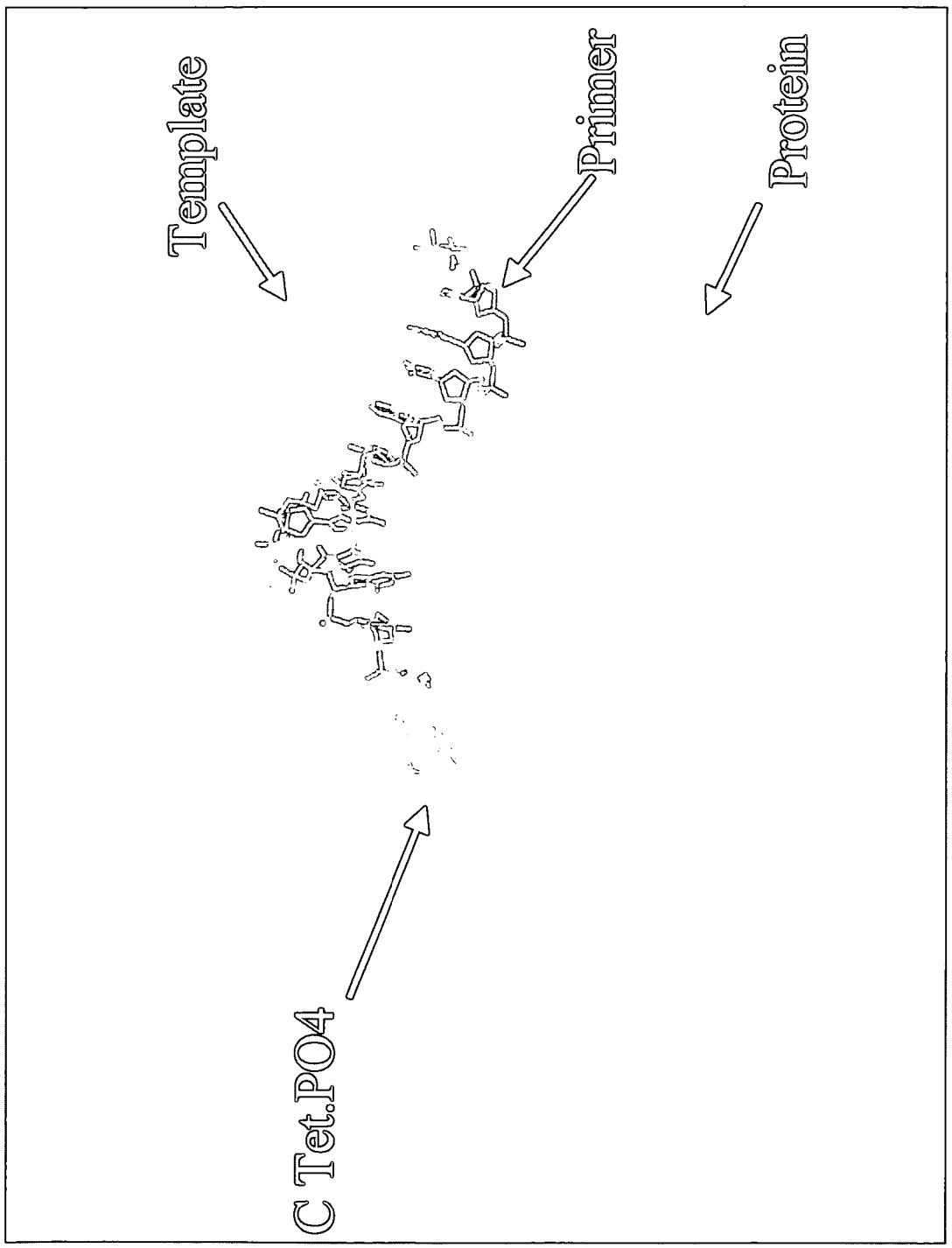
FIG. 11 schematically illustrates a polymerase bound to a template nucleic acid and to a primer nucleic acid with an incorporated cytidine tetraphosphate nucleotide.

The blocked oligonucleotides and polynucleotides of the invention are typically non-extendible by at least one nucleotide incorporating biocatalyst selected from, e.g., a G46E E678G CS5 DNA polymerase, a G46E L329A E678G CS5 DNA polymerase, a G46E L329A D640G S671F CS5 DNA polymerase, a G46E L329A D640G S671F E678G CS5 DNA polymerase, a G46E E678G CS6 DNA polymerase, a ΔZ05R polymerase, a E615G Taq DNA polymerase, a *Thermus flavus* polymerase, a TMA-25 polymerase, a E678G TMA-25 polymerase, a TMA-30 polymerase, a E678G TMA-30 polymerase, a Tth DNA polymerase, a *Thermus* specie SPS-17 polymerase, a E615G Taq polymerase, a *Thermus* Z05R polymerase, a T7 DNA polymerase, a Kornberg DNA polymerase I, a Klenow DNA polymerase, a Taq DNA polymerase, a Micrococcal DNA polymerase, an alpha DNA polymerase, a reverse transcriptase, an AMV reverse transcriptase, an M-MuLV reverse transcriptase, a DNA polymerase, an RNA polymerase, a *E. coli* RNA polymerase, an SP6 RNA polymerase, a T3 RNA polymerase, a T4 DNA polymerase, a T7 RNA polymerase, an RNA polymerase II, a terminal transferase, a polynucleotide phosphorylase, a ribonucleotide incorporating DNA polymerase, and the like. The sequences of certain of these nucleotide incorporating biocatalysts are publicly available from various sources including, e.g., GenBank® and the like. To further illustrate aspects of the invention, FIG. 11 schematically depicts a polymerase bound to a template nucleic acid and to a primer nucleic acid with an incorporated cytidine tetraphosphate nucleotide.

One type of polymerase that can incorporate, but which generally cannot extend, a 2'-terminator nucleotide of the invention lacks an F to Y mutation in helix O of the enzyme or otherwise lacks a mutation that enhances incorporation of 3'-deoxynucleotides by the enzyme. Optionally, the enzyme comprises a 3'-5' exonuclease activity and/or is a thermostable enzyme. The enzyme is typically derived from an organism, such as *Thermus antranikianii, Thermus aquaticus, Thermus caldophilus, Thermus chliarophilus, Thermus filiformis, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Anaerocellum thermophilum, Bacillus caldotenax, Bacillus stearothermophilus*, or the like.

In some embodiments, the enzyme is modified. Exemplary modified enzymes include, e.g., a G46E E678G CS5 DNA polymerase, a G46E L329A E678G CS5 DNA polymerase, a G46E L329A D640G S671F CS5 DNA polymerase, a G46E L329A D640G S671F E678G CS5 DNA polymerase, a G46E E678G CS6 DNA polymerase, an E615G Taq DNA polymerase, and the like. These modified enzymes generally comprise an increased ability to incorporate 2'-terminator nucleotides relative to an unmodified enzyme. That is, the modified enzymes typically comprise mutations that enhance that incorporation of ribonucleotides, that enhance incorporation of 2'-modified analogs of ribonucleotides, and/or that reduce or eliminate 5'-3' exonuclease activity, e.g., relative to an enzyme that lacks one or more of these mutations. Additional details relating to useful nucleotide incorporating biocatalysts are also provided in, e.g., entitled "MUTANT DNA POLYMERASES AND RELATED METHODS", filed Oct. 18, 2006 by Bauer et al., U.S. Pat. No. 5,939,292, entitled "THERMOSTABLE DNA POLYMERASES HAVING REDUCED DISCRIMINATION AGAINST RIBO-NTPS," which issued Aug. 17, 1999 to Gelfand et al., U.S. Pat. No. 4,889,818, entitled "PURIFIED THERMOSTABLE ENZYME," which issued Dec. 26, 1989 to Gelfand et al., U.S. Pat. No. 5,374,553, entitled "DNA ENCODING A THERMOSTABLE NUCLEIC ACID POLYMERASE ENZYME FROM *THERMOTOGA MARITIMA*," which issued Dec. 20, 1994 to Gelfand et al., U.S. Pat. No. 5,420,029, entitled "MUTATED THERMOSTABLE NUCLEIC ACID POLYMERASE ENZYME FROM *THERMOTOGA MARITIMA*," which issued May 30, 1995 to Gelfand et al., U.S. Pat. No. 5,455,170, entitled "MUTATED THERMOSTABLE NUCLEIC ACID POLYMERASE ENZYME FROM *THERMUS SPECIES* Z05," which issued Oct. 3, 1995 to Abramson et al., U.S. Pat. No. 5,466,591, entitled "5' TO 3' EXONUCLEASE MUTATIONS OF THERMO- STABLE DNA POLYMERASES," which issued Nov. 14, 1995 to Abramson et al., U.S. Pat. No. 5,618,711, entitled "RECOMBINANT EXPRESSION VECTORS AND PURIFICATION METHODS FOR *THERMUS THERMOPHILUS* DNA POLYMERASE," which issued Apr. 8, 1997 to Gelfand et al., U.S. Pat. No. 5,624,833, entitled "PURIFIED THERMOSTABLE NUCLEIC ACID POLYMERASE ENZYME FROM *THERMOTOGA MARITIMA*," which issued Apr. 29, 1997 to Gelfand et al., U.S. Pat. No. 5,674,738, entitled "DNA ENCODING THERMOSTABLE NUCLEIC ACID POLYMERASE ENZYME FROM *THERMUS* SPECIES Z05," which issued Oct. 7, 1997 to Abramson et al., U.S. Pat. No. 5,789,224, entitled "RECOMBINANT EXPRESSION VECTORS AND PURIFICATION METHODS FOR *THERMUS THERMOPHILUS* DNA POLYMERASE," which issued Aug. 4, 1998 to Gelfand et al., U.S. Pat. No. 5,795,762, entitled "5' TO 3' EXONUCLEASE MUTATIONS OF THERMOSTABLE DNA POLYMERASES," which issued Aug. 18, 1998 to Abramson et al., U.S. Pat. Application Publication No. US 2002/0012970, entitled "HIGH TEMPERATURE REVERSE TRANSCRIPTION USING MUTANT DNA POLYMERASES," which published Jan. 31, 2002 by Smith et al., and U.S. patent application Ser. No. 10/401,403, filed Mar. 26, 2003, which are each incorporated by reference.

The production of modified enzymes with, e.g., enhanced efficiency for incorporating 2'-terminator nucleotides or other desired properties may be accomplished by various processes including, e.g., site-directed mutagenesis, chemical modification, etc. More specifically, site-directed mutagenesis is generally accomplished by site-specific primer-directed mutagenesis. This technique is typically conducted using a synthetic oligonucleotide primer complementary to a single-stranded phage DNA to be mutagenized except for a limited mismatch representing the desired mutation. Briefly, the synthetic oligonucleotide is used as a primer to direct synthesis of a strand complementary to the plasmid or phage, and the resulting double-stranded DNA is transformed into a phage-supporting host bacterium. The resulting bacteria can be assayed by, for example, DNA sequence analysis or probe hybridization to identify those plaques carrying the desired mutated gene sequence. To further illustrate, many other approaches to modify nucleic acids, such as "recombinant PCR" methods can also be utilized.

In practicing aspects of the present invention (e.g., producing modified enzymes, performing sequencing reactions, etc.), many conventional techniques in molecular biology and recombinant DNA are optionally utilized. These techniques are well known and are explained in, for example, *Current Protocols in Molecular Biology*, Volumes I, II, and III, 1997 (F. M. Ausubel ed.); Sambrook et al., 2001, *Molecular Cloning: A Laboratory Manual*, Third Edition, Cold Spring Harbor Laboratory Press, Cold Spring Harbor, N.Y.; Berger and Kimmel, *Guide to Molecular Cloning Techniques Methods in Enzymology* volume 152 Academic Press, Inc., San Diego, Calif. (Berger), *DNA Cloning: A Practical Approach*, Volumes I and II, 1985 (D. N. Glover ed.); *Oligonucleotide Synthesis*, 1984 (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); *Methods in Enzymology* Vol. 154 and Vol. 155 (Wu and Grossman, and Wu, eds., respectively).

VII. Business Methods

Figure 24:
FIG. 24 is a block diagram that shows certain steps performed in a business method according to one embodiment of the invention.

In other representative embodiments, the invention provides methods of doing business that involve the blocked oligonucleotides and polynucleotides described herein. For example, FIG. 24 is a block diagram that shows certain steps performed in a business method according to one embodiment of the invention. As shown in step 2400, the method includes receiving an order from a customer for a blocked oligonucleotide or polynucleotide described herein, and/or instructions for producing such an oligonucleotide or polynucleotide. In addition, the method also includes supplying the oligonucleotide or polynucleotide and/or instructions to the customer in response to the order (step 2402). In some embodiments, for example, a business entity receives the order via a personal appearance by the customer or an agent thereof, via a postal or other delivery service (e.g., a common carrier), via a telephonic communication, via an email communication or another electronic medium, or any other suitable method. In some embodiments, the blocked oligonucleotides or polynucleotides and/or instructions that are ordered and/or supplied are included in the kits described herein. Furthermore, the blocked oligonucleotides or polynucleotides and/or instructions are supplied or provided to customers (e.g., in exchange for a form of payment) by any suitable method, including via a personal appearance by the customer or an agent thereof, via a postal or other delivery service, such as a common carrier.

VIII. Kits

The invention also provides various kits, which include instructions for producing the blocked oligonucleotides or polynucleotides described herein, and/or one or more blocked oligonucleotides or polynucleotides. As described herein, the blocked oligonucleotides or polynucleotides of the invention are typically used as primers or probes in various nucleic acid technologies. Accordingly, kits include other reagents (e.g., buffers, enzymes, etc.) and instructions for performing the particular application (e.g., real-time PCR, a PAP-based method, etc.) in addition to blocked oligonucleotides or polynucleotides in certain embodiments. Further, the kits also generally include containers for packaging reagents, instructions, and other kit components.

IX. Examples

The following examples are offered by way of illustration only and are not intended to limit the scope of the claimed invention.

Example I

Regiospecific Synthesis of Uridine Tetraphosphate

Figure 12:
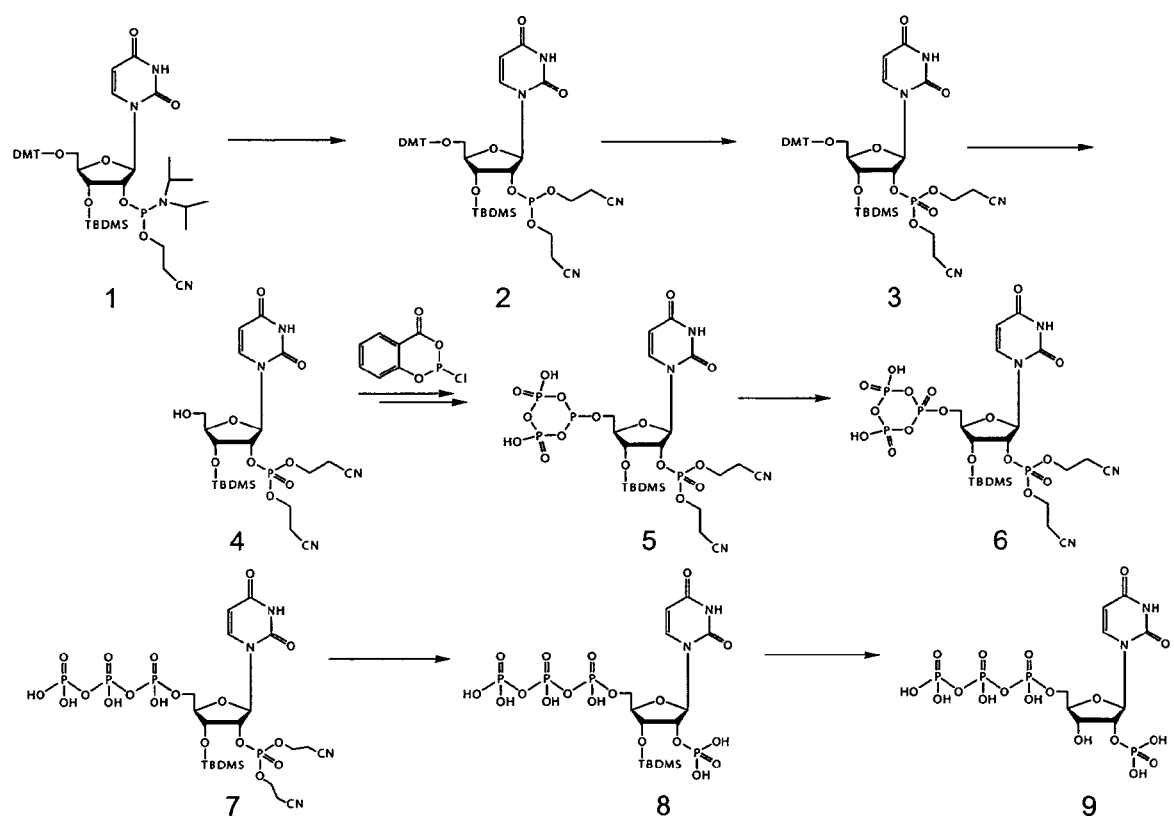
FIG. 12 schematically depicts a regiospecific synthesis pathway for uridine tetraphosphate.

FIG. 12 schematically depicts a regiospecific synthesis pathway for uridine tetraphosphate according to one embodiment of the invention. Note that bracketed numbers refer to compounds shown in FIG. 12 in this example.

Synthesis of 5'-O-DMT-3'-O-TBDMS Uridine 2'-O-(Biscyanoethyl)Phosphite[2]

Compound [1] (ChemGenes cat. # ANP-4845, 0.680 g, 0.790 mmol) was taken up in acetonitrile (Aldrich, anhydrous, 10 mL). 1-H-Tetrazole (Aldrich, 0.211 g, 3.01 mmol) was added to the solution in one portion followed by 3-hydroxypropionitrile (Aldrich, 0.109 mL, 1.58 mmol). The resulting solution was stirred at ambient temperature under an atmosphere of argon for 1 hour. The solvent was removed on a rotary evaporator. The residue was taken up in EtOAc (50 mL), and the resulting solution was washed with saturated aqueous NaHCO$_3$ (2×20 mL). The organic layer was separated and was dried over MgSO$_4$. The crude product was obtained by filtration followed by evaporation of the solvent. A Biotage flash 40S cartridge was preconditioned by eluting a solution of 2% Et$_3$N in CH$_2$Cl$_2$ (200 mL) prior to loading the product mixture. The product mixture was loaded onto the top of the Biotage column as a solution in a minimum amount of CH$_2$Cl$_2$. The product was purified by eluting with a stepped gradient which consisted of 2% Et$_3$N/98% CH$_2$Cl$_2$ (200 mL), 0.5% methanol/2% Et$_3$N/97.5% CH$_2$Cl$_2$ (200 mL), 1% methanol/2% Et$_3$N/97% CH$_2$Cl$_2$ (200 mL). The purified product eluted in the 0.5-1.0% methanol solvent strength fractions. The fractions which contained the purified product were combined, and the solvent was removed on a rotary evaporator. The purified product [2] was obtained in this manner as a white foam (0.510 g, 78% yield).

Synthesis of 5'-OH-3'-O-TBDMS Uridine 2'-O-(Bis-cyanoethyl)Phosphate[4]

The compound [2] (0.335 g, 0.403 mmol) was dissolved in THF (Aldrich, anhydrous, 6.7 mL) at room temperature. A solution of I$_2$ in pyridine/THF/H$_2$O (0.02M, 2.2:6.8:1; Glen Research, 24 mL, 0.48 mmol) was added to the mixture with stirring. The resulting solution was allowed to stir for 20 minutes at ambient temperature. An aqueous solution of sodium hydrogen sulfite (1 g in 3 mL H$_2$O) was added dropwise until the I$_2$ color was quenched in the solution. The volatile solvents were removed on a rotary evaporator. The solution was diluted to a total volume of 100 mL with EtOAc. The solution was washed carefully with saturated aqueous NaHCO$_3$ (50 mL). The organic layer was separated and dried over MgSO$_4$. The solution was filtered, and the solvent was removed on a rotary evaporator to give compound [3]. This crude [3] material was taken up in CH$_2$Cl$_2$ (8 mL) with stirring. The resulting solution was cooled to −30° C. A solution of trichloroacetic acid (Fisher, 0.487 g, 2.98 mmol) in CH$_2$Cl$_2$ (4 mL) was added to the cooled stirring solution of nucleoside. The red/brown color characteristic of the trityl cation appeared immediately. Stirring was continued at −30° C. for 20 minutes after the addition of trichloroacetic acid. MeOH (1.5 mL) was added and the resulting solution was transferred to a separatory funnel. The solution was diluted with CH$_2$Cl$_2$ (75 mL). The resulting solution was washed with saturated aqueous NaHCO$_3$ (2×30 mL). The organic layer was separated and was dried over Na$_2$SO$_4$. The solution was filtered, and the solvent was removed on a rotary evaporator. The crude product was purified by flash column chromatography on silica gel using a Biotage 40S cartridge. The product was loaded onto the top of the Biotage column as a solution in a minimum amount of CH$_2$Cl$_2$. The product was eluted using a stepped gradient of EtOAc (200 mL), 1% MeOH in EtOAc (200 mL), 2% MeOH in EtOAc (200 mL), 3% MeOH in EtOAc (200 mL), 4% MeOH in EtOAc (200 mL), 5% MeOH in EtOAc (200 mL) and 10% MeOH in EtOAc (200 mL). The product eluted using the 10% MeOH solvent strength. The fractions containing the purified product were combined, and the solvent was removed on a rotary evaporator. The pure product [4] was obtained in this manner as a white foam (0.145 g, 66% yield).

Conversion of Compound [4] to its Corresponding Triphosphate [7]

5'-OH-3'-O-TBDMS Uridine 2'-O-(biscyanoethyl)phosphate (compound [4], 0.0335 g, 0.0615 mmol) was dried by co-evaporation with pyridine (3×0.2 mL). The resulting material was taken up in pyridine (Aldrich, anhydrous, 70 μL) and DMF (Aldrich, anhydrous, 180 μL). A solution of salicylphosphorochloridite in DMF (0.5 M, 137 μL, 0.0677 mmol) was added to the stirring solution. The resulting reaction mixture was stirred at ambient temperature for 20 minutes. Tri-N-butylamine (Aldrich, 38 μL, 0.160 mmol) was added, followed by a solution of tetrabutylammonium pyrophosphate in DMF (0.5 M, 185 μL, 0.0925 mmol). The resulting reaction mixture was stirred at ambient temperature for 20 minutes. A solution of I$_2$ in pyridine/H$_2$O/THF (0.02 M, Glen Research, 3.6 mL, 0.072 mmol) was added, and the resulting reaction mixture was stirred for a further 20 minutes at ambient temperature. The excess iodine was quenched by dropwise addition of a sodium hydrogen sulfite solution (1 g of NaHSO$_3$ in 3 mL of water) until the characteristic color of the iodine had disappeared. The resulting solution was allowed to stand at ambient temperature overnight. Note that standing at −20° C. over 72 hours accomplishes the same transformation of cyclic triphosphate to linear triphosphate. At this point, no cyclic triphosphate was detectable by flow injection mass spectrometry (MS). The resulting linear triphosphate was isolated by reversed phase HPLC (Column: Zorbax SB-C18, 21.2 mm×25 cm. Solvent A: 0.1 M TEAA, 2.5% CH$_3$CN, pH=7.0; Solvent B: CH$_3$CN. Flow rate: 10.0 mL/minute. Gradient: t=0 minutes, 100% A; t=15 minutes, 50% A/50% B; t=20 minutes, 100% B; t=25 minutes, 100% B; t=25.01 minutes, 100% A; t=30 minutes, 100% A. Retention time: 20.9 min.).

Synthesis of 3'-O-TBDMS-Uridine Tetraphosphate [8]

The uridine 2'-O-bis(O-cyanoethyl)phosphate [7] (9 mg, 0.0117 mmol) was coevaporated successively with MeOH (3×5 mL), CH$_2$Cl$_2$ (3×5 mL) and finally with anhydrous CH$_3$CN (1×5 mL). The material was then taken up in CH$_3$CN (Aldrich, anhydrous, 2.25 mL). 1,8-Diazabicyclo[5.4.0]undec-7-ene (DBU, Aldrich, 175 μL, 1.17 mmol) and chlorotrimethylsilane (Aldrich, 59 μL, 0.468 mmol) were added to the stirring solution. The reaction mixture was allowed to stir at ambient temperature for 2 hours. Water (1 mL) was added, and the volatile materials were removed by a rotary evaporator. The resulting product was purified by reversed phase HPLC. (Column: Zorbax SB-C18, 21.2 mm×25 cm. Solvent A: 0.1 M TEAA, 2.5% CH$_3$CN, pH=7.0; Solvent B: CH$_3$CN. Flow rate: 10.0 mL/minute. Gradient: t=0 minutes, 100% A; t=15 minutes, 50% A/50% B; t=20 minutes, 100% B; t=25 minutes, 100% B; t=25.01 minutes, 100% A; t=30 minutes, 100% A. Retention time: 13.6 minutes). The compound [8] obtained in this manner after lyophilization was quantified by UV (8 mg). The molar extinction co-efficient ($\epsilon_{max}$) of uridine was taken to be 10 (mM$^{-1}$cm$^{-1}$) and its absorption maxima ($\lambda_{max}$) was taken to be 262 nm.

Synthesis of Uridine Tetraphosphate [9]

The 3'-O-TBDMS-Uridine Tetraphosphate [8] (2.55 mg, 0.00376 mmol) was taken up in CH$_3$CN (Aldrich anhydrous, 160 μL). Tetrabutylammonium fluoride in THF (1.0 M, Aldrich, 113 μL, 0.113 mmol) and HOAc (glacial, Aldrich, 2.2 μL, 0.0376 mmol) were added to the solution. The resulting reaction mixture was allowed to stir for 21 hours at ambient temperature. HPLC analysis of the reaction at this time showed no remaining silyl ether. The volatile materials were removed on a rotary evaporator. The product mixture was resuspended in H$_2$O, and the product was purified by reversed phase HPLC. (Column: Zorbax SB-C18, 9.4 mm×25 cm.

Solvent A: 0.1 M TEAA, 2.5% CH$_3$CN, pH=7.0; Solvent B: CH$_3$CN. Flow rate: 4.0 mL/minute. Gradient: t=0 minutes, 100% A; t=15 minutes, 75% A/25% B; t=15.01 minutes, 100% B; t=20 minutes, 100% A; t=27 minutes, 100% A. Retention time: 7.05 minutes). The purified material was lyophilized. The resulting material was resuspended and lyophilized a total of 5 times to ensure complete removal of TEAA salts. Before the final lyophilization, the material was quantified by UV (2.00 mg, 94 % yield). The compound [9] obtained in this manner was a white solid.

Example II

Synthesis of Adenosine Tetraphosphate

Overview

This example illustrates the synthesis of adenosine tetraphosphate according to one synthetic reaction of the present invention. As schematically shown, in FIG. 13 the synthetic reaction produced a mixture of 5'-triphosphate-3'-monophosphate adenine nucleosides and 5'-triphosphate-2'-monophosphate adenine nucleosides. In the synthetic reaction, ATP was reacted with trisodium trimetaphosphate (NaPO$_3$)$_3$ in 1N KOH at room temperature. The reaction mixture was allowed to proceed for 8 hours. The molar ratio of 5'-triphosphate-3'-monophosphate adenine nucleoside to 5'-triphosphate-2'-monophosphate adenine nucleoside produced was approximately 50:50.

Figure 14A:
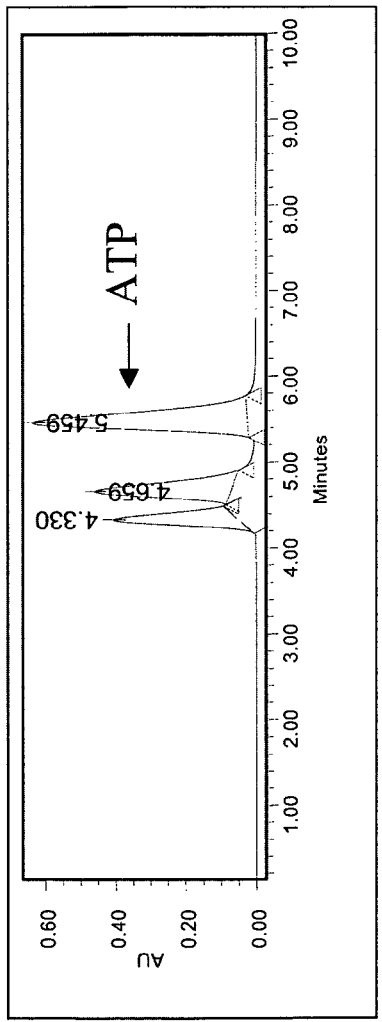
FIGS. 14A-C are HPLC traces that show the detection of adenosine tetraphosphate nucleotides.
Figure 14B:
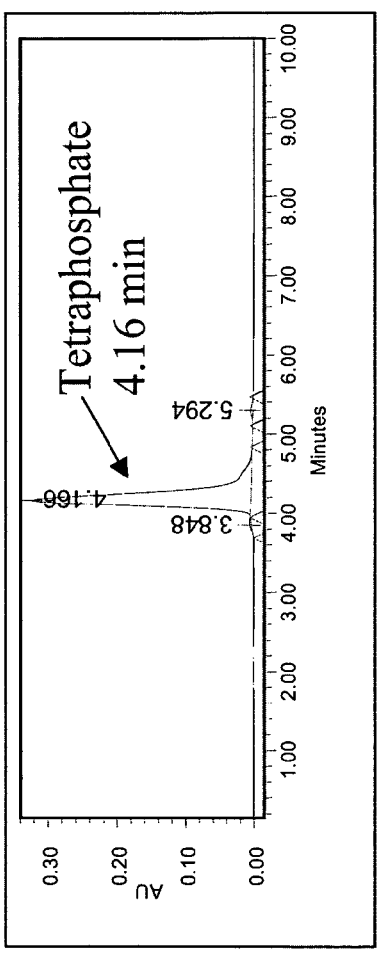
Figure 14C:
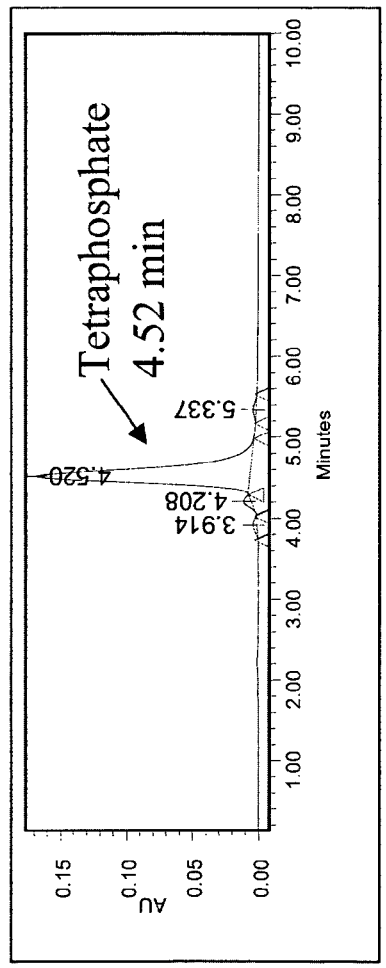

FIGS. 14A-C are HPLC traces (abscissa—retention time (minutes); ordinate—absorbance units (AU) at 260 nm) showing the detection of various adenosine nucleotides. The traces were generated following nucleotide separation using ion-pairing RP-HPLC chromatography. In particular, the analysis and purification was carried out on Symmetry-Shield™ reverse phase column (Waters Corporation, Milford, Mass.) with TEAA-acetonitrile buffer. FIG. 14A shows the HPLC analysis of the adenosine tetraphosphate reaction, whereas FIGS. 14B and C show the HPLC analysis of purified adenosine tetraphosphate fractions (retention times: 4.166 and 4.52 minutes, respectively). A separate NMR analysis ($^{31}$P NMR; 2D Proton-Phosphorus NMR), which is described further below, revealed that the peak that eluted at 4.33 minutes corresponds to 2'-PO$_4$-ATP and the peak at 4.65 minutes corresponds to 3'-PO$_4$-ATP (see, FIG. 14A).

NMR Analysis

The $^1$H and $^{31}$P chemical shifts of the adenosine tetraphosphate with the peak at 4.33 minutes in the HPLC analysis, described above, are shown in Table I. The assignment of the proton chemical shifts was facilitated by the COSY spectrum and the fact that proton H-1' could easily be identified because it should have had only one proton coupling and it should have been the furthest downfield of the ribose protons.

TABLE I

| Atom | $^1$H Shift (ppm), Multiplicity, Splittings | $^{31}$P Shift (ppm), Multiplicity, P-P Splittings |
| --- | --- | --- |
| 2 | 8.50, s | — |
| 8 | 8.27, s | — |
| 1' | 6.27, d, 5.4Hz | — |
| 2' | 5.05, d of t, 8.8, 5.5Hz | — |
| 3' | 4.67, d of d, 5.4, 4.1Hz | — |
| 4' | 4.41, m | — |
| 5' | 4.26, d of d, 5.2. 3.3Hz | — |
| P2' | — | 0.87, s |
| Pα | — | −10.69, d, 19.5Hz |
| Pβ | — | −22.44, t, 19.5Hz |
| Pγ | — | −9.92, d, 19.5Hz |

$^{31}$P spectra with and without proton decoupling were also acquired. Four phosphate peaks were observed in the $^{31}$P spectra. Three of the peaks at −22.44, −10.69, and −9.92 ppm showed $^{31}$P-$^{31}$P coupling and belonged to the triphosphate group at the 5' position of the ribose ring. The fourth peak, at 0.87 ppm, showed no $^{31}$P-$^{31}$P coupling and belonged to the monophosphate. However, the $^{31}$P chemical shift of the monophosphate was very similar in both adenosine tetraphosphates (i.e., peaks at 4.33 and 4.65 minutes), 0.87 and 1.08 ppm respectively, and therefore was not useful in determining the position of the phosphate group. Additionally, the linewidths of the monophosphate and triphosphate peaks were so broad that the $^{31}$P-$^1$H couplings were not resolved in the $^{31}$P spectrum acquired without proton decoupling.

Figure 13:
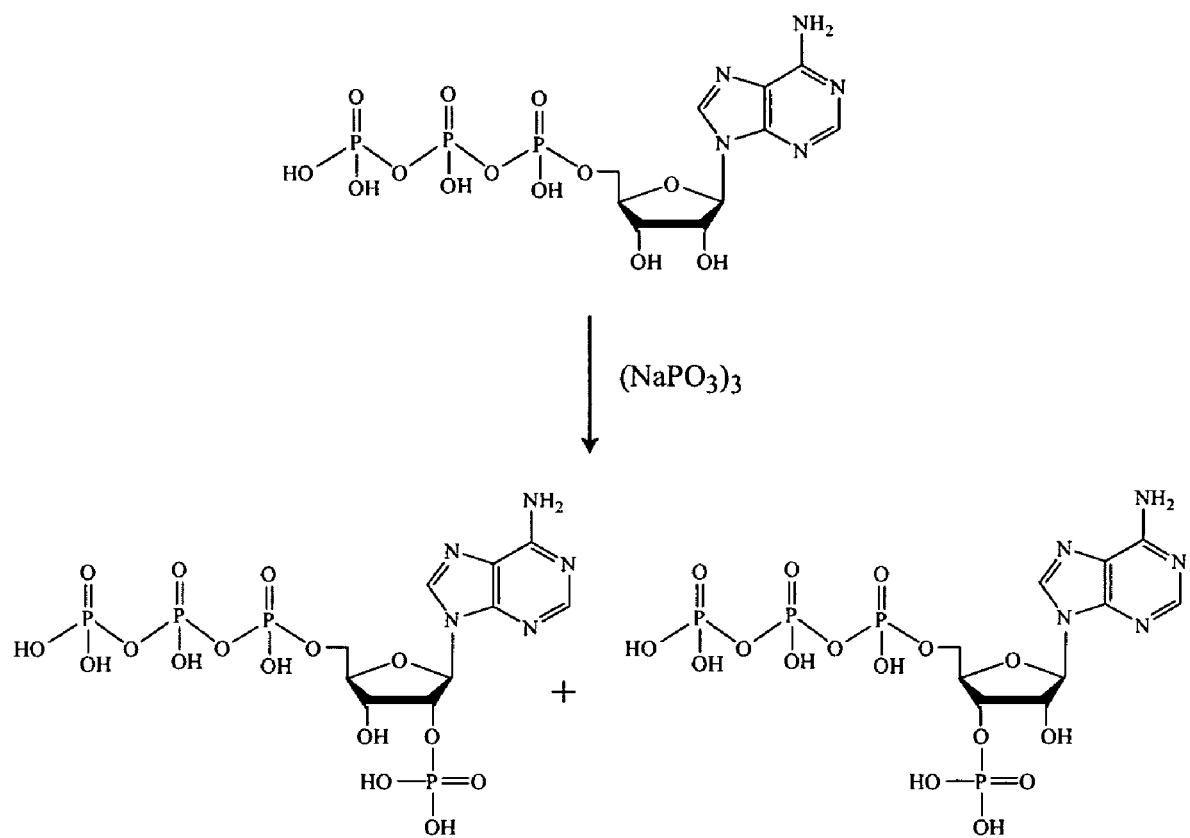
FIG. 13 schematically illustrates a synthetic reaction that produces a mixture of 5'-triphosphate-3'-monophosphate adenine nucleosides and 5'-triphosphate-2'-monophosphate adenine nucleosides.

A comparison of the H-2' and H-3' chemical shifts of adenosine 5'-phosphate, adenosine 2'-monophosphate, and adenosine tetraphosphate (peak at 4.33 minutes) showed that the mono-phosphate is attached at C-2' of the adenosine tetraphosphate with a peak at 4.33 minutes (see, Table II). Additionally, H-2', which had two neighboring protons and therefore was expected to be a doublet of doublets or a triplet, was a doublet of triplets. The additional 8.8 Hz coupling is the right magnitude to be a three bond $^{31}$P-$^1$H coupling. Based upon these results, the structure of the adenosine tetraphosphate with a peak at 4.33 minutes was determined and corresponds to 2'-PO$_4$-ATP. The structure of 2'-PO$_4$-ATP is schematically shown in FIG. 13.

TABLE II

| Molecule | H-2' (ppm) | H-3' (ppm) |
| --- | --- | --- |
| Adenosine 5'-phosphate | 4.75 | 4.51 |
| Adenosine 2'-monophosphate | 5.19 | 4.57 |
| Adenosine tetraphosphate (4.33 minutes) | 5.05 | 4.67 |

The sample with a peak at 4.65 minutes was a mixture of a nucleotide and what appeared to be a large amount of triethylamine salt. The $^1$H and $^{31}$P chemical shifts and measured splittings of the nucleotide, as measured from the $^1$H and $^{31}$P spectra, are shown in Table III. Like the adenosine tetraphosphate with a peak at 4.33 minutes, the assignment of the proton chemical shifts was facilitated by the COSY spectrum and the fact that proton H-1' could easily be identified because it should have had only one proton coupling and it should have been the furthest downfield of the ribose protons. The coupled and decoupled $^{31}$P spectra were not useful for the same reasons discussed above for the adenosine tetraphosphate having a peak at 4.33 minutes.

TABLE III

| Atom | $^1$H Shift (ppm), Multiplicity, Splittings | $^{31}$P Shift (ppm), Multiplicity, P-P Splittings |
| --- | --- | --- |
| 2 | 8.56, s | — |
| 8 | 8.27, s | — |
| 1' | 6.18, d 6.7Hz | — |
| 2' | ~4.8, m | — |
| 3' | ~4.8, m | — |
| 4' | 4.60, p, ~2.8 | — |
| 5$_a$' | 4.28, d of d of d, 12.0, 5.2, 2.8 | — |
| 5$_b$' | 4.23, d of d of d, 12.0, 4.4, 2.6 | — |
| P3' | — | 1.08, s |
| Pα | — | −10.70, d, 19.0Hz |
| pβ | — | −22.42, t, 19.0Hz |
| Pγ | — | −9.92, d, 19.0Hz |

The chemical shifts of H-2' and H-3' were both about 4.8 ppm for the adenosine tetraphosphate sample with the peak at 4.65 minutes. H-2', therefore, moved back upfield, close to the chemical shift of H-2' in adenosine 5'-phosphate, 4.75 ppm (see, Table II). H-3' moved downfield relative to the chemical shift of H-3' in both adenosine 5'-phosphate, 4.51 ppm, and adenosine tetraphosphate (peak at 4.33 minutes), 4.67 ppm (see, Table II). Based on these observations, the structure of the adenosine tetraphosphate with a peak at 4.65 minutes was determined and corresponds to 3'-$PO_4$-ATP. The structure of 3'-$PO_4$-ATP is schematically shown in FIG. 13.

Example III

Figure 15:
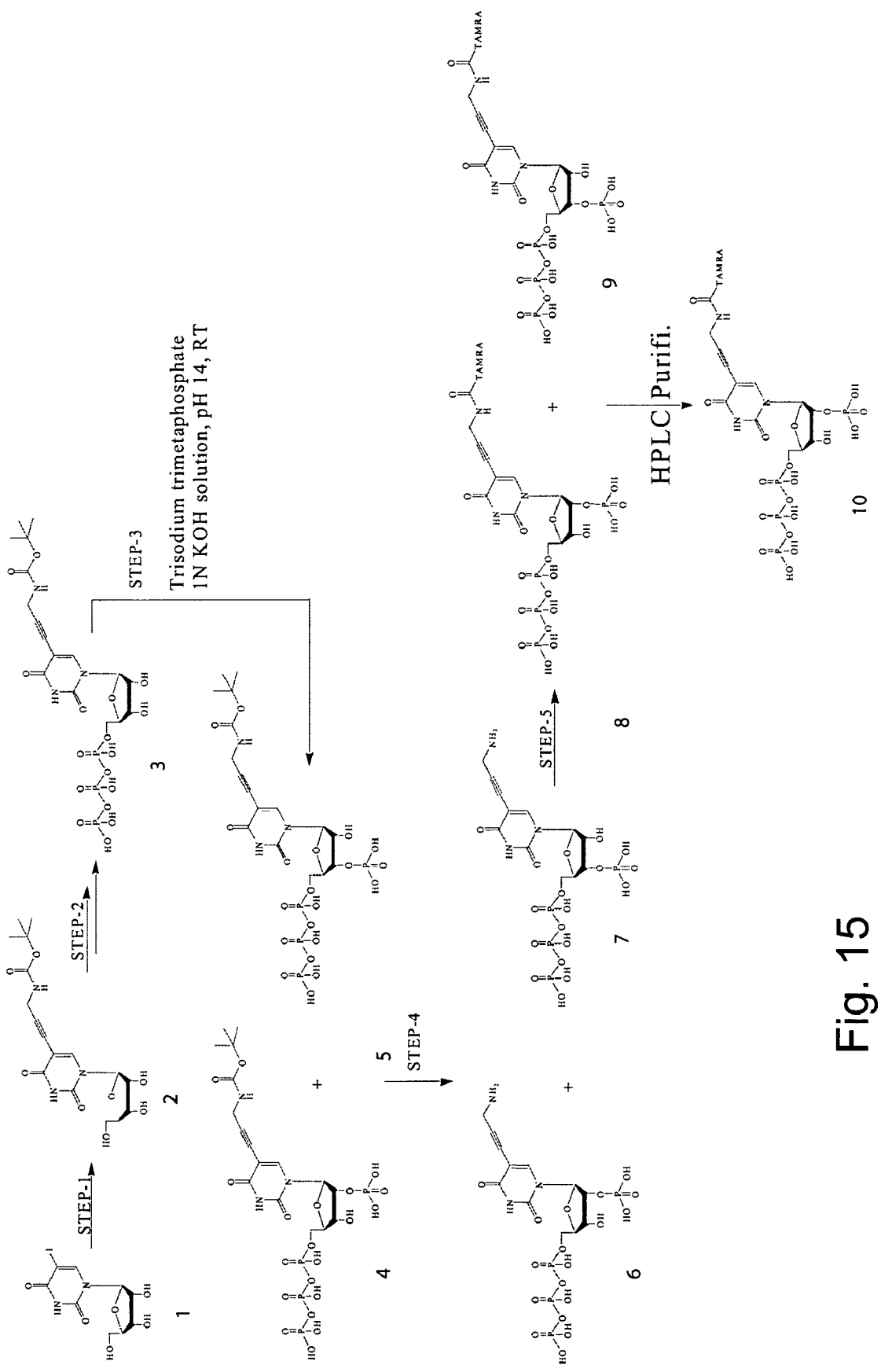
FIG. 15 schematically shows certain steps in a synthesis pathway for TAMRA labeled uridine tetraphosphates.

Synthesis of Tamra Labeled
2'-Monophosphate-Uridine Triphosphates and
3'-Monophosphate-Uridine Triphosphates This example illustrates a synthetic pathway for TAMRA labeled 2'-monophosphate-uridine triphosphates and 3'-monophosphate-uridine triphosphates according to one embodiment of the invention. To further illustrate, FIG. 15 schematically shows certain steps in the pathway that are described in this example. Note that bracketed numbers refer to compounds shown in FIG. 15 in this example.

Figure 16:
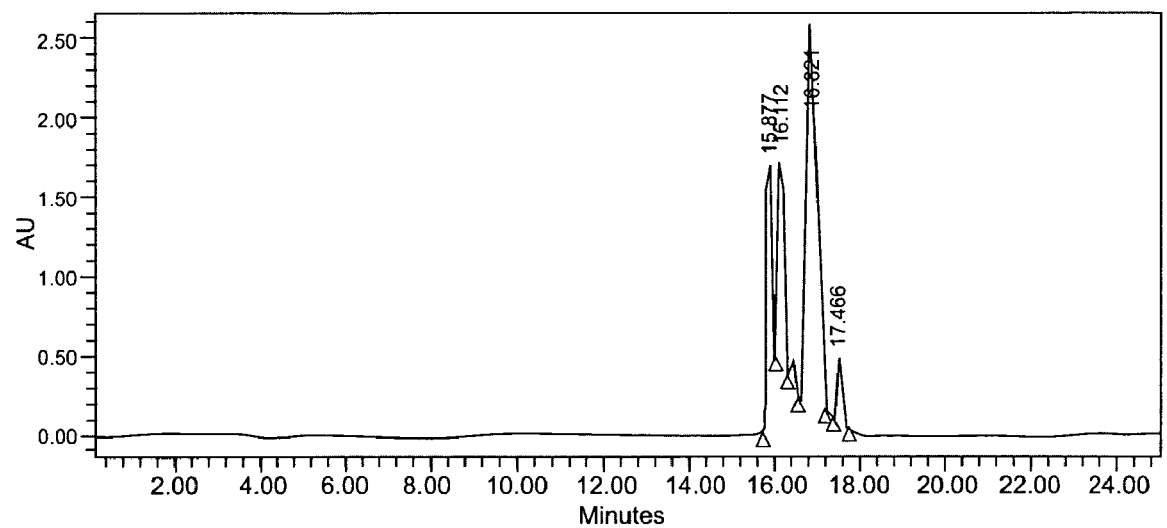
FIG. 16 is an HPLC chromatogram that shows the detection of BOC-protected propargyl uridine tetraphosphates corresponding to structures 4 and 5 shown in FIG. 15.

Compound [3] was taken up in $H_2O$ (300 μL) and 100 μL of this solution was added to a conical vial. The solution in the conical vial was diluted with 1.0 mL of 1N KOH. Sodium trimetaphosphate (50 mg) was added and the solution was stirred at ambient temperature for one hour. Fifty mg of sodium trimetaphosphate was added and stirring was continued for two additional hours. An additional 50 mg of sodium trimetaphosphate was then added and stirring was continued overnight at ambient temperature. The next day, 80 μL of glacial acetic acid was added to bring the pH to about 7.0. The resulting reaction mixture was then purified by RP-HPLC. First, the portion of the reaction mixture including the nucleoside was separated from the salts. After lyophilization, the tetraphosphates were separated from the starting material. FIG. 16 is a chromatogram (abscissa—retention time (minutes); ordinate—absorbance units (AU) at 290 nm) that shows the detection of these tetraphosphates. In particular, the peaks eluted at 15.9 and 16.1 minutes correspond to the tetraphosphates and the peak at 16.8 corresponds to the starting material.

Seven mg of the tetraphosphate isomer mixture (compounds [4] and [5]) were taken up in 200 μL of trifluoroacetic acid (TFA) at ambient temperature. The resulting solution was stirred for 30 minutes. The solution was then cooled in liquid nitrogen and the TFA was removed with lyophilization. The material was carried on to reaction with carboxytetramethylrhodamine succinimidyl ester (TAMRA-SE) without further manipulation.

A TAMRA-SE stock solution was prepared by dissolving 5 mg of TAMRA-SE in 350 μL of dimethylformamide (DMF). In addition, a tetraphosphate stock solution (including compounds [6] and [7]) was prepared by dissolving 6 mg of the tetraphosphate mixture in 100 μL of $H_2O$.

The TAMRA-SE stock solution was transferred to a conical vial along with 175 μL of $H_2O$. In addition, 1.875 μL of a labeling buffer (0.1M sodium tetraborate) and the tetraphosphate stock solution was added to the mixture. The resulting reaction mixture was stirred in the dark (conical vial covered with aluminum foil) at ambient temperature overnight. The next day, HPLC separation of 100 μL of the reaction mixture showed two peaks eluting at approximately 17 minutes, which were thought to be the labeled tetraphosphate isomers (compounds [8] and [9]). Fractions corresponding to these peaks were isolated from the rest of the reaction mixture by RP-HPLC. After concentrating the collected sample by lyophilization, flow injection analysis-mass spectrometry (FIA-MS) showed an ion at 1027.8, which deviated from the mass of the expected (M-H)⁻ ion by one mass unit. The remainder of the reaction mixture was allowed to stir at ambient temperature overnight.

It is believed that since the fluorescent label is positively charged, the removal of one proton (M-H) would yield an overall neutral molecule. Therefore, (M-2H) would lead to a molecule detectable by MS as a mass:charge ratio of −1. This may account for the observed molecular ion referred to above.

Figure 17:
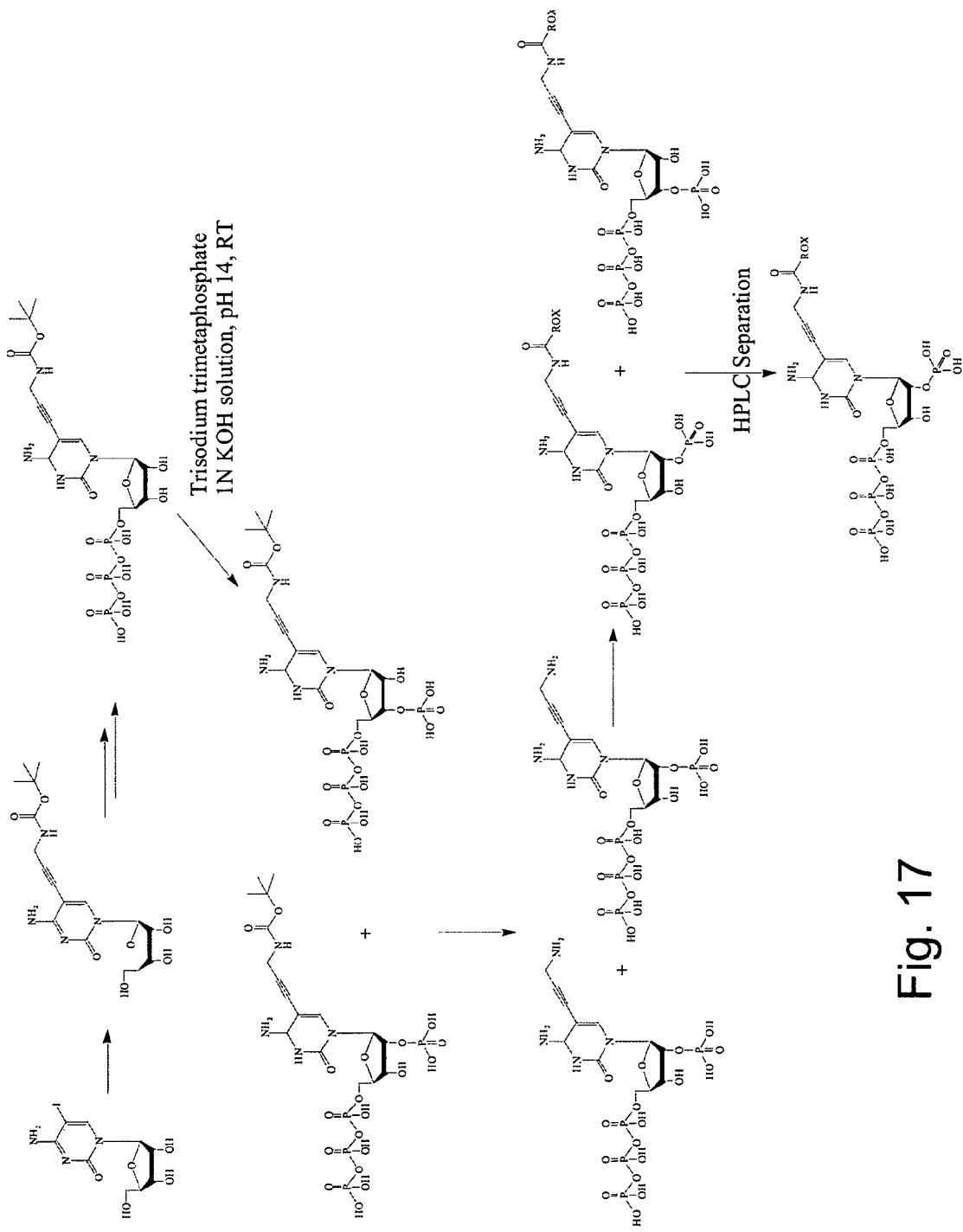
FIG. 17 schematically illustrates certain steps in a synthesis pathway for ROX labeled cytidine tetraphosphates.
Figure 18:
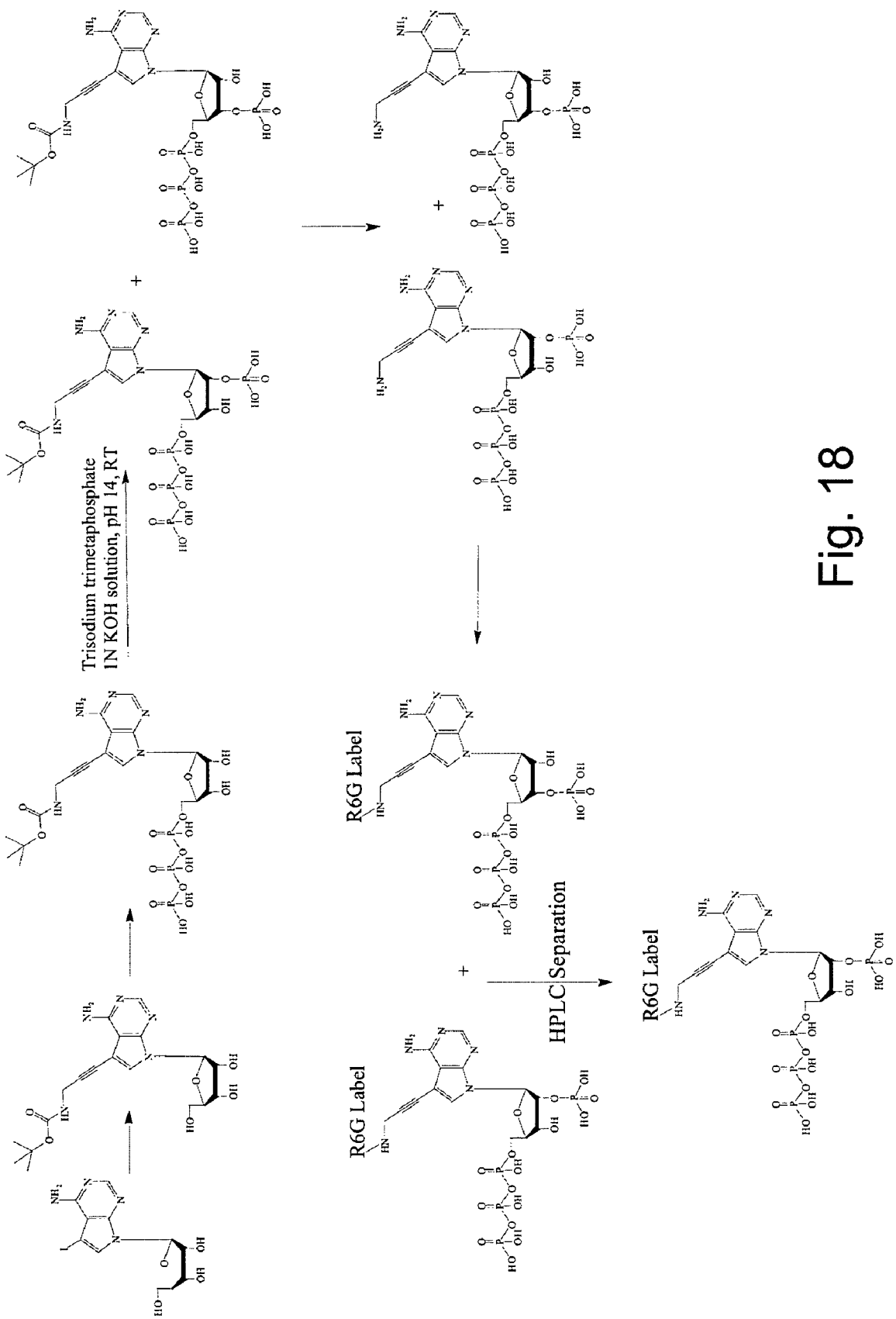
FIG. 18 schematically depicts certain steps in a synthesis pathway for R6G labeled adenine tetraphosphates.
Figure 19:
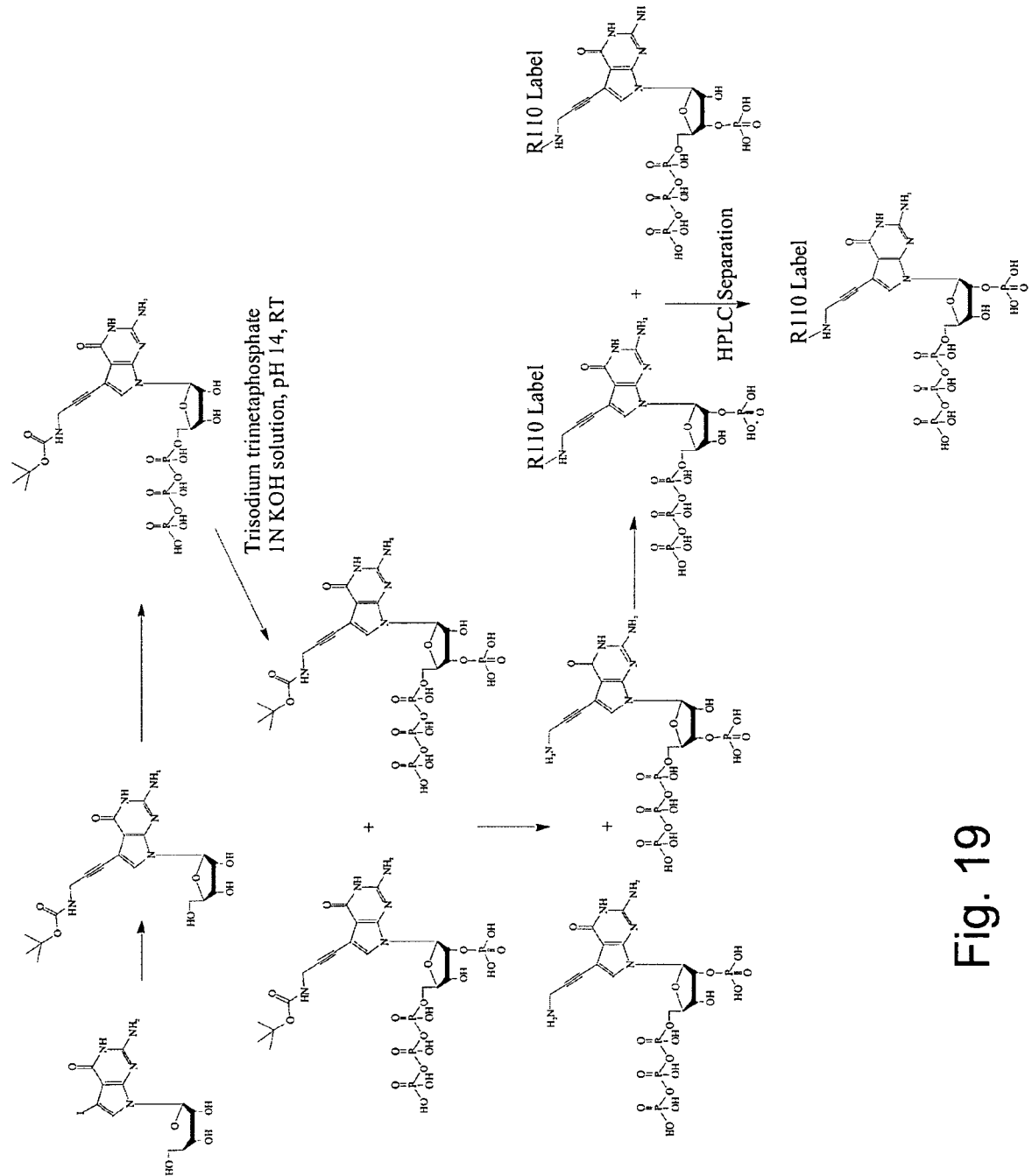
FIG. 19 schematically shows certain steps in a synthesis pathway for R110 labeled guanine tetraphosphates.

Other exemplary synthesis pathways for additional labeled tetraphosphates are schematically depicted in FIGS. 17-19. In particular, FIG. 17 schematically illustrates certain steps in a synthesis pathway for ROX labeled cytidine tetraphosphates. FIG. 18 schematically depicts certain steps in a synthesis pathway for R6G labeled adenine tetraphosphates. FIG. 19 schematically shows certain steps in a synthesis pathway for R110 labeled guanine tetraphosphates.

Example IV

Termination of Primer Nucleic Acid Extension Using
2'-Terminator Nucleotides

Figures 20A, 20B, 20C, 20D:
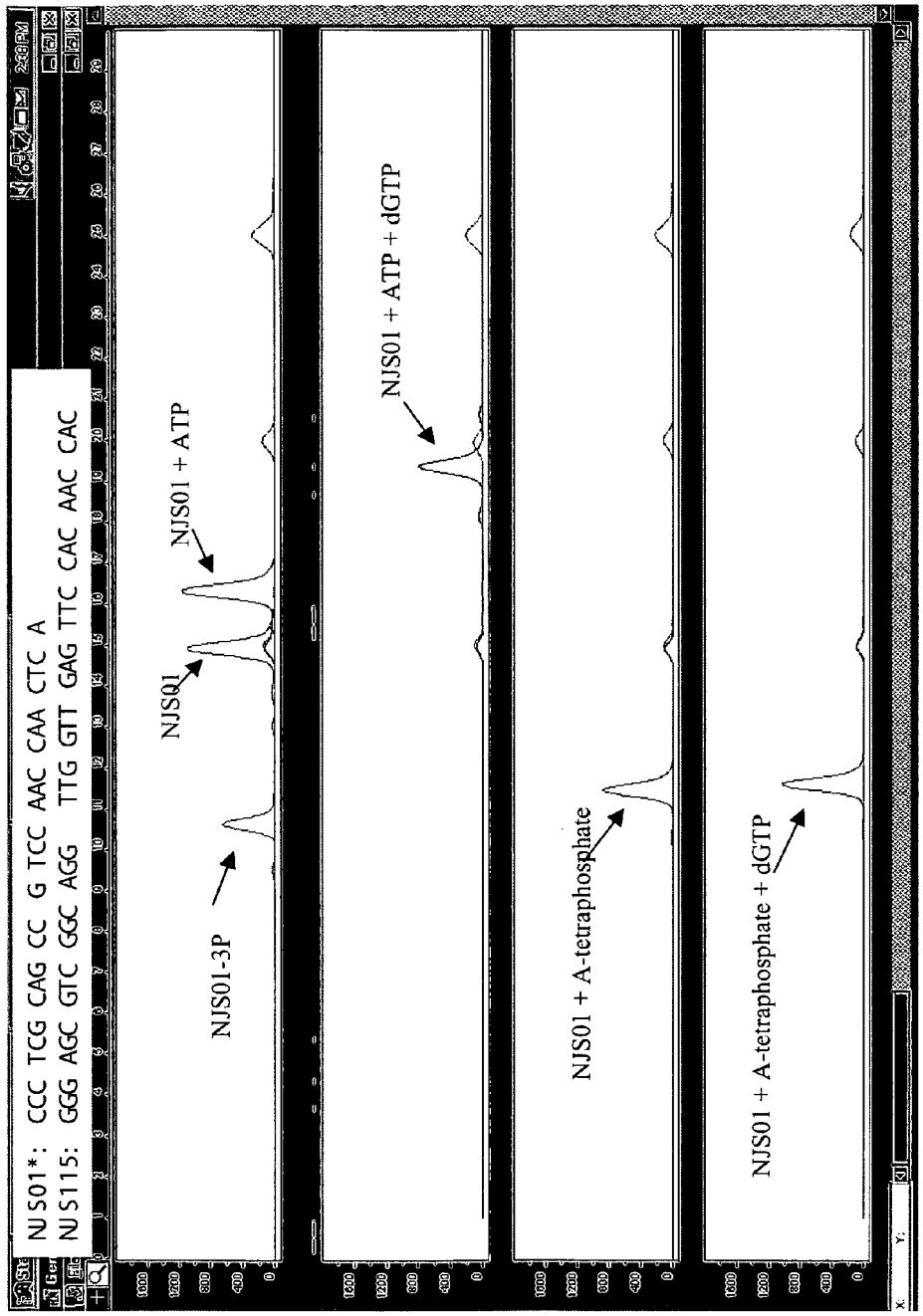
FIGS. 20A-D are electropherograms that show the detection of various extended primer nucleic acids (SEQ ID NOS 28 and 29, respectively in order of appearance).

This example shows a comparison of two primer nucleic acid extension reactions. The sequences of the template and primer nucleic acids used in these analyses are shown in FIG. 20, corresponding to sequence designations NJS115 and NJS01*, respectively. FIGS. 20A and B are electropherogram traces that show the incorporation of adenine and guanine residues into NJS01* in a reaction that did not involve terminator nucleotides. In contrast, FIGS. 20C and D are electrophoretogram traces that show that NJS01* is rendered nonextendible upon the incorporation of an adenosine tetraphosphate terminator nucleotide of the invention.

Example V

Automated Cycle DNA Sequencing Using a
Modified Thermostable DNA Polymerase and
Fluorescent Primers This example illustrates the application of the 2'-terminator nucleotides of the invention to automated dye primer cycle DNA sequencing. In particular, an M13mp18 DNA template was sequenced using ribonucleoside 2'-monophosphate 5'-triphosphates.

Cycle sequencing reactions were performed with G46E E678G CS5 DNA polymerase (referred to above) modified for the incorporation of ribonucleotide analogs, dye primers, and ribonucleoside 2'-monophosphate 5'-triphosphate analogs. Reactions consisted of 50 mM Tricine pH 8.5; 40 mM KOAc; 4 mM Mg(OAc)$_2$; 100 μM each dATP, dCTP, dTTP; 150 μM c7dGTP; 0.5 unit/μl G46E E678G CS5 DNA polymerase; 1.0 unit/μl rTth Thermostable Pyrophosphatase; and 20 ng/μl M13mp18 template. Four individual reactions, one for each base were performed. Reactions for each of the bases contained the above plus the following reagents:

ADENOSINE REACTIONS (10 μL):
3.5 μM Adenosine 2'-monophosphate 5'-triphosphate
0.1 μM FR686NHEX primer
CYTIDINE REACTIONS (10 μL):
7.5 μM Cytidine 2'-monophosphate 5'-triphosphate
0.1 μM FR686NFAM primer GUANOSINE REACTIONS (20 µL):
5 µM Guanosine 2'-monophosphate 5'-triphosphate
0.1 µM FR686NTAMRA primer
URIDINE REACTIONS (20 µL):
10 µM Uridine 2'-monophosphate 5'-triphosphate
0.1 µM FR686NROX primer In the adenosine reactions, the adenosine 2'-monophosphate 5'-triphosphate was approximately 95% pure (i.e., about 5% was the adenosine 3'-monophosphate 5'-triphosphate). In the cytidine reactions, the cytidine 2'-monophosphate 5'-triphosphate and the cytidine 3'-monophosphate 5'-triphosphate were present as 50/50 mixture. In the guanosine reactions, the guanosine 2'-monophosphate 5'-triphosphate was approximately 94% pure (i.e., about 6% was the guanosine 3'-monophosphate 5'-triphosphate). In the uridine reactions, the uridine 2'-monophosphate 5'-triphosphate was 100% pure.

The oligonucleotide primer sequences were, as follows:

```
FR686NFAM   FCGCCAGGGTTTTCCCAGTEA
            E = 2'-amino (ribo) C F = 5' FAM ABD
            (SEQ ID NO: 1)

FR686NHEX   ICGCCAGGGTTTTCCCAGTEA
            E = 2'-amino (ribo) C I = 5' HEX ABD
            (SEQ ID NO: 2)

FR686NROX   JCGCCAGGGTTTTCCCAGTEA
            E = 2'-amino (ribo) C J = 6-ROX
            (SEQ ID NO: 3)

FR686NTAMRA LCGCCAGGGTTTTCCCAGTEA
            E = 2'-amino (ribo) C L = C6-amino TAMRA
            (SEQ ID NO: 4)
```

Each of the four reactions were placed in a Perkin-Elmer GeneAmp® PCR system 9600 thermal cycler and subjected to 95° C. for 45 seconds and then 20 cycles of 95° C. for 15 seconds, 55° C. for 15 seconds, 70° C. for 90 seconds, followed by 20 cycles of 95° C. for 15 seconds, 70° C. for 90 seconds. The four reactions were pooled and precipitated by the addition of 144 µl 100% ethanol and 6 µl 3M NaOAc (pH 5.2) at 4° C. for 15 minutes. The pooled reactions were microcentrifuged at 4° C. for 15 minutes to precipitate the DNA, and the supernatant was removed. The pellet was washed with 350 µl cold 70% ethanol, microcentrifuged at 4° C. for 5 minutes, supernatant removed, and the DNA pellet dried. The precipitated DNA was resuspended in 10 µl Hi-Di formamide (Applied Biosystems, Foster City, Calif., part #4311320), heated at 90° C. for 3 minutes and placed on ice. 2 µl of each sample was loaded onto a pre-electrophoresed 48 cm 4.25% acrylamide:bis (29:1), 6 M urea gel and electrphoresed for 7 hours on an ABI PRISM™ 377 DNA Sequencer (Applied Biosystems, Foster City, Calif.).

Figure 21:
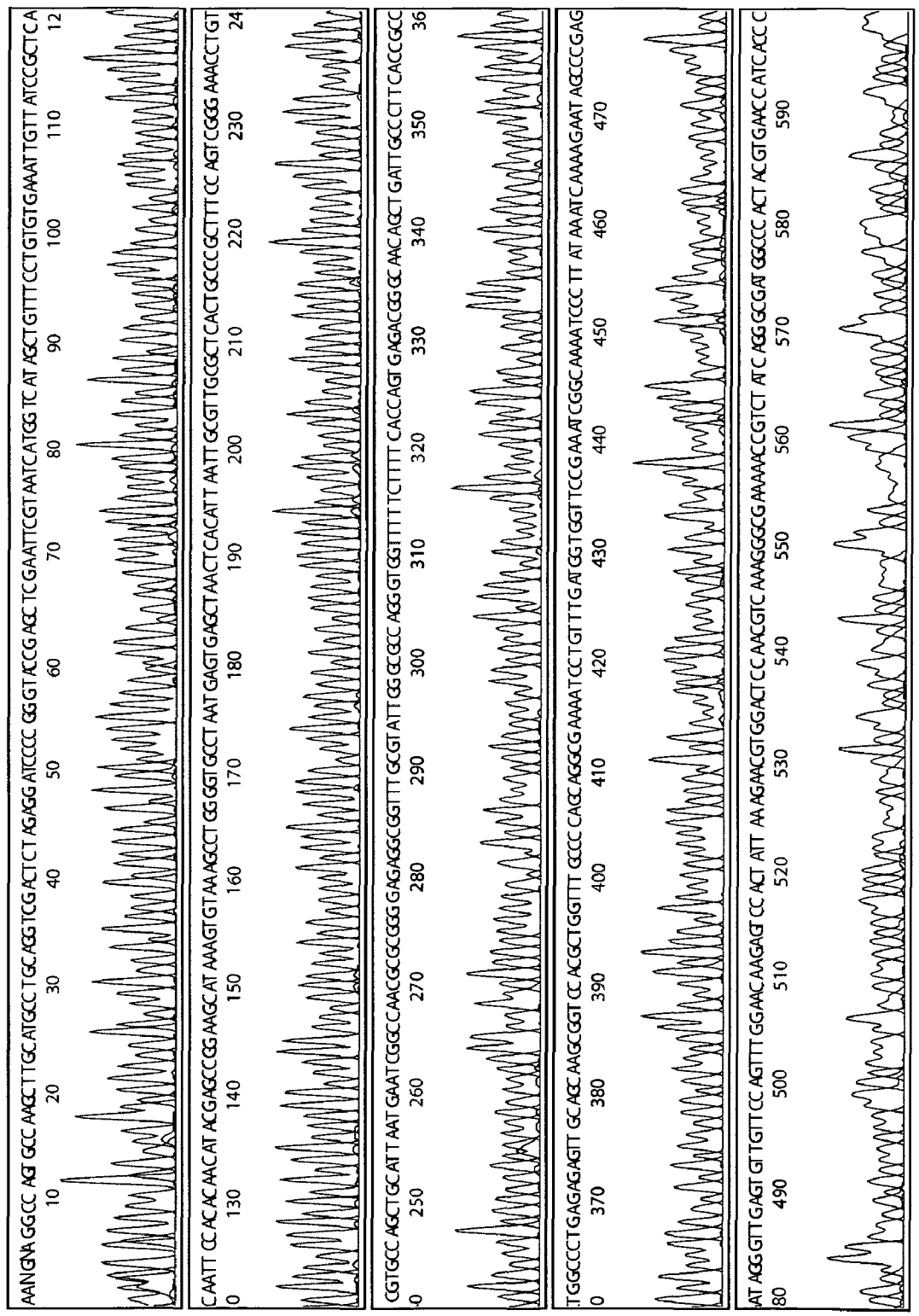
FIG. 21 is a spectral profile that shows the data from a sequence analysis of an M13mp18 DNA template using 2'-terminator nucleotides (SEQ ID NOS 30-34, respectively in order of appearance).

Data was analyzed with Sequencing Analysis Software 3.4.1 (Applied Biosystems, Foster City, Calif.) using primer file DP4% Ac{KS}, the semiadaptive basecaller version 3.3.1b2, and a matrix file specific for the dye primers used above generated following the procedure in the Applied Biosystems manual (part # 903436). Automated basecalling by the analysis software was 100% accurate for bases +18 to +739 from the sequencing primer when compared to an M13mp18 reference sequence. FIG. 21 provides a spectral profile of the data from this sequence analysis.

Example VI

Cycled DNA Primer Extension Using a Modified Thermostable DNA Polymerase and Dye-Labeled Ribonucleoside 2'-Monophosphate 5'-Triphosphate A thermal cycled primer extension reaction was performed with G46E E678G CS5 DNA polymerase modified for the incorporation of ribonucleotide analogs, unlabeled primer, and TAMRA dye-labeled uridine 2'-monophosphate 5'-triphosphate. The 20 µl reaction consisted of 50 mM Tricine pH 7.5; 25 mM KOAc; 2.5 mM Mg(OAc)$_2$; 100 µM each dATP, dCTP, and dTTP; 150 µM dITP; 0.5 unit/µl G46E E678G CS5 DNA polymerase; 1.0 unit/µl rTth Thermostable inorganic pyrophosphatase; 5 ng/µl M13mp18 template; 0.15 µM primer; and 0.25 µM TAMRA-uridine 2'-phosphate 5'-triphosphate.

A control reaction was performed with AmpliTaq DNA polymerase, FS, unlabeled primer and TAMRA dye-labeled ddTTP. The 20 µl reaction consisted of 50 mM Tris pH 9; 2 mM MgCl$_2$; 100 µM each dATP, dCTP, and dTTP; 150 µM dITP; 0.5 unit/µl AmpliTaq DNA polymerase, FS; 1.0 unit/µl rTth Thermostable inorganic pyrophosphatase; 5 ng/µl M13mp18 template; 0.15 µM FR686N primer; and 0.2 µM TAMRA-ddTTP.

```
FR686N      CGCCAGGGTTTTCCCAGTEA
            (SEQ ID NO: 5)

E = 2'-amino (ribo) C
```

The reactions were placed in a Perkin-Elmer GeneAmp® PCR system 9700 thermal cycler and subjected to 96° C. for 20 seconds and then 25 cycles of 96° C. for 10 seconds, 50° C. for 5 seconds, 60° C. for 4 minutes. After cycling unincorporated dye-labeled terminator was removed from the reaction by centrifugation at 700×g for two minutes through a Sephadex-G50 column (Sigma, Part No G-50-80). The sample was heated at 95° C. for 3 minutes and placed on ice. The samples were electrophoresed on an Applied Biosystems 3100 Genetic Analyzer with the GeneScan application following the StdSeq50_POP6DefaultModule parameters using a 50 cm capillary array and POP6 polymer.

Figure 22:
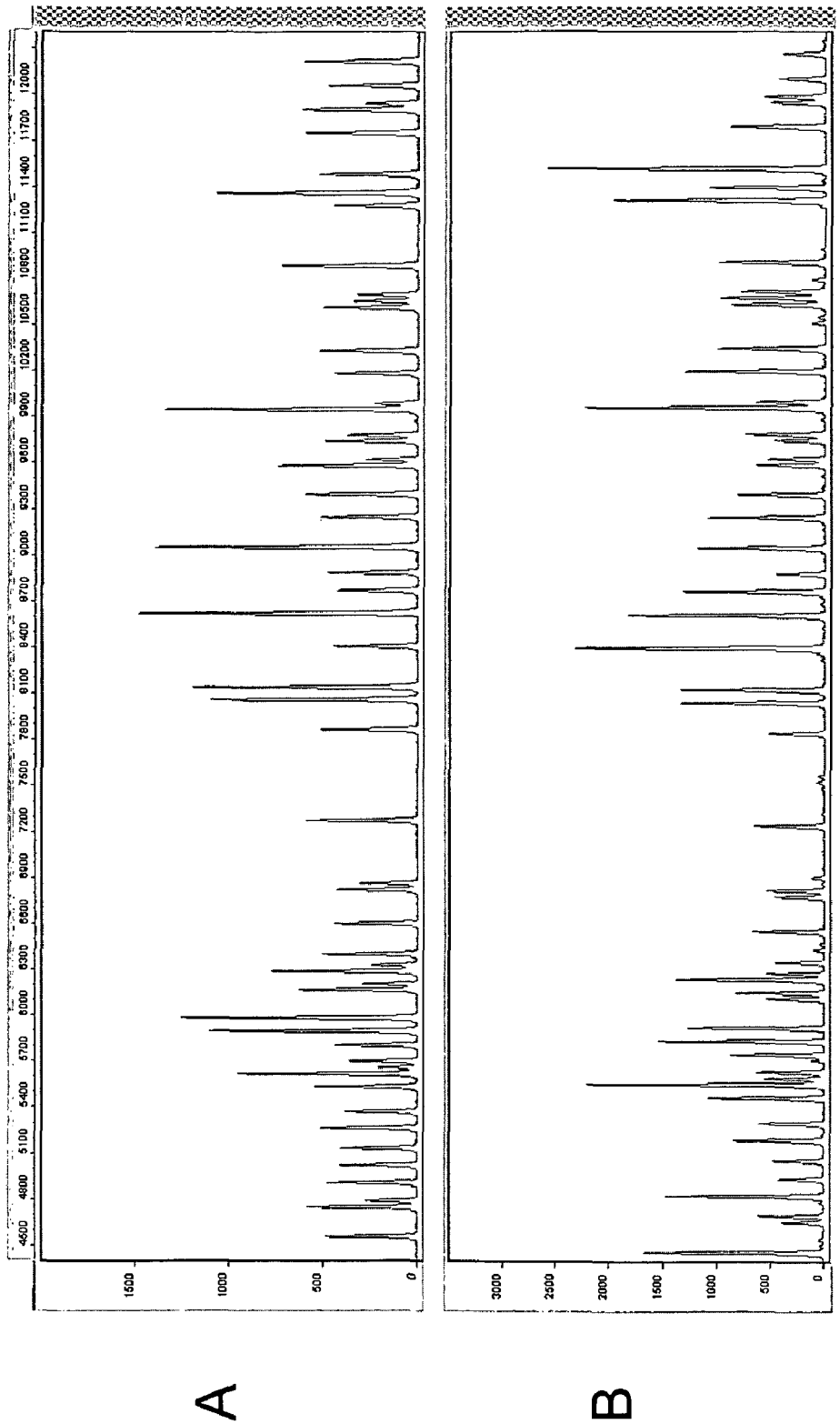
FIGS. 22A and B are spectral profiles that show the data from a sequence analysis of an M13mp18 DNA template using an unlabeled primer and a fluorescent dye-labeled 2'-terminator nucleotide.

Data was analyzed with Applied Biosystems GeneScan 3.7 fragment analysis software. FIG. 22 shows the fragment pattern for T peaks 77 to 273 bases from primer FR686N. More specifically, comparison of the fragment pattern generated with G46E E678G CS5 DNA polymerase and TAMRA-uridine 2'-monophosphate 5'-triphosphate (panel B) to the fragment pattern generated with the control AmpliTaq DNA Polymerase, FS and TAMRA-ddTTP (panel A) revealed a similar pattern of peaks.

Example VII

Synthesis of Blocked Oligonucleotides

Figure 25:
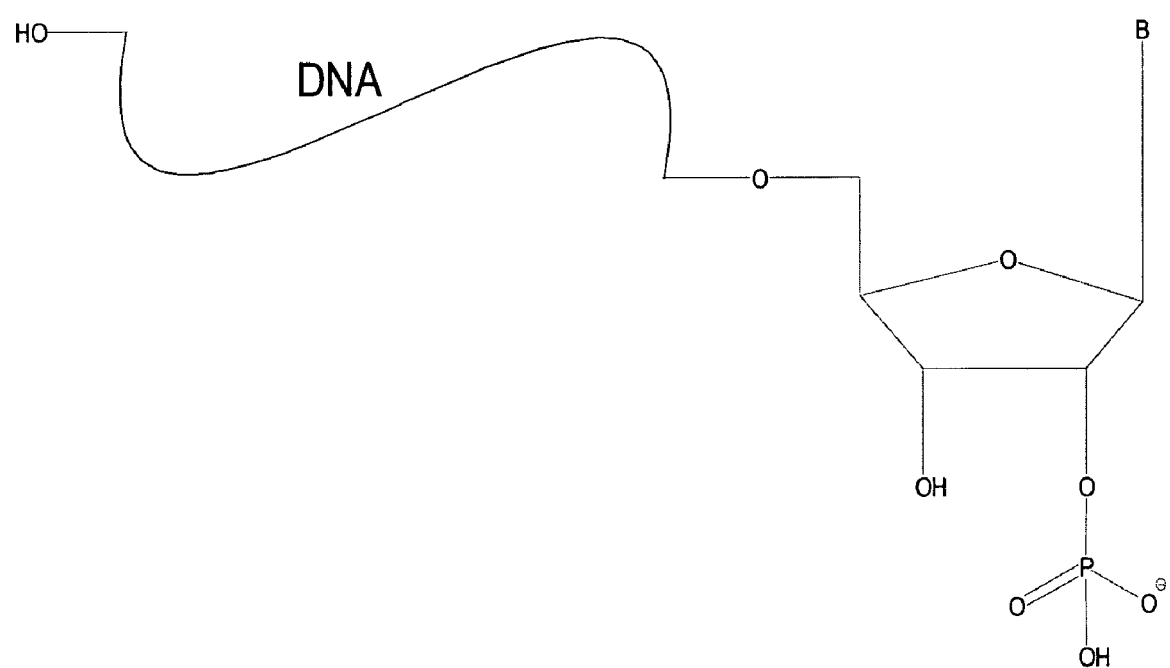
FIG. 25 schematically illustrates a blocked oligonucleotide according to one embodiment of the invention.
Figure 26:
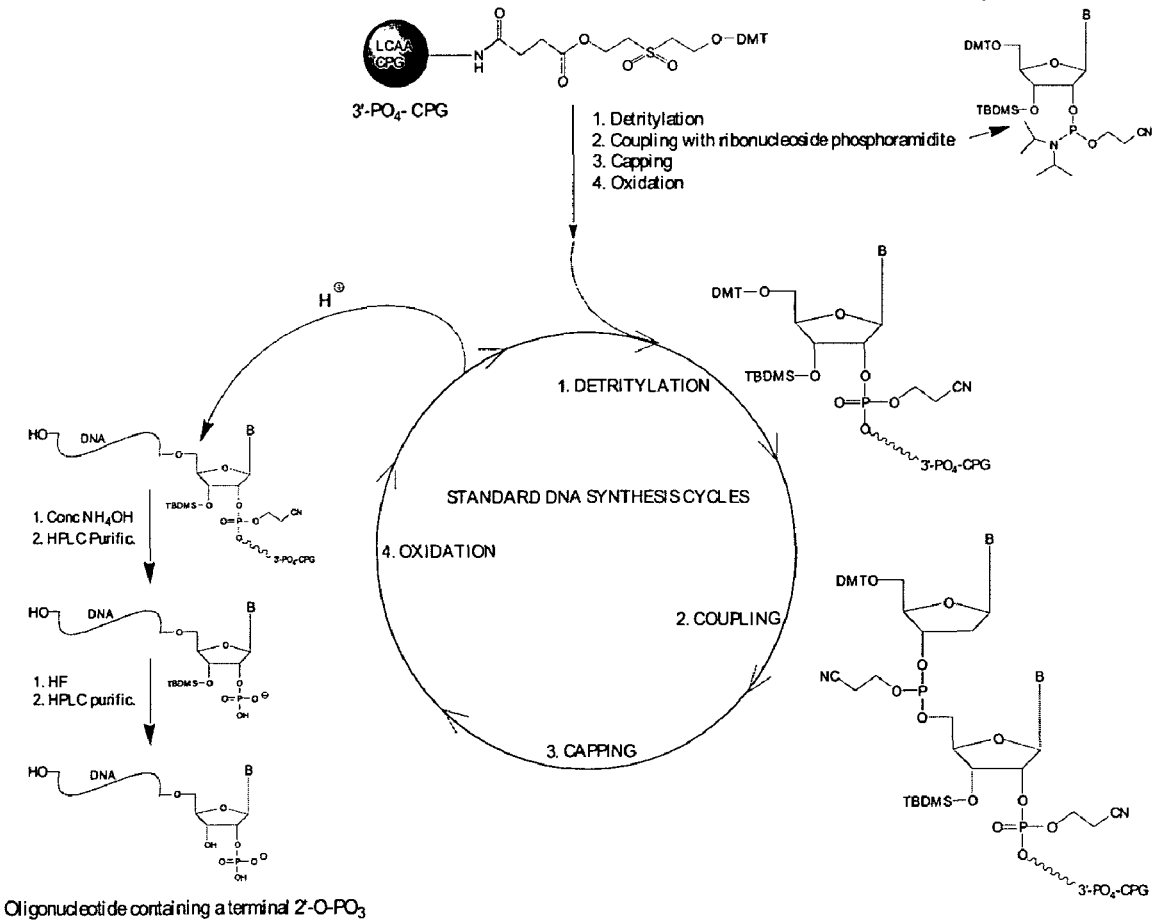
FIG. 26 schematically shows a solid-phase synthesis pathway for blocked oligonucleotides according to one embodiment of the invention.
Figure 27:
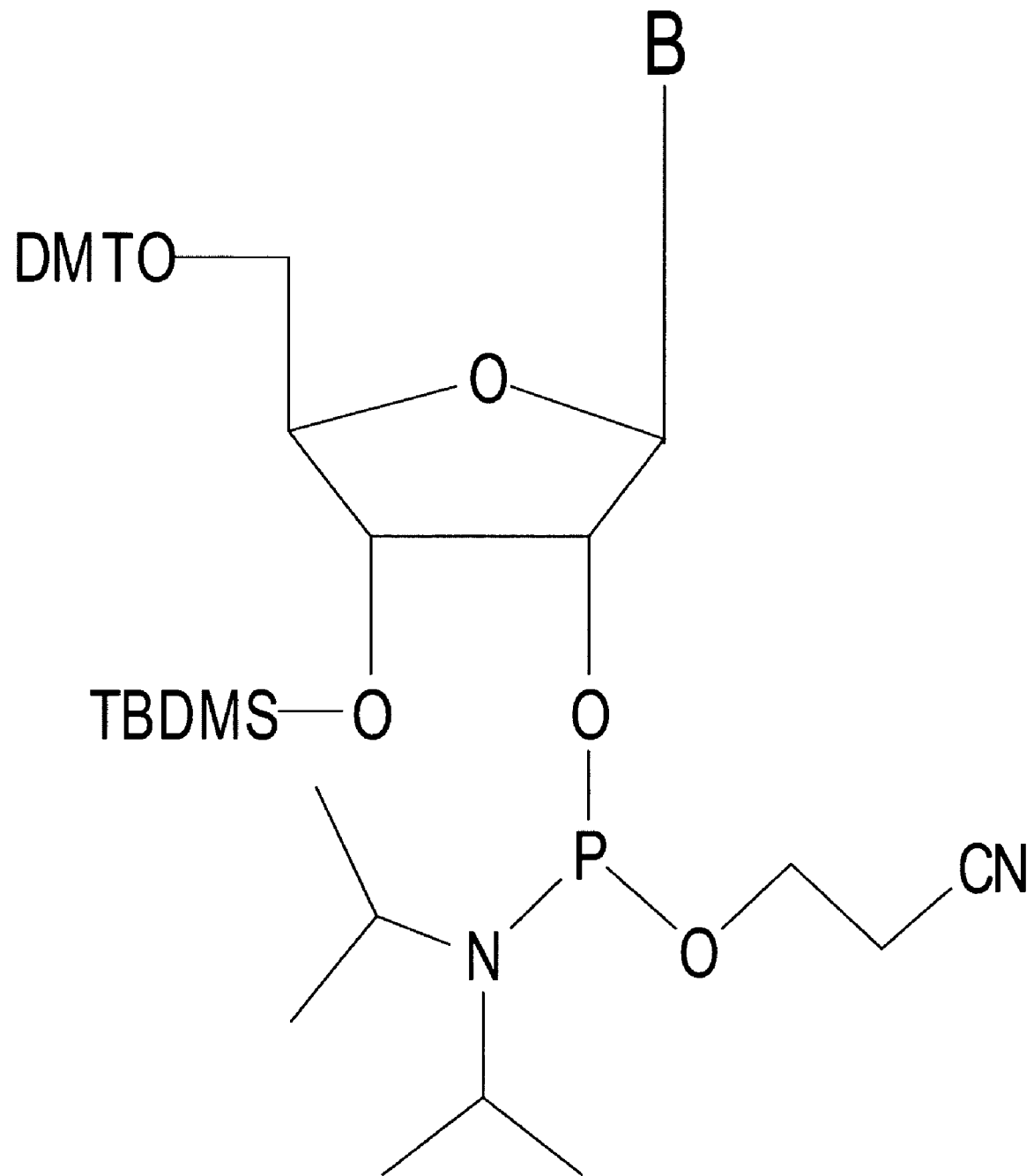
FIG. 27 schematically depicts a 3'-O-TBDMS-2'-O-phosphoramidite.

2'-O—PO$_3$ blocked oligonucleotides (FIG. 25) were synthesized on an automated Applied Biosystems 394 synthesizer using standard β-cyanoethylphosphoramidite chemistry (FIG. 26). The solid support used in the synthesis of these oligonucleotides was 3'-phosphate CPG (from Glen Research, # 20-2900-41), which facilitated the introduction of a phosphate group at the 3'-end of an oligonucleotide. In the first cycle of the synthesis, the ribonucleoside-2'-O-phosphoramidite (FIG. 27, where B=Bases; Adenosine (part # ANP-5681), Cytidine (ANP-5682), Guanosine (ANP-5683) and Uridine (ANP-5684)) purchased from ChemGenes, was used to couple with solid-support. In the second cycle of the synthesis and thereafter, the standard deoxynucleoside phosphoramidites were used. After the synthesis, the oligonucleotides were cleaved from the solid support and deprotected with concentrated ammonium hydroxide at room temperature for 24 to 48 hours. The ammonium hydroxide was then removed by size exclusion chromatography (NAP-10 column; elution with sterile water). The oligonucleotides were then purified by reversed-phase HPLC (PRP-1 column, triethyl ammonium acetate—acetonitrile buffer). The purified oligonucleotides were concentrated and then treated with potassium fluoride to remove the silyl protection of 3'-hydroxyl group at the 3'-end of oligonucleotide. The oligonucleotides were further purified by RP-HPLC (Xterra SB-18 column). The purity and identity of these oligonucleotides was confirmed by ion-exchange HPLC (Dionex, pH 8.0 at 60° C.) and LC-MS analysis.

Example VIII

HIV DNA Template Titrations

Figure 28:
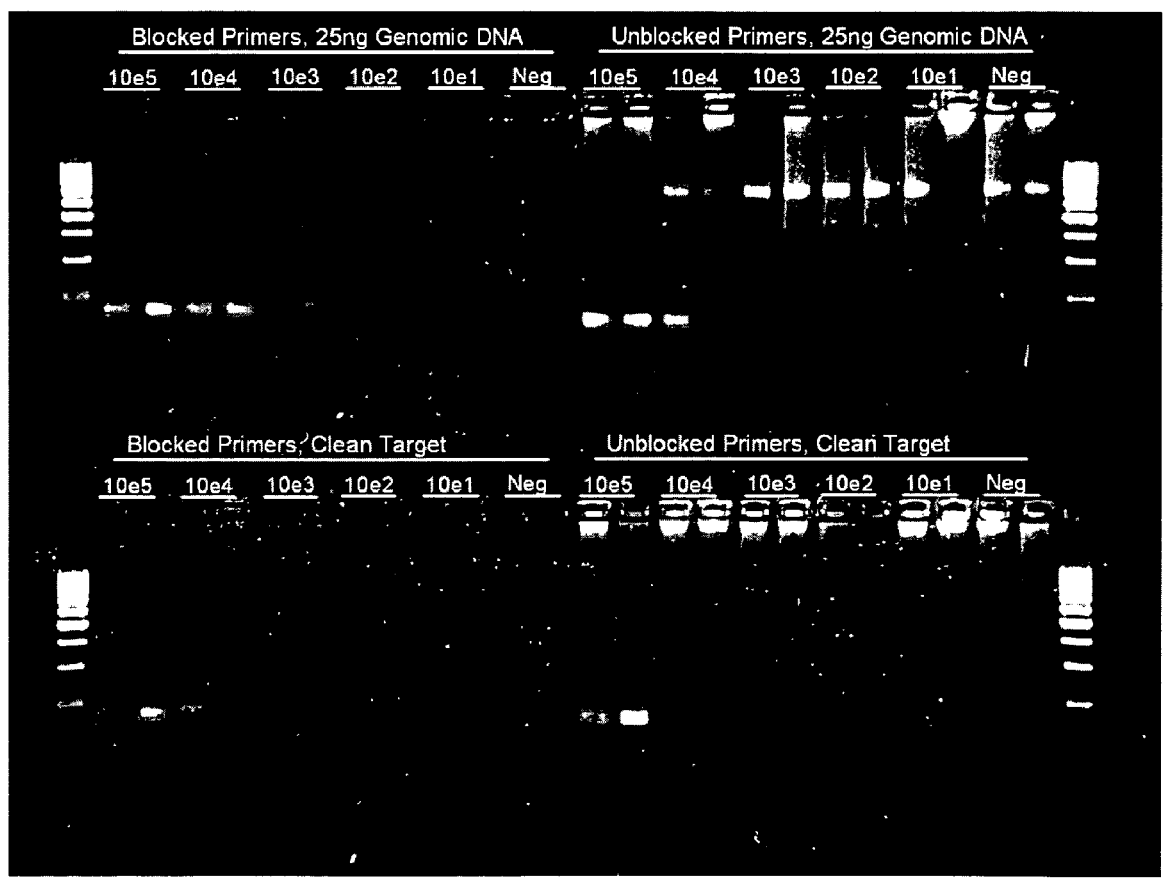
FIG. 28 is a photograph of a gel that shows the detection of PCR products from an analysis that involved PAP-related HIV DNA template titrations.

PAP-related HIV DNA template titrations were performed with and without the presence of genomic DNA. FIG. 28 is a photograph of a gel that shows the detection of the PCR products under the varied reaction conditions utilized in this analysis. This data illustrates, e.g., the improved amplification specificity and sensitivity that can be achieved using the blocked primers described herein relative to reactions not using those primers.

More specifically, the reactions were performed using an ABI 5700 Sequence Detection System with the following temperature profile:
50° C. 2 minutes
93° C. 1 minute
93° C., 15 seconds→52° C., 4 minutes×4 cycles
90° C., 15 seconds→55° C., 4 minutes×56 cycles
The following reaction conditions were common to all reactions:

| Master Mix Components | conc. |
|---|---|
| Tricine (pH 8.0) | 100 mM |
| dATP | 200 μM |
| dCTP | 200 μM |
| dGTP | 200 μM |
| dTTP | 30 μM |
| dUTP | 300 μM |
| Primer 3 or Primer 1 | 200 nM |
| Primer 4 or Primer 2 | 200 nM |
| KOAc | 110 mM |
| SYBR Green I | 0.2X |
| NaPPi | 225 μM |
| Mg(OAc)$_2$ | 2.5 mM |
| Tth Storage Buffer (0.2% Tween) | 6% v/v |
| GLQDSE CS5 DNA polymerase | 10 nM |

Note, that "GLQDSE CS5 DNA polymerase" refers to a G46E L329A Q601R D640G S671F E678G CS5 DNA polymerase. Note further, that the "Tth Storage Buffer" included 0.2% Tween 20, 20 mM Tris pH 8.0, 0.1 mM EDTA, 100 nM KCl, 1 mM DTT, and 50% v/v glycerol. In addition, each reaction volume was brought to 50 μl with diethylpyrocarbonate (DEPC) treated water.

The varied reaction components included the following unblocked primers (see, the reactions denoted "unblocked primers" in FIG. 28):

```
Primer 1  5'-TGAGACACCAGGAATTAGATATCAGTACAATGT-3'
          (SEQ ID NO: 6)

Primer 2  5'-CTAAATCAGATCCTACATATAAGTCATCCATGT-3'
          (SEQ ID NO: 7)
``` and the following blocked primers (see, the reactions denoted "blocked primers" in FIG. 28):

```
Primer 3  5'-TGAGACACCAGGAATTAGATATCAGTACAATGU*-3'
          (SEQ ID NO: 8)

Primer 4  5'-CTAAATCAGATCCTACATATAAGTCATCCATGU*-3'
          (SEQ ID NO: 9)
``` where U* refers to a 2'-Phosphate-U (i.e., a 2')-terminator nucleotide comprising a phosphate group at the 2' position). The reactions also either included (see, the reactions denoted "25ng Genomic DNA" in FIG. 28) or lacked (see, the reactions denoted "Clean Target" in FIG. 28) 25 ng of human genomic DNA added to the mixtures. As further shown in FIG. 28, the reactions also included $10^5$, $10^4$, $10^3$, $10^2$, or $10^1$ copies of linearized plasmid DNA, which included the target nucleic acid, diluted in 1μl HIV Specimen Diluent (10 mM Tris, 0.1 mM EDTA, 20 μg/mL Poly A, and 0.09% NaN$_3$) or 1 μl HIV Specimen Diluent in "Neg" reactions. The indicated primer pairs amplified a 170 base pair product from the plasmid DNA.

Example IX

Figure 29:
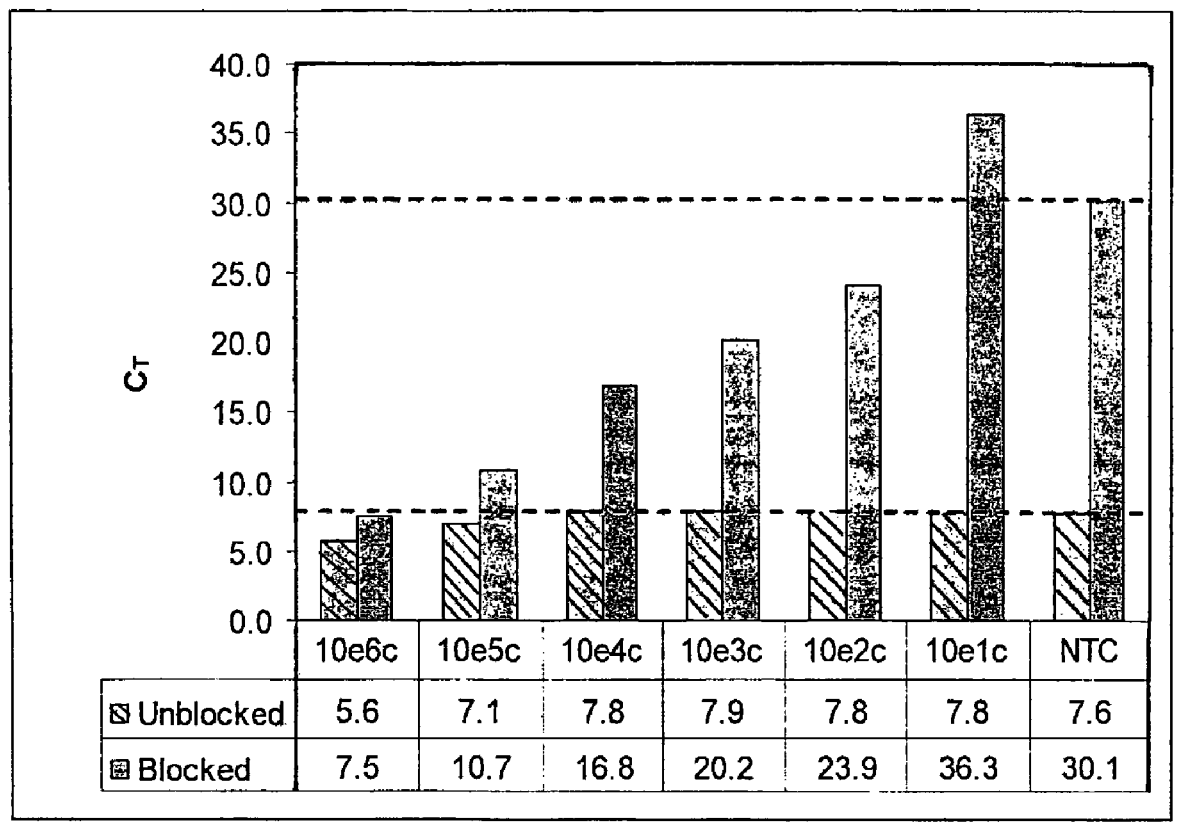
FIG. 29 is a graph that shows threshold cycle ($C_T$) values observed for various mutant K-Ras plasmid template copy numbers utilized in amplifications that involved blocked or unblocked primers.

Amplification of Mutant K-Ras Plasmid Template in a Background of Wild-Type K-Ras Plasmid Template Amplifications involving various copy numbers of mutant K-Ras plasmid template in a background of wild-type K-Ras plasmid template and comparing blocked and unblocked primers were performed. FIG. 29 is a graph that shows threshold cycle ($C_T$) values (y-axis) observed for the various mutant K-Ras plasmid template copy numbers (x-axis) utilized in these reactions. FIG. 29 further illustrates, e.g., the improved discrimination that can be achieved using the blocked primers described herein.

The reactions were performed using an ABI 5700 Sequence Detection System with the following temperature profile:
50° C. 2 minutes
93° C. 1 minute
92° C., 15 seconds→65° C., 2 minutes×60 cycles
The following reaction conditions were common to all reactions:

| Master Mix Components | conc. |
|---|---|
| Tricine (pH 8.0) | 100 mM |
| dATP | 200 μM |
| dCTP | 200 μM |
| dGTP | 200 μM |
| dTTP | 30 μM |
| dUTP | 300 μM |
| Primer 7 or Primer 5 | 200 nM |
| Primer 8 or Primer 6 | 200 nM |
| SYBR Green I | 0.1X |
| NaPPi | 225 μM |
| Mg(OAc)$_2$ | 2.5 mM |
| Ung | 2 U |
| Tth Storage Buffer (0.2% Tween) | 6% v/v |
| GDSE CS5 DNA polymerase | 5 nM |
| Linearized Wild-Type Plasmid DNA | $10^6$ copies |

Note, that "GDSE CS5 DNA polymerase" refers to a G46E D640G S671F E678G CS5 DNA polymerase. In addition, each reaction volume was brought to 50 μl with DEPC treated water.

The varied reaction components included the following unblocked primers (see, the reactions denoted "unblocked" in FIG. 29):

```
Primer 5    5'-AAACTTGTGGTAGTTGGAGCTC-3'
            (SEQ ID NO: 10)

Primer 6    5'-GTTGGATCATATTCGTCCACAA-3'
            (SEQ ID NO: 11)
``` and the following blocked primers (see, the reactions denoted "blocked" in FIG. 29):

```
Primer 7    5'-AAACTTGTGGTAGTTGGAGCTC*-3'
            (SEQ ID NO: 12)

Primer 8    5'-GTTGGATCATATTCGTCCACAA*-3'
            (SEQ ID NO: 13)
``` where C* refers to a 2'-Phosphate-C and A* refers to a 2'-Phosphate-A (i.e., 2'-terminator nucleotides comprising phosphate groups at 2' positions). In addition, $10^6$, $10^5$, $10^4$, $10^3$, $10^2$, $10^1$ or 0 copies (NTC reactions) (10e6c, 10e5c, 10e4c, 10e3c, 10e2c, 10e1c, and NTC, respectively, in FIG. 29) of linearized mutant K-Ras plasmid DNA were added to the reactions. The relevant subsequences of the mutant plasmid DNA were perfectly matched to both the blocked and unblocked primer sets. Further, the mutant K-Ras plasmid DNA was diluted in 1 µHIV Specimen Diluent (see, above) or 1 µl HIV Specimen Diluent (see, above) in "NTC" reactions. Additionally, $10^6$ copies of linearized wild-type K-Ras plasmid DNA were present in all reactions. The wild-type K-Ras plasmid DNA was identical in sequence to mutant plasmid DNA except that it creates a C:C mismatch with the ultimate 3' base (dC) in primers 5 and 7. Both blocked and unblocked primer pairs created a 92 base pair amplicon on the mutant linearized plasmid template.

Example X

Figure 30:
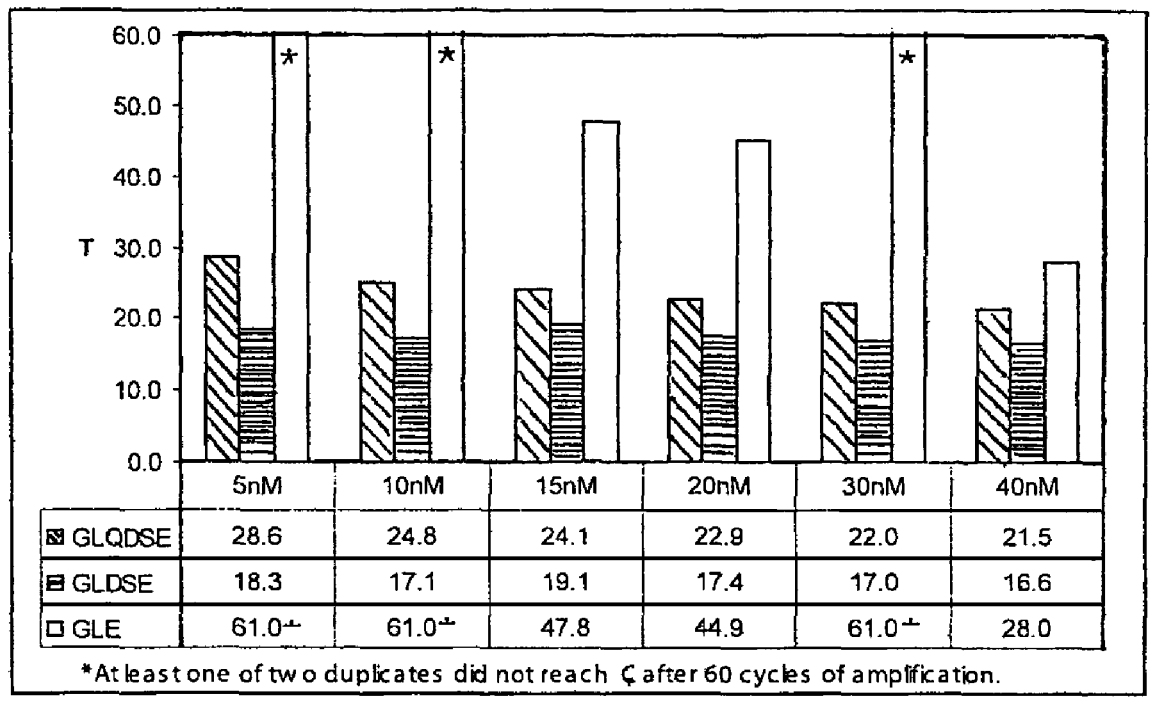
FIG. 30 is a graph that shows threshold cycle ($C_T$) values observed for various enzymes and enzyme concentrations utilized in amplifications that involved a K-Ras plasmid template.

Amplification of K-Ras Plasmid Template With Various Enzymes at Varied Concentrations Amplifications involving K-Ras plasmid template with various enzymes at varied concentrations were performed. FIG. 30 is a graph that shows threshold cycle ($C_T$) values (y-axis) observed for the various enzymes and concentrations (x-axis) utilized in these reactions. The reactions were performed using an ABI 5700 Sequence Detection System with the following temperature profile:

50° C. 2 minutes
93° C. 1 minute
92° C., 15 seconds →60° C., 2 minutes ×60 cycles The following reaction conditions were common to all reactions:

| Master Mix Components | conc. |
|---|---|
| Tricine (pH 8.0) | 100 mM |
| dATP | 200 µM |
| dCTP | 200 µM |
| dGTP | 200 µM |
| dTTP | 30 µM |
| dUTP | 300 µM |
| Primer 9 | 200 nM |
| Primer 10 | 200 nM |
| SYBR Green I | 0.1X |

| Master Mix Components | conc. |
|---|---|
| NaPPi | 225 µM |
| Mg(OAc)$_2$ | 2.5 mM |
| Ung | 2 U |
| Tth Storage Buffer (0.2% Tween) | 6% v/v |
| Linearized K-Ras Plasmid DNA | $10^4$ copies |

The reaction components included the following blocked primers:

```
Primer 9     5'-AAACTTGTGGTAGTTGGAGCTGU*-3'
             (SEQ ID NO: 14)

Primer 10    5'-GTTGGATCATATTCGTCCACAA*-3'
             (SEQ ID NO: 15)
``` where U* refers to a 2'-Phosphate-U and A* refers to a 2'-Phosphate-A (i.e., 2'-terminator nucleotides comprising phosphate groups at 2' positions). The primer pairs created a 92 base pair amplicon on the linearized K-Ras plasmid template. In addition, each reaction volume was brought to 50 µl with diethylpyrocarbonate (DSPC) treated water.

The polymerase concentration and KOAc concentrations were optimized for each individual polymerase as follows:

| Polymerase | Polymerase Conc. (nM) | KOAc (mM) |
|---|---|---|
| GLQDSE | 5, 10, 15, 20, 30, or 40 nM | 110 |
| GLDSE | 5, 10, 15, 20, 30, or 40 nM | 25 |
| GLE | 5, 10, 15, 20, 30, or 40 nM | 25 |

Note, that "GLQDSE" refers to a G46E L329A Q601R D640G S671F E678G CS5 DNA polymerase, "GLDSE" refers to a G46E L329A D640G S671F E678G CS5 DNA polymerase, and "GLE" refers to a G46E L329A E678G CS5 DNA polymerase.

Example XI

Pap-Related Enzyme Comparisons

The abilities of G46E L329A E678G CS5 DNA polymerase and G46E L329A D640 S671F E678G CS5 DNA polymerase to perform pyrophosphorolysis activated polymerization ("PAP") were compared. The reaction buffer was comprised of 100 mM Tricine pH 8.0, 0 mM (G46E L329A E678G CS5 DNA polymerase) or 50 mM (G46E L329A D640 S671F E678G CS5 DNA polymerase) KOAc, 10% v/v glycerol, 0.04 U/µl UNG, 4 mM Mg(OAc)$_2$, 0.2× SYBR Green I, 2.5% v/v enzyme storage buffer (50% v/v glycerol, 100 mM KCl, 20 mM Tris pH 8.0, 0.1 mM EDTA, 1 mM DTT, 0.5% Tween 20), 0.2 mM each dATP, dCTP, and dGTP, and 0.4 mM dUTP, and 100 µM pyrophosphate. M13 template (GenBank Accession No. X02513) and enzyme were cross-titrated. M13 concentrations used were 0, $10^4$, $10^5$, and $10^6$ copies per 20 µl reaction. Enzyme concentrations used were 2.5 nM, 5 nM, 10 nM, 15 nM, 20 nM, 25 nM, 35 nM, and 50 nM. Reactions were set up in triplicate in a 384-well thermocycler, using the following cycling parameters: 50° C. for 2 minutes; 90° C. for 1 minute; then 46 cycles of: 90° C. for 15 seconds followed by an extension temperature of 62° C. for 60 seconds.

The primer sequences used were 5'-CGCCTGGTCTGTA-CACCGTTXA-3' (SEQ ID NO: 16) (primer 11) and 5'-GGAACGAGGGTAGCAACGGCTACE-3' (SEQ ID NO: 17) (primer 12), where X=2'-amino-C and E=2'-PO$_4$-A (i.e., a 2'-terminator nucleotide). These primers, added to the reaction mix at 0.1 µM each, result in a 348 by product from M13 template. In order to serve as a primer, primer 12 must be activated by pyrophosphorolytic removal of the terminal residue.

Figure 31:
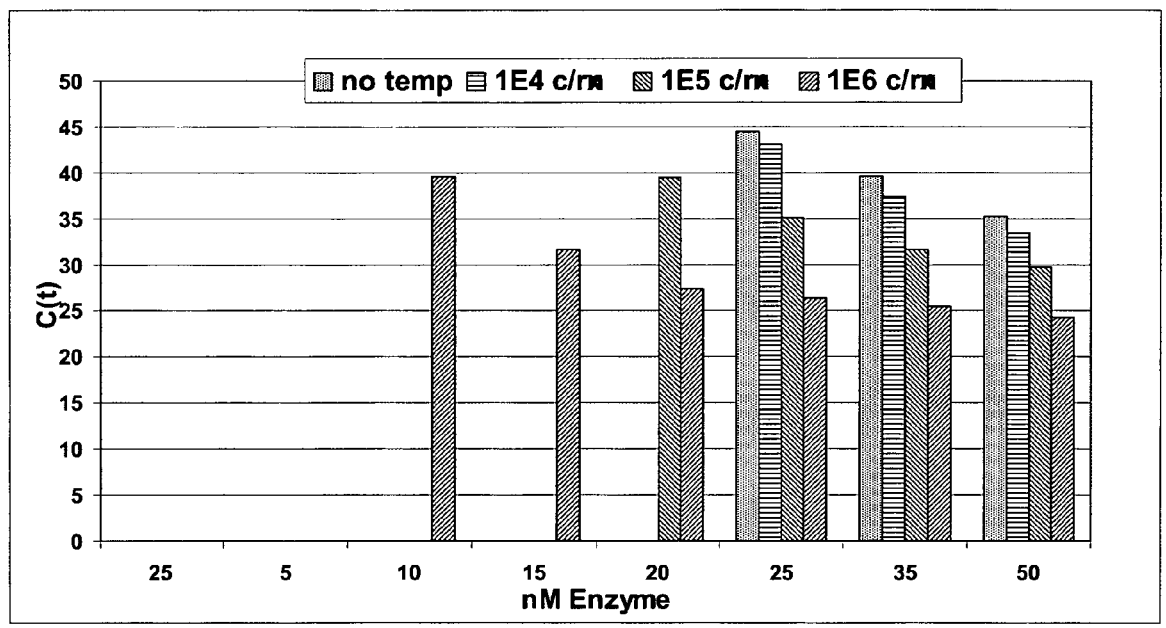
FIG. 31 is a bar graph that shows the effect of enzyme concentration on threshold cycle (Ct) values in pyrophosphorolysis activated polymerization (PAP) reactions utilizing a G46E L329A E678G (GLE) CS5 DNA polymerase. The y-axis represents Ct value, while the x-axis represents the enzyme concentration (nM). The legend that accompanies the plot shows the number of copies of the template nucleic acid corresponding to each trace in the graph (no copies of the template nucleic acid (no temp), $1e^4$ copies of the template nucleic acid (1E4/rxn), $1e^5$ copies of the template nucleic acid (1E5/rxn), and $1e^6$ copies of the template nucleic acid (1E6/rxn)).
Figure 32:
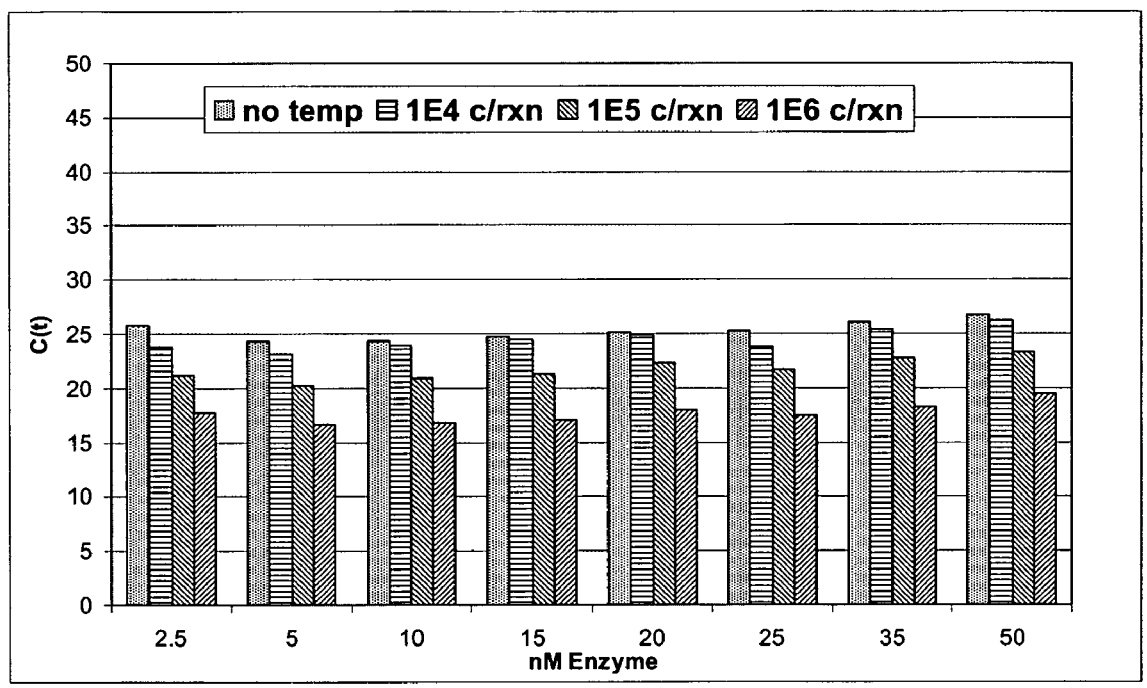
FIG. 32 is a bar graph that shows the effect of enzyme concentration on threshold cycle (Ct) values in pyrophosphorolysis activated polymerization (PAP) reactions utilizing a G46E L329A D640G S671F E678G (GLDSE) CS5 DNA polymerase. The y-axis represents Ct value, while the x-axis represents the enzyme concentration (nM). The legend that accompanies the plot shows the number of copies of the template nucleic acid corresponding to each trace in the graph (no copies of the template nucleic acid (no temp), $1e^4$ copies of the template nucleic acid (1E4/rxn), $1e^5$ copies of the template nucleic acid (1E5/rxn), and $1e^6$ copies of the template nucleic acid (1E6/rxn)).

Fluorescence data was analyzed to determine elbow values (i.e., C(t) (emergence of fluorescence over baseline)). C(t) values for G46E L329A E678G CS5 DNA polymerase are shown in FIG. 31. C(t) values for G46E L329A D640G S671F E678G CS5 DNA polymerase are shown in FIG. 32.

Example XII

Hepatitis C Virus (HCV) RNA to CDNA Reverse Transcription (RT) Comparing Unblocked and Blocked RT Primers The extension of an unblocked HCV RT primer was compared to the extension of a blocked primer on an HCV RNA template in reverse transcription reactions. These RT comparisons were performed using various polymerases. To illustrate, FIG. 33 is a graph that shows threshold cycle (Ct) values (y-axis) observed for the various enzymes (x-axis) utilized in these reactions in which the cDNA was measured using real-time PCR involving 5'-nuclease probes.

The following reaction conditions were common to all RT reactions:

| RT Mix Component | Concentration |
| --- | --- |
| Tricine pH 8.0 | 100 mM |
| KOAc | 100 mM |
| DMSO | 4% (v/v) |
| Primer 1 or 2 | 200 nM |
| dATP | 200 µM |
| dCTP | 200 µM |
| dGTP | 200 µM |
| dTTP | 30 µM |
| dUTP | 300 µM |
| UNG | 0.2 Unit |
| Mn(OAc)$_2$ | 1 mM |
| PPi | 175 uM |

Figure 33:
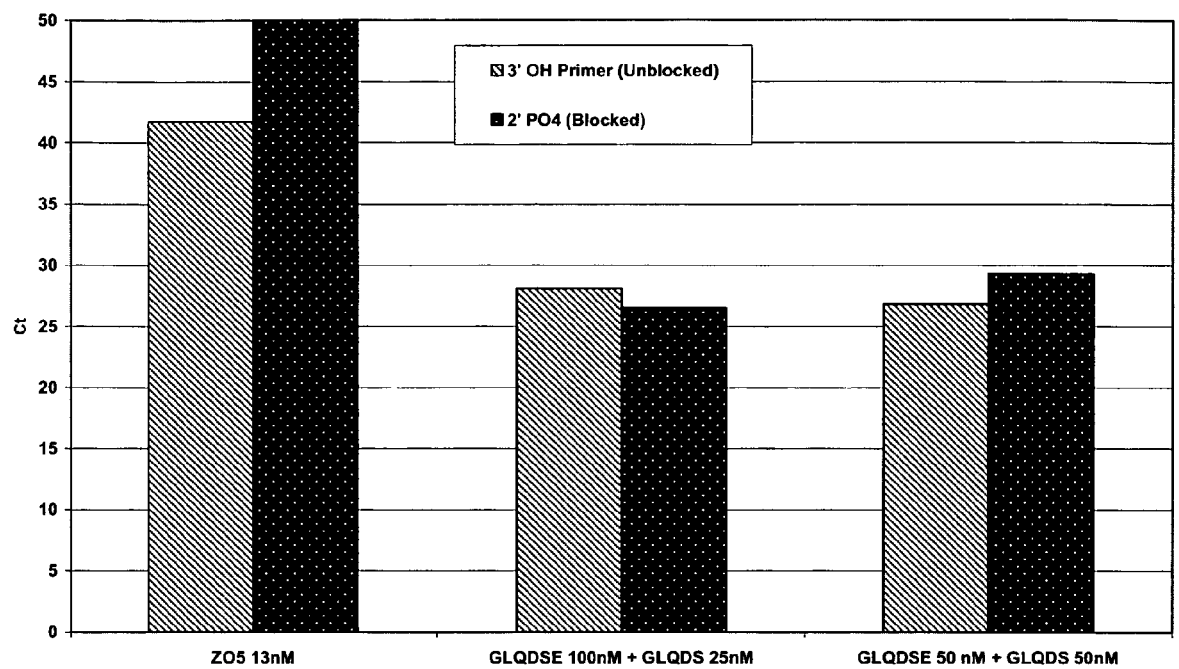
FIG. 33 is a bar graph that shows data for PAP reverse transcription reactions on HCV RNA in which products of the cDNA reaction were measured using a quantitative PCR assay specific for the HCV cDNA. The y-axis represents Ct value, while the x-axis represents the Units of enzyme utilized in the reactions. As indicated, the enzymes used in these reactions were Z05 DNA polymerase (Z05) or blends of G46E L329A Q601R D640G S671F E678G (GLQDSE) and G46E L329A Q601R D640G S671F (GLQDS) CS5 DNA polymerases.

The varied reaction components included the following 3'-OH unblocked primer (see, the reactions denoted "3' OH Primer (Unblocked)" in FIG. 33):

```
Primer 1   5'-GCAAGCACCCTATCAGGCAGTACCACAA-3'
           (SEQ ID NO: 18)
``` and the following blocked primer (see, the reactions denoted "2' PO4 (Blocked)" in FIG. 33):

```
Primer 2   5'-GCAAGCACCCTATCAGGCAGTACCACAA*-3'
           (SEQ ID NO: 19)
``` where A* refers to a 2'-Phosphate-A or a 2'-monophosphate-3'-hydroxyl adenosine nucleotide (i.e., 2' terminator nucleotide comprising a phosphate group at the 2' position). Further, the following polymerase conditions were compared in the cDNA reactions (see, FIG. 33):
Z05 DNA polymerase (13 nM)
GLQDSE CS5 DNA polymerase (100 nM) combined with GLQDS CS5 DNA polymerase (25 nM)
GLQDSE CS5 DNA polymerase (50 nM) combined with GLQDS CS5 DNA polymerase (50 nM
where "GLQDSE CS5 DNA polymerase" refers to a G46E L329A Q601R D640G S671F E678G CS5 DNA polymerase and "GLQDS CS5 DNA polymerase" refers to a G46E L329A Q601R D640G S671F CS5 DNA polymerase. In addition, each reaction was brought to 20 µl with diethylpyrocarbonate (DEPC) treated water.

The RT reactions were incubated at 60° C. for 60 minutes in an ABI 9600 Thermal Cycler. After the RT incubation, RT reactions were diluted 100-fold in DEPC treated water. The presence of cDNA was confirmed and quantitated by 5' nuclease probe-based real-time HCV PCR reactions designed to specifically measure the HCV cDNA products of the RT reactions. These reactions were performed using an ABI Prism 7700 Sequence Detector with the following temperature profile:
50° C. 2 minutes
95° C. 15 seconds→60° C. 1 minutes×50 cycles.

Example XIII

Bidirectional Pap for Braf Mutation Detection

Figure 34:
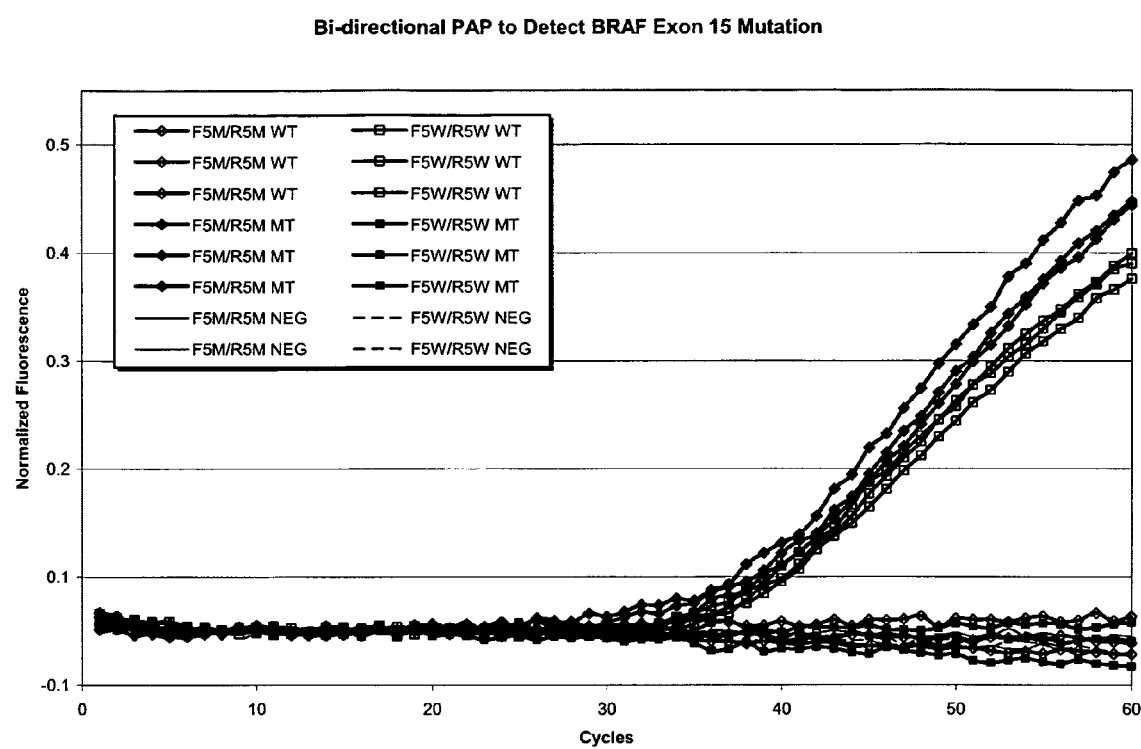
FIG. 34 shows PCR growth curves of BRAF oncogene amplifications that were generated when bidirectional PAP was performed. The x-axis shows normalized, accumulated fluorescence and the y-axis shows cycles of PAP PCR amplification.

FIG. 34 shows PCR growth curves of BRAF oncogene amplifications that were generated when bidirectional PAP was performed. The x-axis shows normalized, accumulated fluorescence and the y-axis shows cycles of PAP PCR amplification. More specifically, these data were produced when mutation-specific amplification of the T→A mutation responsible for the V599E codon change in the BRAF oncogene (see, Brose et al. (2002) *Cancer Res* 62:6997-7000, which is incorporated by reference) was performed using 2'-terminator blocked primers that overlap at their 3'-terminal nucleotide at the precise position of the mutation. When primers specific to wild-type sequence were reacted to wild-type target or mutant target, only wild-type target was detected. Conversely, when primers specific to mutant sequence were reacted to wild-type target or mutant target, only mutant target was detected.

The following reaction conditions were common to all RT reactions:

| Component | Concentration |
| --- | --- |
| Tricine pH 8.0 | 100 mM |
| KOAc | 100 mM |
| Glycerol | 3.5% v/v |
| Primer F5W or F5M | 200 nM |
| Primer R5W or R5M | 200 nM |
| dATP | 200 µM |
| dCTP | 200 µM |
| dGTP | 200 µM |
| dTTP | 30 µM |
| dUTP | 300 µM |
| UNG | 1 Unit |
| PPi | 175 uM |
| GLQDSE | 15 nM |
| SYBR I/carboxyrhodamine | 1/100,000 (0.1x) |
| Mg(OAc)$_2$ | 3.0 mM | where "GLQDSE" refers to a G46E L329A Q601R D640G S671F E678G CS5 DNA polymerase.

The varied reaction components included the following wild-type BRAF primers (labeled "F5W/R5W" in FIG. 34):

```
F5W      5'-AATAGGTGATTTTGGTCTAGCTACAGU*-3'
         (SEQ ID NO: 20)

R5W      5'-GGACCCACTCCATCGAGATTTCA*-3'
         (SEQ ID NO: 21)
``` and the following mutant BRAF primers (labeled "F5M/R5M" in FIG. 34):

```
F5M      5'-AATAGGTGATTTTGGTCTAGCTACAGA*-3'
         (SEQ ID NO: 20)

R5M      5'-GGACCCACTCCATCGAGATTTCU*-3'
         (SEQ ID NO: 21)
``` where A* refers to a 2'-Phosphate-A or a 2'-monophosphate-3'-hydroxyl adenosine nucleotide and U* is a 2'-Phosphate-U or a 2'-monophosphate-3'-hydroxyl uridine nucleotide (i.e., 2' terminator nucleotides comprising a phosphate group at the 2' position).

In addition, each reaction was brought to 50 µl with DEPC treated water. Wild-type reactions (labeled "WT" in FIG. 34) contained linearized DNA plasmid of the BRAF wild-type sequence and mutant reactions (labeled "MT" in FIG. 34) contained linearized DNA plasmid of the BRAF mutant sequence. Negative reactions (labeled "NEG" in FIG. 34) contained HIV specimen diluent (10 mM Tris, 0.1 mM EDTA, 20 µg/mL Poly A, and 0.09% NaN$_3$) with no DNA. Combinations of the primers in PCR produced a 50 bp amplicon. Further, the reactions were performed using an ABI Prism 7700 Sequence Detector with the following temperature profile:

50° C. 1 minute
93° C. 1 minute
90° C. 15 seconds
60° C. 150 seconds→×60 Cycles.

Example XIV

Detection of Fluorescent Pap Release Product

This prophetic example illustrates a real-time monitoring protocol that involves PAP activation in which a blocked primer leads to the production of detectable signal as that primer is activated and extended.

Construction of a 3' Terminated, Dual-Labeled Oligonucleotide Primer:

The primer QX below is a DNA oligonucleotide that includes a quenching dye molecule, Black Hole Quencher® (BHQ) (Biosearch Technologies, Inc.) attached to the thirteenth nucleotide (A) from the 3' terminus.

An oligonucleotide primer of the QX is mixed in solution with a complimentary oligonucleotide R1 (see, below) such that they form a hybrid duplex. This duplex is further mixed with the reagents in the Table IV provided below which notably include a fluorescein-labeled deoxyriboadenine tetraphosphate (i.e., a fluorescein-labeled 2'-terminator nucleotide) and DNA polymerase capable of incorporating such labeled tetraphosphate. See, U.S. patent application Ser. No. 10/879,494, entitled "SYNTHESIS AND COMPOSITIONS OF 2'-TERMINATOR NUCLEOTIDES", filed Jun. 28, 2004 and Ser. No. 10/879,493, entitled "2'-TERMINATOR NUCLEOTIDE-RELATED METHODS AND SYSTEMS," filed Jun. 28, 2004, which are both incorporated by reference. Incubation of the mixture at a temperature of 60° C. for, e.g., one hour could causes the 3' terminus of the sequence QX to be extended one nucleotide in a template directed manner, resulting in at least a portion of the QX oligonucleotides being extended at their 3' ends with the fluorescein-labeled deoxyriboadenine 2'-phosphate nucleotides, represented below as Primer QX$^{FAM}$.

TABLE IV

| Mix Component | Concentration |
| --- | --- |
| Tricine pH 8.3 | 50 mM |
| KOAc | 100 mM |
| Glycerol | 8% (w/v) |
| Primer QX | 10 µM |
| Oligonucleotide R1 | 15 µM |
| Fluorescein dA4P | 15 µM |
| G46E L329A E678G CS5 DNA polymerase | 50 nM |
| Mg(OAc)$_2$ | 2.5 mM |

The newly elongated Primer QX$^{FAM}$ are purified from the mixture above using any number of purification methods known to persons of skill in the art. An example of such a method capable of purifying Primer QX$^{FAM}$ from the mixture is High Performance Liquid Chromatography (HPLC). HPLC purification parameters are selected such that the preparation of Primer QX$^{FAM}$ is substantially free of non-extended Primer QX and fluorescein-labeled adenine tetraphosphates. Dual HPLC (Reverse Phase and Anion Exchange HPLC) is known as a method for purifying such molecules.

Once purified, molecules such as Primer QX$^{FAM}$ which contain a BHQ quenching molecule and a fluorescein molecule on the same oligonucleotide generally exhibit a suppressed fluorescein signal due to energy absorbance by the BHQ2 "quencher" molecule.

Optionally, Primer QX$^{FAM}$ is synthesized chemically as described herein.

The sequences referred to in this example are as follows:

```
Primer QX    5'-GCAAGCACCCTATCA$^Q$GGCAGTACCACA-3'
             (SEQ ID NO: 24)
```

(Where Q represents the presence of a BHQ molecule)

```
R1           3'-PCGTTCGTGGGATAGTCCGTCATGGTGTT-5'
             (SEQ ID NO: 25)
```

(Where P represents 3'phosphate)

```
Primer QX$^{FAM}$    5'-GCAAGCACCCTATCA$^Q$GGCAGTACCACA$^F$-3'
                    (SEQ ID NO: 26)
```

(Where Q represents the presence of a BHQ molecule, and F represents a fluorescein-labeled 2' phosphate adenine)

```
Primer HC2   5'-GCAGAAAGCGTCTAGCCATGGCTTA-3'.
             (SEQ ID NO: 27)
```

Use of the Primer in PCR.

A Primer QX$^{FAM}$ as described above is combined with the reagents in Table V.

TABLE V

| Component | Concentration |
| --- | --- |
| Tricine pH 8.0 | 100 mM |
| KOAc | 100 mM |
| Glycerol | 3.5% (v/v) |

TABLE V-continued

| Component | Concentration |
|---|---|
| DMSO | 5% (v/v) |
| Primer QX$^{FAM}$ | 150 nM |
| Primer HC2 | 150 nM |
| dATP | 200 μM |
| dCTP | 200 μM |
| dGTP | 200 μM |
| dTTP | 30 μM |
| dUTP | 300 μM |
| UNG | 1 Unit |
| PPi | 175 μM |
| GLQDSE | 15 nM |
| Target sequence | 10$^6$ copies |
| Mg(OAc)$_2$ | 3.0 mM |

In addition each reaction is brought to 50 μl with DEPC treated water. Some reactions contain a target sequence which serves as a substrate for PCR amplification, while others contain no target. For example, the target can be a DNA sequence identical to the 5' UTR region of the HCV genome. Combinations of these primers in PCR are expected to produce an approximately 244 bp amplicon.

The reactions can be performed using an ABI Prism 7700 Sequence Detector with the following temperature profile:
50° C. 1 minute
93° C. 1 minute
90° C. 15 seconds
60° C. 150"→×60 Cycles For such a PCR to progress, PAP activation of the fluorescein-terminated Primer QX$^{FAM}$ is necessary, and would result in the removal of the fluorescein-labeled deoxyadenine tetraphosphate molecule. Such a release is expected to result in an increase in fluorescent signal at approximately 520 nm wavelength. With monitoring of signal at approximately 520 nm wavelength as the PCR progresses, one would expect to observe an increase in fluorescence in those reactions containing target nucleic acid while observing no increased fluorescence in reactions that do not contain target.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An oligonucleotide or polynucleotide, comprising the formula:

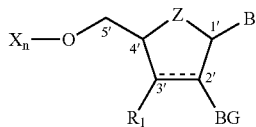

wherein
Z is O or $CH_2$;
B is at least one homocyclic ring, at least one heterocyclic ring, at least one aryl group, or combinations thereof;
BG is a phosphate group,
$R_1$ is H, OH, a hydrophilic group, or a hydrophobic group;
X is a nucleotide or a nucleotide analog;
n is an integer greater than 0; and,
═════represents a single or double bond;
wherein at least one label selected from the group consisting of fluorescent labels, colorimetric labels, chemiluminescent labels, bioluminescent labels, radioactive labels, antibodies, antigens, biotin, haptens, and enzymes is attached to the oligonucleotide or polynucleotide.

2. The oligonucleotide or polynucleotide of claim 1, wherein the 2'-terminator nucleotide comprises a 2'-monophosphate-3'-hydroxyl nucleotide.

3. The oligonucleotide or polynucleotide of claim 1, wherein the 2'-terminator nucleotide is non-extendible by one or more nucleotide incorporating enzymes selected from the group consisting of: a G46E E678G CS5 DNA polymerase, a G46E L329A E678G CS5 DNA polymerase, a G46E L329A D640G S671F CS5 DNA polymerase, a G46E L329A D640G S671F E678G CS5 DNA polymerase, a G46E E678G CS6 DNA polymerase, a ΔZ05R polymerase, a E615G Taq DNA polymerase, a Thermus flavus polymerase, a TMA-25 polymerase, a E678G TMA-25 polymerase, a TMA-30 polymerase, a E678G TMA-30 polymerase, a Tth DNA polymerase, a Thermus specie SPS-17 polymerase, a E615G Taq polymerase, a Thermus Z05R polymerase, a T7 DNA polymerase, a Kornberg DNA polymerase I, a Klenow DNA polymerase, a Taq DNA polymerase, a Micrococcal DNA polymerase, an alpha DNA polymerase, a reverse transcriptase, an AMV reverse transcriptase, an M-MuLV reverse transcriptase, a DNA polymerase, an RNA polymerase, a E. coli RNA polymerase, an SP6 RNA polymerase, a T3 RNA polymerase, a T4 DNA polymerase, a T7 RNA polymerase, an RNA polymerase II, a terminal transferase, a polynucleotide phosphorylase, and a ribonucleotide incorporating DNA polymerase.

4. The oligonucleotide or polynucleotide of claim 1, wherein B comprises a formula selected from the group consisting of:

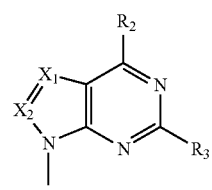

a)

wherein
$X_1$ and $X_2$ are independently selected from $CR_8$ and N;
$R_2$ is H, OH, or $NR_4R_5$;
$R_3$ is H, OH, or $NR_6R_7$;
$R_4$, $R_5$, $R_6$, and $R_7$ are independently selected from H, an alkyl group, a benzyl group, an aryl group, an aryloxy group, and combinations thereof; and R<sub>8</sub> is H, a halo group, an alkyl group, an alkenyl group, an alkynyl group, an alkyl amine group, an alkenyl amine group, an alkynyl amine group, an alkyl alcohol group, an alkenyl alcohol group, an alkynyl alcohol group, unsubstituted polyethylene glycol, or substituted polyethylene glycol;

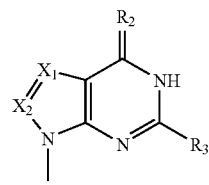
b)

wherein $X_1$ and $X_2$ are independently selected from CH and N;

$R_2$ is O or S;

$R_3$ is H, OH, or $NR_4R_5$; and, $R_4$ and $R_5$ are independently selected from H, an alkyl group, an alkenyl group, a benzyl group, an aryl group, and combinations thereof;

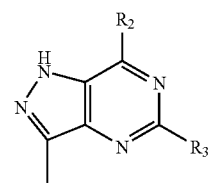
c)

wherein $R_2$ is H, OH, or $NR_4R_5$;

$R_3$ is H, OH, or $NR_6R_7$; and, $R_4$, $R_5$, $R_6$, and $R_7$ are independently selected from H, an alkyl group, an alkenyl group, an alkynyl group, a benzyl group, an aryl group, and combinations thereof;

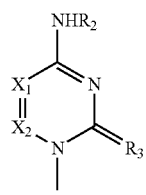
d)

wherein $X_1$ and $X_2$ are independently selected from CH and N;

$R_2$ is selected from H, an alkyl group, an alkenyl group, a benzyl group, an aryl group, an aryloxy group, or combinations thereof; and, $R_3$ is O or S;

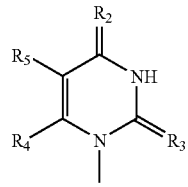
e)

wherein $R_2$ and $R_3$ are independently selected from O and S; and, $R_4$ and $R_5$ are independently selected from H, $NH_2$, SH, OH, an alkyl group, an alkenyl group, a benzyl group, an aryl group, an aryloxy group, an alkoxy group, a halo group, and combinations thereof;

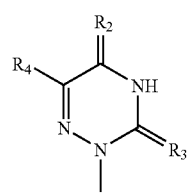
f)

wherein $R_2$ and $R_3$ are independently selected from O and S; and, $R_4$ is H, $NH_2$, SH, OH, an alkyl group, an alkenyl group, a benzyl group, an aryl group, an aryloxy group, an alkoxy group, a halo group, or combinations thereof;

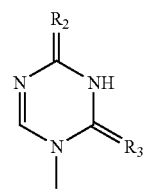
g)

wherein $R_2$ and $R_3$ are independently selected from O and S;

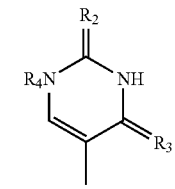
h)

wherein $R_2$ and $R_3$ are independently selected from O and S; and, $R_4$ is H, an alkyl group, an alkenyl group, or an alkynyl group;

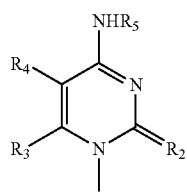

i)

wherein
- $R_2$ is O or S; and,
- $R_3$ and $R_4$ are independently selected from H, $NH_2$, SH, OH, COOH, $COOCH_3$, $COOCH_2CH_3$, CHO, $NO_2$, CN, an alkyl group, an alkenyl group, an alkynyl group, a benzyl group, an aryl group, an aryloxy group, an alkoxy group, a halo group, and combinations thereof; and,
- $R_5$ is an alkyl group, an alkenyl group, an aryl group, a benzyl group, or combinations thereof;

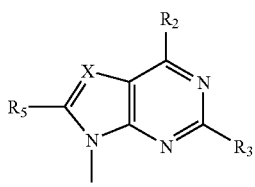

j)

wherein
- X is CH or N;
- $R_2$ and $R_3$ are independently selected from H, OH, and $NHR_4$;
- $R_4$ is H, an alkyl group, an alkenyl group, a benzyl group, an aryl group, or combinations thereof; and,
- $R_5$ is OH, $NH_2$, SH, a halo group, an ether group, a thioether group, an alkyl group, an alkenyl group, an alkynyl group, an alkylamine group, an alkenylamine group, an alkynylamine group, or combinations thereof; and,

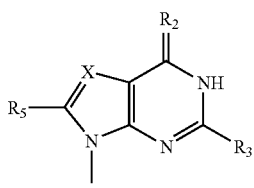

k)

wherein
- X is CH or N;
- $R_2$ is O or S;
- $R_3$ is H, OH, or $NHR_4$;
- $R_4$ is H, an alkyl group, an alkenyl group, a benzyl group, an aryl group, or combinations thereof; and,
- $R_5$ is OH, $NH_2$, SH, a halo group, an ether group, a thioether group, an alkyl group, an alkenyl group, an alkynyl group, an alkylamine group, an alkenylamine group, an alkynylamine group, or combinations thereof.

5. The oligonucleotide or polynucleotide of claim 1, wherein at least one label is attached to the oligonucleotide or polynucleotide.

6. The oligonucleotide or polynucleotide of claim 1, wherein the label is attached to the oligonucleotide or polynucleotide via at least one linker moiety.

7. The oligonucleotide or polynucleotide of claim 1, wherein the label comprises at least one a donor moiety, at least one quencher moiety, and/or at least one acceptor moiety.

8. A kit, comprising one or more of:
- (a) instructions for producing an oligonucleotide or polynucleotide comprising a 2'-terminator nucleotide of claim 1; or,
- (b) at least one oligonucleotide or polynucleotide comprising a 2'-terminator nucleotide of claim 1.

\* \* \* \* \*